United States Patent
Penner et al.

(10) Patent No.: US 8,845,682 B2
(45) Date of Patent: Sep. 30, 2014

(54) VASCULATURE CLOSURE DEVICES AND METHODS

(75) Inventors: Abraham Penner, Tel Aviv (IL); Lone Wolinsky, Ramat Gan (IL); Alon Ben-Yosef, Ramot Manasha (IL)

(73) Assignee: E-Pacing, Inc., Wilmington, DE (US)

( * ) Notice: Subject to any disclaimer, the term of this patent is extended or adjusted under 35 U.S.C. 154(b) by 402 days.

(21) Appl. No.: 12/852,893

(22) Filed: Aug. 9, 2010

(65) Prior Publication Data

US 2011/0087270 A1  Apr. 14, 2011

Related U.S. Application Data

(60) Provisional application No. 61/251,054, filed on Oct. 13, 2009, provisional application No. 61/285,503, filed on Dec. 10, 2009.

(51) Int. Cl.
*A61B 17/03* (2006.01)

(52) U.S. Cl.
USPC ........ 606/213; 623/1.11; 623/1.13; 623/1.18; 623/1.35; 623/1.44; 623/1.22; 623/1.15; 606/151; 606/215

(58) Field of Classification Search
USPC ........ 606/213, 215, 151, 191; 623/1.11, 1.13, 623/1.15, 1.18, 1.22, 1.44
See application file for complete search history.

(56) References Cited

U.S. PATENT DOCUMENTS

| | | | |
|---|---|---|---|
| 4,744,364 A | 5/1988 | Kensey | |
| 4,852,568 A | 8/1989 | Kensey | |
| 4,890,612 A | 1/1990 | Kensey | |
| 5,108,421 A | 4/1992 | Fowler | |
| 5,192,300 A | 3/1993 | Fowler | |
| 5,192,302 A | 3/1993 | Kensey et al. | |
| 5,275,616 A | 1/1994 | Fowler | |
| 5,282,827 A | 2/1994 | Kensey | |
| 5,304,184 A | 4/1994 | Hathaway et al. | |
| 5,320,639 A | 6/1994 | Rudnick | |
| 5,340,399 A | 8/1994 | Uftring et al. | |
| 5,370,660 A | 12/1994 | Weinstein et al. | |
| 5,383,896 A | 1/1995 | Gershuny et al. | |
| 5,389,106 A | 2/1995 | Tower | |
| 5,413,571 A | 5/1995 | Katsaros et al. | |

(Continued)

FOREIGN PATENT DOCUMENTS

| | | |
|---|---|---|
| EP | 534696 | 3/1993 |
| EP | 1057459 A1 | 12/2000 |

(Continued)

OTHER PUBLICATIONS

PCT International Search Report and Written Opinion mailed May 17, 2011 for PCT/US2010/052322(18 pages).

(Continued)

*Primary Examiner* — Vy Q Bui
(74) *Attorney, Agent, or Firm* — Sutherland Asbill & Brennan LLP

(57) ABSTRACT

Vasculature closure devices, and systems and methods for their use, are provided. In one embodiment, the vasculature closure device includes an expandable support frame deployable within a vessel and a sealing membrane at least partially supported by the expandable support frame. Upon expanding the support frame, the vasculature closure device is configured to intraluminally position the sealing membrane against a puncture site existing in a vessel wall.

32 Claims, 36 Drawing Sheets

(56) References Cited

U.S. PATENT DOCUMENTS

| | | | |
|---|---|---|---|
| 5,476,469 A | 12/1995 | Hathaway et al. | |
| 5,486,195 A | 1/1996 | Myers et al. | |
| 5,496,332 A | 3/1996 | Sierra et al. | |
| 5,540,715 A | 7/1996 | Katsaros et al. | |
| 5,593,422 A | 1/1997 | Muijs Van de Moer et al. | |
| 5,601,602 A | 2/1997 | Fowler | |
| 5,620,461 A * | 4/1997 | Muijs Van De Moer et al. | 606/213 |
| 5,630,833 A | 5/1997 | Katsaros et al. | |
| 5,645,566 A | 7/1997 | Brenneman et al. | |
| 5,676,689 A | 10/1997 | Kensey et al. | |
| 5,716,375 A | 2/1998 | Fowler | |
| 5,725,551 A | 3/1998 | Myers et al. | |
| 5,779,719 A | 7/1998 | Klein et al. | |
| 5,782,860 A | 7/1998 | Epstein et al. | |
| 5,824,054 A * | 10/1998 | Khosravi et al. | 623/1.44 |
| 5,922,009 A | 7/1999 | Epstein et al. | |
| 5,951,589 A | 9/1999 | Epstein et al. | |
| 6,056,768 A | 5/2000 | Cates et al. | |
| 6,071,300 A | 6/2000 | Brenneman et al. | |
| 6,080,183 A | 6/2000 | Tsugita et al. | |
| 6,126,675 A | 10/2000 | Shchervinsky et al. | |
| 6,162,240 A | 12/2000 | Cates et al. | |
| 6,183,496 B1 | 2/2001 | Urbanski | |
| 6,245,103 B1 | 6/2001 | Stinson | |
| 6,261,309 B1 | 7/2001 | Urbanski | |
| 6,296,685 B1 | 10/2001 | Cammann et al. | |
| 6,315,787 B1 | 11/2001 | Tsugita et al. | |
| 6,344,049 B1 | 2/2002 | Levinson et al. | |
| 6,371,974 B1 | 4/2002 | Brenneman et al. | |
| 6,379,382 B1 | 4/2002 | Yang | |
| 6,391,048 B1 | 5/2002 | Ginn et al. | |
| 6,398,758 B1 | 6/2002 | Jacobsen et al. | |
| 6,409,739 B1 | 6/2002 | Nobles et al. | |
| 6,458,140 B2 * | 10/2002 | Akin et al. | 606/153 |
| 6,547,806 B1 | 4/2003 | Ding | |
| 6,613,070 B2 | 9/2003 | Redmond et al. | |
| 6,626,914 B2 | 9/2003 | Solem | |
| 6,638,293 B1 | 10/2003 | Makower et al. | |
| 6,663,607 B2 | 12/2003 | Slaikeu et al. | |
| 6,699,261 B1 | 3/2004 | Cates et al. | |
| 6,699,262 B2 | 3/2004 | Redmond et al. | |
| 6,709,455 B1 | 3/2004 | Chouinard | |
| 6,719,777 B2 | 4/2004 | Ginn et al. | |
| 6,749,621 B2 | 6/2004 | Pantages et al. | |
| 6,780,197 B2 | 8/2004 | Roe et al. | |
| 6,818,008 B1 | 11/2004 | Cates et al. | |
| 6,942,674 B2 | 9/2005 | Belef et al. | |
| 6,949,114 B2 | 9/2005 | Milo et al. | |
| 6,962,588 B2 | 11/2005 | Sauvageau et al. | |
| 6,969,397 B2 | 11/2005 | Ginn | |
| 7,022,132 B2 | 4/2006 | Kocur | |
| 7,060,078 B2 | 6/2006 | Hathaway et al. | |
| 7,122,043 B2 | 10/2006 | Greenhalgh et al. | |
| 7,175,646 B2 | 2/2007 | Brenneman et al. | |
| 7,223,266 B2 | 5/2007 | Lindenbaum et al. | |
| 7,316,704 B2 | 1/2008 | Bagaoisan et al. | |
| 7,318,836 B2 * | 1/2008 | Brown et al. | 623/1.13 |
| 7,331,979 B2 | 2/2008 | Khosraui et al. | |
| 7,331,981 B2 | 2/2008 | Cates et al. | |
| 7,335,220 B2 | 2/2008 | Khosraui et al. | |
| 7,361,183 B2 | 4/2008 | Ginn | |
| 7,488,314 B2 | 2/2009 | Segal et al. | |
| 7,537,609 B2 | 5/2009 | Davidson et al. | |
| 7,544,203 B2 | 6/2009 | Chin et al. | |
| 7,572,274 B2 | 8/2009 | Yassinzadeh | |
| 7,621,936 B2 | 11/2009 | Cragg et al. | |
| 7,658,748 B2 * | 2/2010 | Marino et al. | 606/213 |
| 7,892,246 B2 | 2/2011 | Akin et al. | |
| 8,118,833 B2 * | 2/2012 | Seibold et al. | 606/215 |
| 8,460,335 B2 * | 6/2013 | Carpenter | 606/200 |
| 2001/0047202 A1 | 11/2001 | Slaikeu et al. | |
| 2002/0019648 A1 | 2/2002 | Akerfeldt et al. | |
| 2002/0026215 A1 | 2/2002 | Redmond et al. | |
| 2002/0082613 A1 | 6/2002 | Hathaway et al. | |
| 2002/0156495 A1 | 10/2002 | Brenneman et al. | |
| 2002/0165602 A1 | 11/2002 | Douglas et al. | |
| 2002/0193808 A1 | 12/2002 | Belef et al. | |
| 2003/0023267 A1 | 1/2003 | Ginn | |
| 2003/0050664 A1 | 3/2003 | Solem | |
| 2003/0078616 A1 | 4/2003 | Ginn et al. | |
| 2003/0109820 A1 | 6/2003 | Gross et al. | |
| 2003/0125766 A1 | 7/2003 | Ding | |
| 2003/0158578 A1 | 8/2003 | Pantages et al. | |
| 2004/0073255 A1 | 4/2004 | Ginn et al. | |
| 2004/0153122 A1 | 8/2004 | Palermo | |
| 2004/0153123 A1 | 8/2004 | Palermo et al. | |
| 2004/0162578 A1 | 8/2004 | Redmond et al. | |
| 2004/0167570 A1 | 8/2004 | Pantages et al. | |
| 2004/0176798 A1 | 9/2004 | Epstein et al. | |
| 2004/0210244 A1 | 10/2004 | Vargas et al. | |
| 2004/0220610 A1 | 11/2004 | Kreidler et al. | |
| 2004/0260333 A1 | 12/2004 | Dubrul et al. | |
| 2004/0267307 A1 | 12/2004 | Bagaoisan et al. | |
| 2004/0267308 A1 | 12/2004 | Bagaoisan et al. | |
| 2005/0085854 A1 | 4/2005 | Ginn | |
| 2005/0228443 A1 | 10/2005 | Yassinzadeh | |
| 2005/0267522 A1 | 12/2005 | Yassinzadeh | |
| 2005/0267528 A1 | 12/2005 | Ginn et al. | |
| 2005/0267568 A1 | 12/2005 | Berez et al. | |
| 2005/0267570 A1 | 12/2005 | Shadduck | |
| 2005/0273136 A1 | 12/2005 | Belef et al. | |
| 2005/0277980 A1 | 12/2005 | Yassinzadeh | |
| 2006/0106418 A1 | 5/2006 | Seibold et al. | |
| 2006/0135991 A1 | 6/2006 | Kawaura et al. | |
| 2006/0190036 A1 | 8/2006 | Wendel et al. | |
| 2006/0229670 A1 | 10/2006 | Bates | |
| 2006/0241579 A1 | 10/2006 | Kawaura et al. | |
| 2006/0259047 A1 | 11/2006 | Hathaway et al. | |
| 2007/0225748 A1 | 9/2007 | Park et al. | |
| 2007/0225755 A1 | 9/2007 | Preinitz et al. | |
| 2007/0225757 A1 | 9/2007 | Preinitz et al. | |
| 2007/0225758 A1 | 9/2007 | Preinitz et al. | |
| 2007/0276435 A1 | 11/2007 | Yassinzadeh et al. | |
| 2007/0276470 A1 | 11/2007 | Tenne | |
| 2008/0004653 A1 | 1/2008 | Sherman et al. | |
| 2008/0058862 A1 | 3/2008 | Khosravi et al. | |
| 2008/0065150 A1 | 3/2008 | Drasler et al. | |
| 2008/0082122 A1 | 4/2008 | Khosravi et al. | |
| 2008/0097521 A1 | 4/2008 | Khosravi et al. | |
| 2008/0154303 A1 | 6/2008 | Yassinzadeh | |
| 2008/0161849 A1 | 7/2008 | Cates et al. | |
| 2008/0208225 A1 | 8/2008 | Seibold et al. | |
| 2008/0208226 A1 | 8/2008 | Seibold et al. | |
| 2008/0221615 A1 | 9/2008 | Ginn et al. | |
| 2008/0312679 A1 | 12/2008 | Hardert et al. | |
| 2008/0312683 A1 | 12/2008 | Drasler et al. | |
| 2008/0319403 A1 | 12/2008 | Nair et al. | |
| 2009/0004653 A1 | 1/2009 | Yan et al. | |
| 2009/0012596 A1 | 1/2009 | Kocur et al. | |
| 2009/0030450 A1 | 1/2009 | Preinitz et al. | |
| 2009/0036919 A1 | 2/2009 | Preinitz et al. | |
| 2009/0036920 A1 | 2/2009 | Preinitz et al. | |
| 2009/0088591 A1 | 4/2009 | Bosch et al. | |
| 2009/0088793 A1 | 4/2009 | Bagaoisan et al. | |
| 2009/0088794 A1 | 4/2009 | LaFontaine | |
| 2009/0125056 A1 | 5/2009 | Buchbinder et al. | |
| 2009/0143815 A1 | 6/2009 | Eidenschink et al. | |
| 2009/0240321 A1 | 9/2009 | Davidson et al. | |
| 2009/0254173 A1 | 10/2009 | Jang | |
| 2009/0264821 A1 | 10/2009 | Mafi et al. | |
| 2009/0275978 A1 | 11/2009 | Yassinzadeh | |
| 2010/0030259 A1 * | 2/2010 | Pavcnik et al. | 606/215 |
| 2010/0286725 A1 | 11/2010 | Benjamin et al. | |
| 2011/0106131 A1 | 5/2011 | Argentine | |
| 2011/0213410 A1 | 9/2011 | Ginn et al. | |
| 2011/0213411 A1 | 9/2011 | Ginn et al. | |
| 2011/0213412 A1 | 9/2011 | Ginn et al. | |
| 2011/0213449 A1 | 9/2011 | Ginn et al. | |
| 2011/0288580 A1 | 11/2011 | Ginn et al. | |
| 2011/0295316 A1 | 12/2011 | Ginn et al. | |
| 2011/0307006 A1 | 12/2011 | Murphy | |

(56) References Cited

U.S. PATENT DOCUMENTS

| | | |
|---|---|---|
| 2012/0065668 A1 | 3/2012 | Ginn et al. |
| 2012/0083829 A1 | 4/2012 | Ginn et al. |
| 2012/0253387 A1 | 10/2012 | Teichman et al. |

FOREIGN PATENT DOCUMENTS

| | | |
|---|---|---|
| JP | 2001046509 | 2/2001 |
| JP | 2006043296 | 2/2006 |
| WO | 2004012603 A2 | 2/2004 |
| WO | 2005041782 | 5/2005 |
| WO | 2006034114 | 3/2006 |
| WO | 2006078578 | 7/2006 |
| WO | 2008094706 A2 | 8/2008 |
| WO | 2011106713 A2 | 9/2011 |

OTHER PUBLICATIONS

First Examination Report issued by the Australian Patent Office dated Oct. 3, 2013.

* cited by examiner

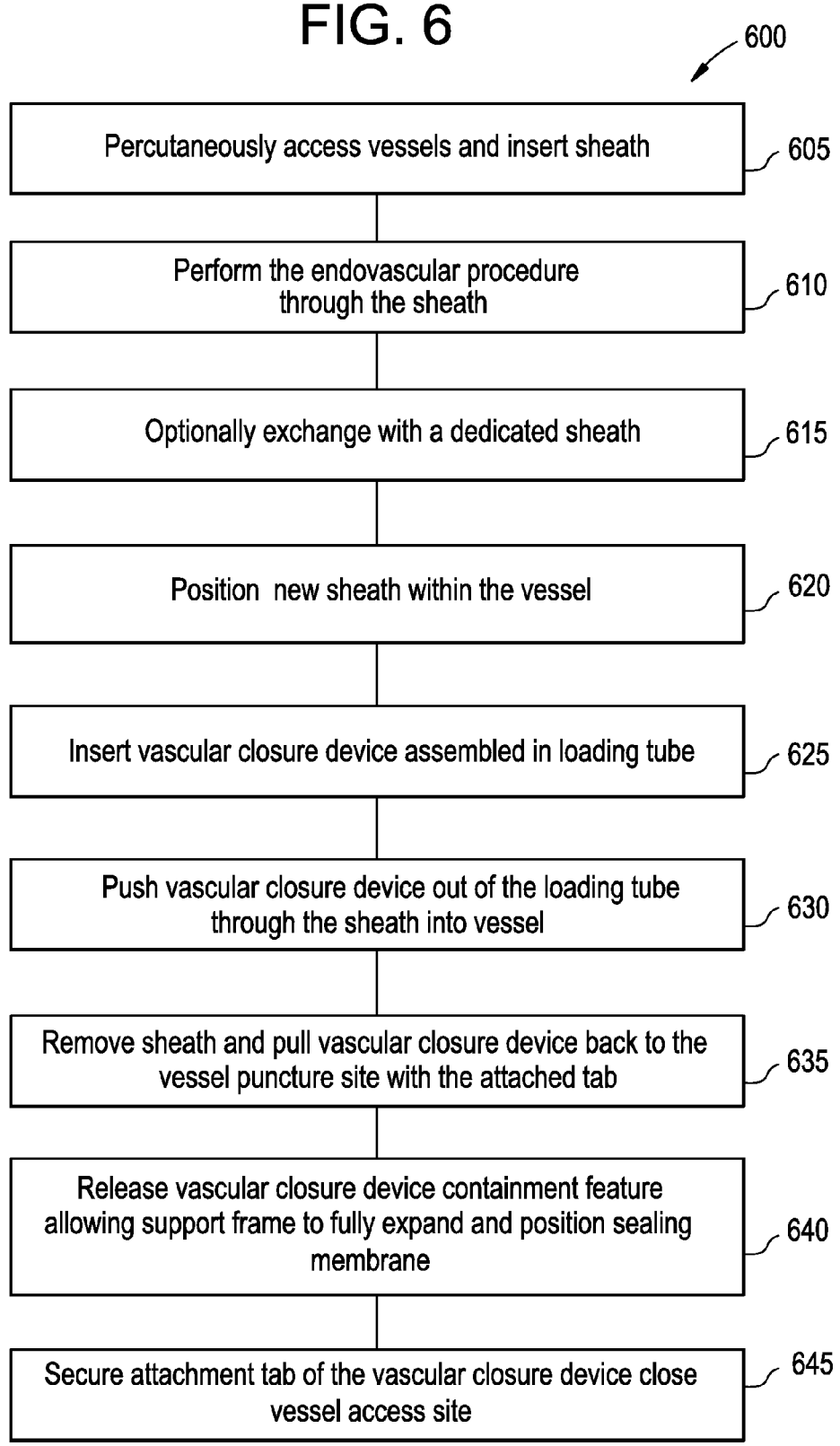

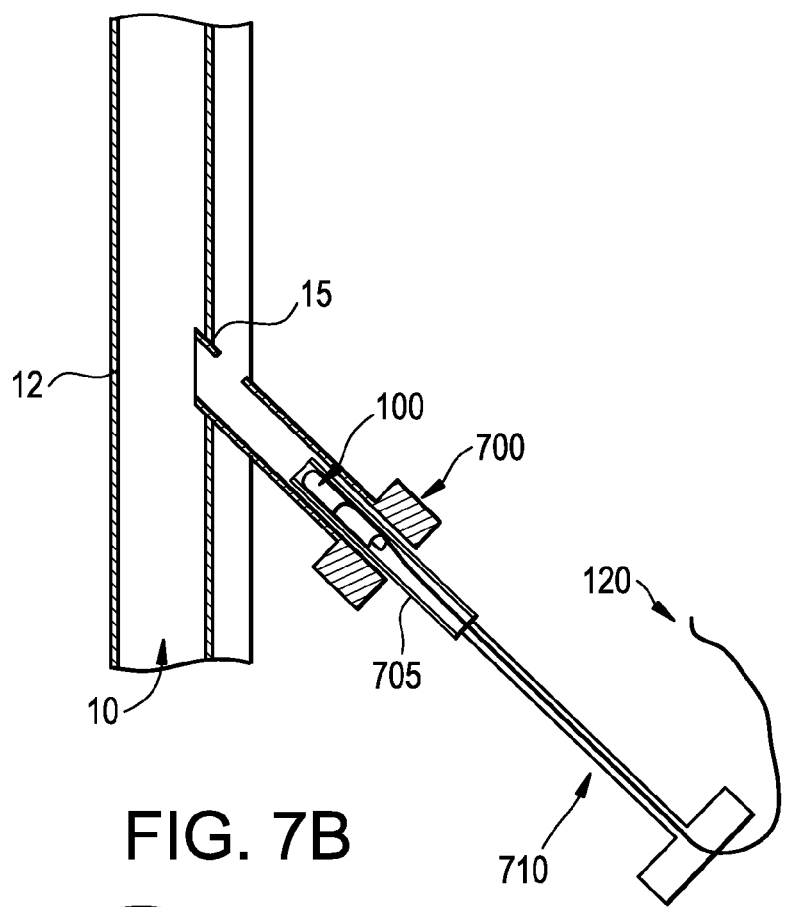
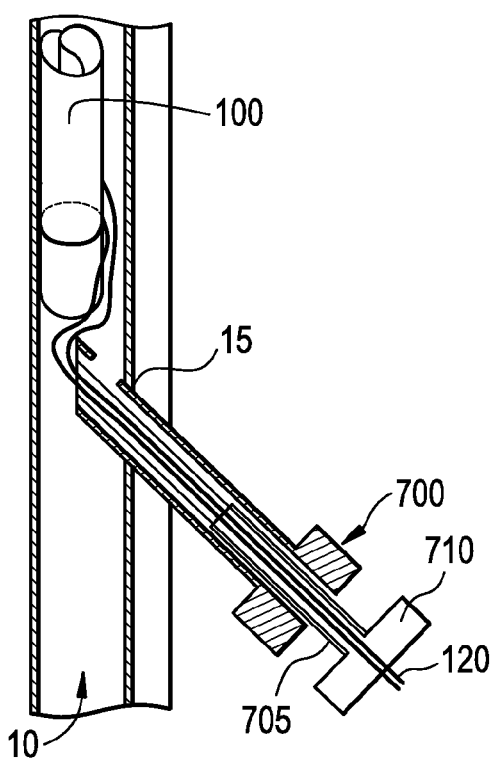

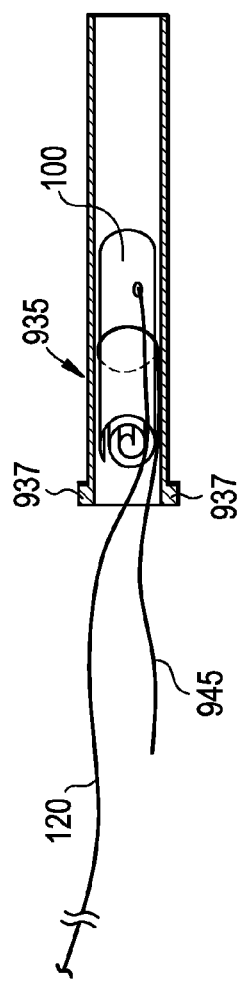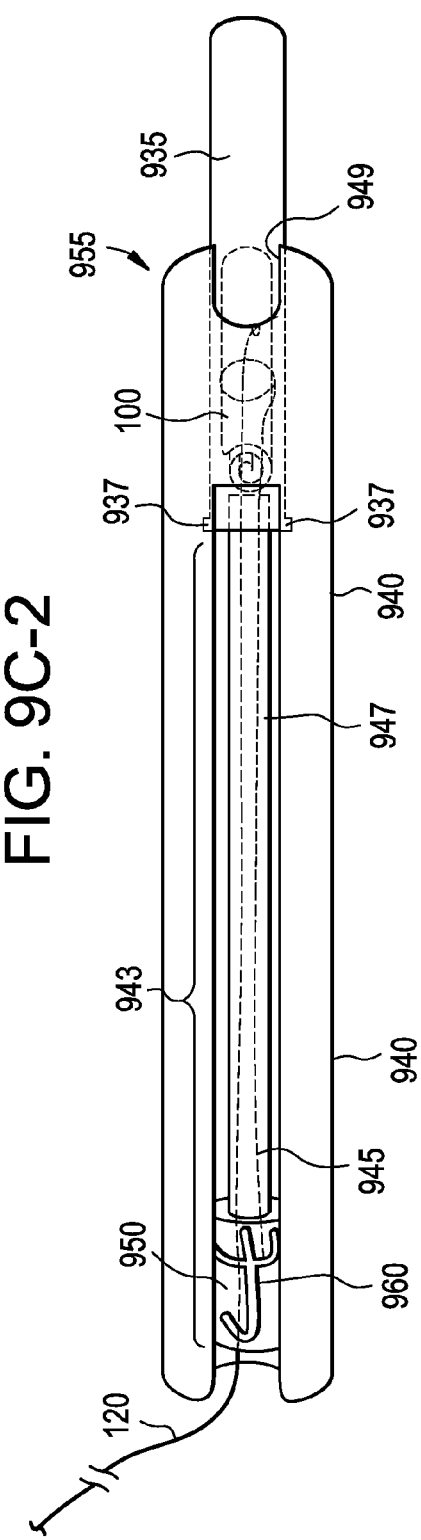

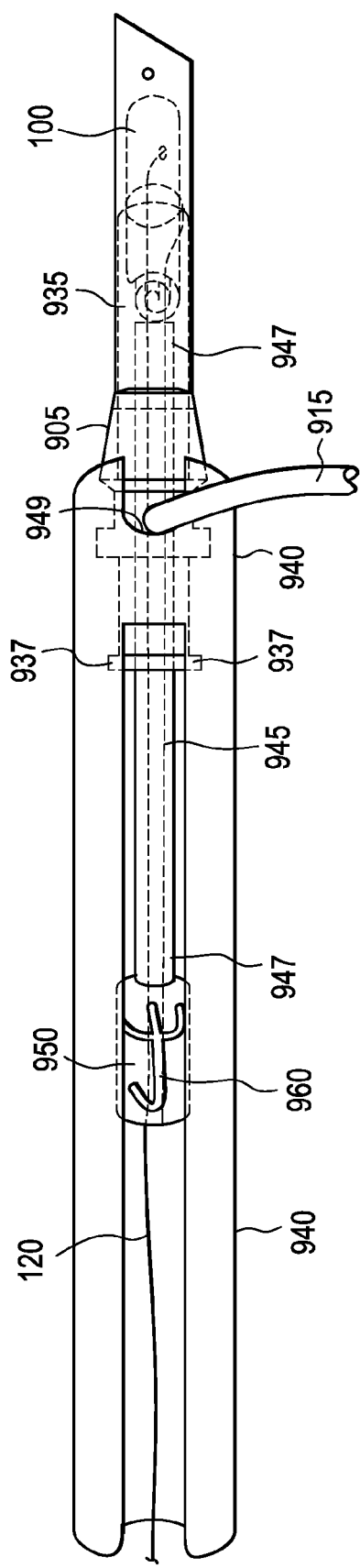

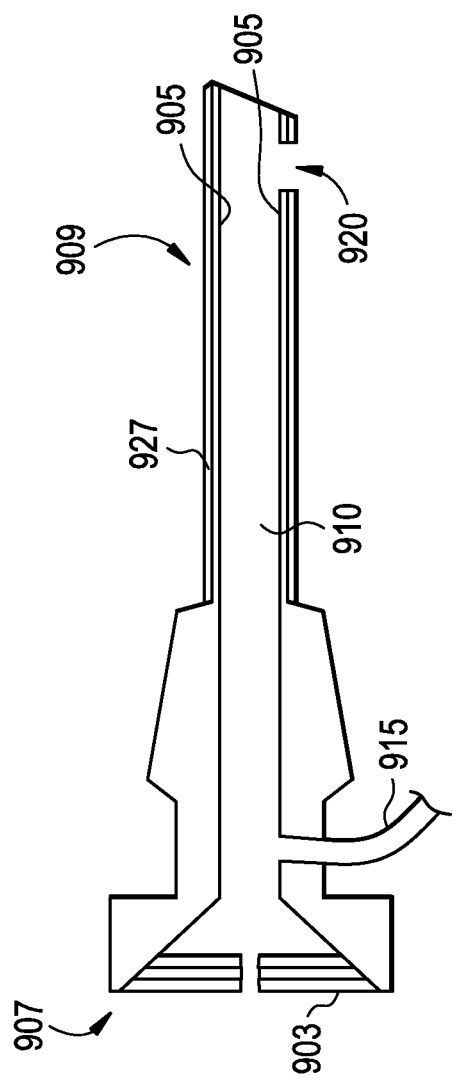

VASCULATURE CLOSURE DEVICES AND METHODS

CROSS-REFERENCE TO RELATED APPLICATIONS

This application claims the benefit of U.S. Provisional Application No. 61/251,054, filed on Oct. 13, 2009, and U.S. Provisional Application No. 61/285,503, filed on Dec. 10, 2009, both of which are incorporated herein by reference in their entirety.

BACKGROUND OF THE INVENTION

This disclosure relates generally to the field of implantable medical devices and associated methods, and more particularly to vascular devices and methods for closing openings in vessel walls.

During certain endovascular surgery procedures, intravascular catheters are inserted through an incision in the patient's skin and underlying tissue to access an artery or vein. After the surgical procedure is completed and the catheter is removed from the vessel, the puncture providing the access through the patient's vessel wall must be closed. This is quite difficult, not only because of the high blood pressure within an artery, but also because of the many layers of tissue that must be penetrated to reach the vessel to achieve closure.

Physicians currently use a number of methods to close a vessel puncture, which include applying localized compression, sutures, collagen plugs, adhesives, gels, and/or foams. To provide localized compression, the physician applies pressure against the vessel to facilitate natural clotting of the vessel puncture. However, this method can take up to a half hour or more and requires the patient to remain immobilized while providing the compression and to remain in the hospital for a period thereafter for observation. The amount of time necessary to apply compression can, in some circumstances, be even greater, depending upon the levels of anti-clotting agents (e.g., heparin, glycoprotein IIb/IIA antagonists, etc.) administered during the endovascular procedure. In addition, applying localized compression can increase the potential for blood clots at the puncture site to become dislodged. Closing procedures in which sutures, collagen plugs, adhesives, gels, and/or foams are applied suffer from variability and unpredictability associated with implantation procedures, many of which are complicated and require highly technical implantation techniques. Some of these closure methods occasionally cause undesirable deformation of the vessels. Moreover, for newer endovascular procedures, such as abdominal or thoracic aortic aneurysm repair, percutaneous valve replacement and repair, or cardiac ablation, which use large diameter delivery systems typically in the range of 8-25 Fr, these conventional closure methods are suboptimal.

Thus, there is a desire for improved vasculature closure devices and methods for deploying and performing treatment using the same. It would, therefore, be advantageous to provide a vasculature closure device that would more quickly and effectively close vessel wall punctures.

BRIEF SUMMARY

Vasculature closure devices and systems and methods for their use are provided. According to one aspect, a vasculature closure device is provided. In one embodiment, the vasculature closure device includes an expandable support frame deployable within a vessel and a sealing membrane at least partially supported by the expandable support frame. Upon expanding the support frame, the vasculature closure device is configured to intraluminally secure the sealing membrane against a puncture site existing in a vessel wall.

According to another aspect, a method is provided for closing a vessel puncture. In one embodiment, the method includes deploying, via a sheath, a vasculature closure device including a support frame and a sealing membrane into a vessel through the puncture site, wherein the support frame is in a compressed configuration during deployment; and then positioning and expanding the support frame within the vessel to cause the sealing membrane to at least partially seal the puncture site.

According to yet another aspect, a system is provided for closing a vessel puncture. In one embodiment, the system includes a vasculature closure device that includes an expandable support frame and a sealing membrane at least partially supported by the expandable support frame. The vasculature closure device is configured to expand from a collapsed configuration to intraluminally secure the sealing membrane against a puncture site existing in a vessel. The system can further include a sheath operable to receive the vasculature closure device in the collapsed configuration and to facilitate deploying the vasculature closure device through the puncture site and into the vessel and a push rod operable to advance the vasculature closure device through the sheath.

BRIEF DESCRIPTION OF THE DRAWINGS

FIG. 6 is a flow diagram illustrating a method for delivering and securing a VCD according to an example embodiment.

FIGS. 7A-7D are cross-sectional views illustrating a delivery system and stages of delivering and securing a VCD within a vessel according to one embodiment.

FIGS. 9A-9I are cross-sectional views illustrating a delivery system and stages of advancing a VCD therethrough according to another embodiment.

DETAILED DESCRIPTION

Figure 1:
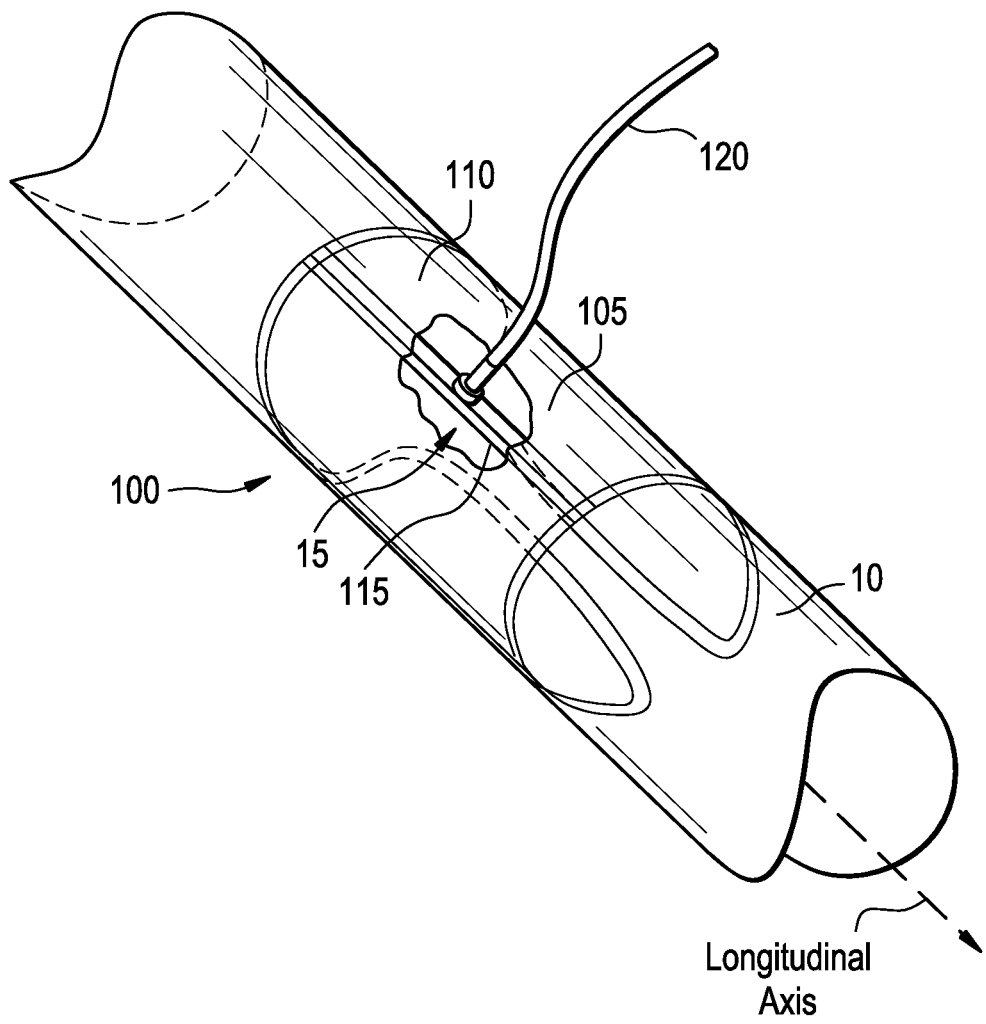
FIG. 1 is an illustration of an implanted vasculature closure device (VCD) according to one embodiment.

Improved vasculature closure devices and systems to facilitate hemostasis and closure of vessel punctures are provided, along with methods for delivering the vascular closure device (VCD) into a patient in need thereof. A VCD, according to various embodiments, includes at least one sealing membrane and at least one support frame attached, integrated, or otherwise supporting the sealing membrane. The support frame is utilized to expand the sealing membrane from a collapsed configuration to an expanded configuration when deployed within a vessel. The support frame can be configured such that it expands enough to force the sealing membrane against a vessel puncture. The pressure exerted by the support frame can vary, but is effective to at least partially maintain the VCD at the desired position within the vessel—which at least partially presses the sealing membrane against the vessel puncture. Upon positioning and exerting pressure by the sealing membrane against the vessel puncture, blood leakage is prevented and/or reduced, and hemostasis and healing are promoted. In some instances, the sealing membrane of the VCD may significantly reduce blood leakage from the vessel puncture, while complete hemostasis is achieved by a thrombus formed on or around the sealing membrane against the puncture. Thrombus forming capabilities may be enhanced by providing thrombus promoting materials on the sealing membrane and/or the anchoring tab or pull wire. The VCD may be left in the secured position within the vessel for essentially any period of time, which may be indefinitely in certain embodiments.

According to various embodiments, portions of the VCD are biodegradable, bioabsorbable, and/or bioerodable (collectively referred to herein as "biodegradable" unless expressly stated otherwise), such that after a period of time portions degrade, absorb, or erode. For example, at least the sealing membrane, and in some embodiments the support frame or portions thereof and/or an anchoring tab or pull wire, absorb after time, minimizing the components remaining within the vessel over time, which simplifies subsequent access at or near the vessel puncture site and reduces potential long-term complications. The shape, configuration, and composition of the various components of the VCD, and the systems and methods for delivering the same, can be embodied in a number of manners, representative examples of which are described below.

The VCD described herein may be used to close punctures or penetrations in vessels in human or other animals (e.g., mammalian). Such an animal may be referred to herein as a patient. As used herein, the term "vessel" refers to arteries, veins, other vascular lumens for carrying blood or lymph, or other body lumens, such as, but not limited to, body lumens of the gastrointestinal system (e.g., the esophagus, the stomach, the small intestine, or the large intestine), the airway system (e.g., the trachea, the bronchus, or the bronchioles), the urinary system (e.g., the bladder, the ureters, or the urethra), or the cerebrospinal system (e.g., subarachnoid space or the ventricular system around and/or inside the brain and/or the spinal cord). The VCD can be dimensioned for effective use with a variety of vessel anatomies and sizes in adult and pediatric patients, as well as with punctures at a variety of vessel sites within the patient. It is envisioned that the VCD can be adapted for use in closing punctures in other body lumens in conjunction with various surgical procedures. For example, in one other embodiment, the VCD can be adapted for use to close lumen punctures during natural orifice transluminal endoscopic surgery or to close a lumbar puncture.

Vasculature Closure Devices

Referring to the figures, FIG. 1 depicts a VCD 100 implanted within a vessel 10 according to one embodiment. The VCD 100, according to this embodiment, includes a sealing membrane 105 and a peripheral support frame 110 providing shape and support to the sealing membrane 105 along at least a portion of the sealing membrane's 105 periphery. As shown in FIG. 1, the VCD 100 is implanted intraluminally within a patient's vessel 10 and positioned and secured therein to at least temporarily seal a target area at or near a vessel puncture site 15 (which is interchangeably referred to herein as the "access hole," "access site," "vessel puncture," "puncture hole," "puncture site," or other similar variations thereof) existing through the vessel 10 wall. In one embodiment, the VCD 100 is held in place due to the predetermined shape of the peripheral support frame 110 and/or its tendencies toward a natural stable shape (e.g., by shape memory materials, etc.) until hemostasis at the puncture site 15 occurs. In other embodiments, as described in more detail herein, all or a portion of the VCD 100 is biodegradable, which allows those components to degrade, absorb, or erode after a period of time such that, if any, only a portion of the VCD 100 remains within the vessel.

The sealing membrane 105, and thus generally the VCD 100 of this embodiment, may be formed in any shape that may be rolled and unrolled along a longitudinal axis generally aligned with and extending along the length of the vessel 10 when implanted. For example, a simple form is similar in configuration to a sheet that can roll or unroll, or a tube that is slit entirely along its longitudinal axis (referred to as a "gull wing" shape in U.S. Provisional Application No. 61/251,054). As described below, however, any other shape that can be collapsed and then expanded within a vessel to promote securement of the VCD 100 can be provided.

According to the embodiment shown in FIG. 1, the VCD 100 further includes a cross-member support 115 extending at least partially between opposite sides of the peripheral support frame 110. The cross-member support 115, due to its rigidity or at least partial rigidity, and/or the tension between the peripheral support frame 110, provides structural and shape support to the sealing membrane 105 at or near its center, as described in more detail with reference to FIG. 2. Such additional support is beneficial when positioned against a puncture site 15 to avoid membrane sagging at the puncture site 15. The additional support is also beneficial during delivery, providing longitudinal strength around which the sides of the sealing membrane 105 can be rolled, helping to maintain the VCD 100 in its rolled or collapsed configuration to fit within a delivery sheath or other delivery system.

An anchoring tab 120 is also secured to the VCD 100, according to one embodiment. The anchoring tab 120 may be attached to and/or extend from the sealing membrane 105, the cross-member support 115, and/or the support frame 110. During placement of the VCD 100, the anchoring tab 120 may be pulled in the proximal direction (away from and out of the puncture site 15), thereby pulling the VCD 100 against the inner vessel wall so that it can be oriented at or near the target area at the puncture site 15. The orientation of the anchoring tab 120 and/or the cross-member support 115 relative to the sealing membrane 105 surface further facilitates centering the VCD 100 within the vessel 10 during implantation, as the VCD 100 will migrate within the vessel 10 (typically downstream) until the anchoring tab 120 abuts an edge of the vessel puncture 15. Thus, the position of the cross-member support 115 may be adjusted along the width of the sealing membrane 105 and/or the position of the anchoring tab 120 may be adjusted along the length of the cross-member support 115 to accommodate for anticipated VCD 100 migration within the vessel 10.

According to one embodiment, the anchoring tab 120 may be affixed (e.g., sutured, glued, hooked, held by an elastic retaining means, etc.) to the patient's epidermis, dermis, subdermal layer, adipose layer, or muscle tissue at or near the vessel access site (e.g., at or near the initial incision created for access to the vessel). According to various embodiments, the VCD 100 may additionally, or instead, include a pull string, which similarly facilitates positioning the VCD 100 at or near the target area by pulling distally. The pull string can be attached to the VCD 100, such as to the sealing membrane 105, the cross-member support 115, and/or the support frame 110, or it may be attached to and extend from the anchoring tab 120.

According to one embodiment, the anchoring tab 120 is flexible and may vary in size. In one embodiment, the anchoring tab 120 has a relatively thin cross section, such as being thread-like, or a thick cross section, such as a diameter similar to or slightly smaller than the puncture site 15 (e.g., from approximately 1 mm to approximately 9.0 mm in diameter). The anchoring tab 120 beneficially may further assist in promoting hemostasis by at least partially filling the puncture site 15 and the access channel through the patient's tissue. In one embodiment, the anchoring tab 120 and a pull string are integrated and together are sufficiently long enough to exit the proximal end of a delivery sheath or other delivery system (e.g., approximately 10 cm to approximately 100 cm). Excess length may be removed after securing the anchoring tab 120 to the patient's epidermis, dermis, sub-dermal layer, adipose layer, or muscle tissue at or near the puncture site. In other embodiments, the anchoring tab 120 and pull string are different members separately attached or otherwise included with the VCD 100; have different diameters, widths, and lengths; and/or are constructed from different materials. For example, the anchoring tab 120 may be fabricated shorter (e.g., approximately 10 mm to approximately 100 mm) than a pull string and/or may be thicker than a pull string. In one embodiment, an anchoring tab 120 may also include a connecting means at its proximal end, such as an eye, a hook, a toggle, and the like, to which a separate pull string can be permanently or removably attached.

It is appreciated that FIG. 1 is provided to depict an one orientation of a VCD 100 within a vessel 10, and that any VCD according to the various embodiments described herein, such as VCDs including radially expandable support frames as described with reference to FIGS. 5A-5G, may be similarly positioned intraluminally to secure or otherwise retain a membrane against a vessel at or near a puncture site. These embodiments are described in more detail with reference to the following figures.

Figure 2:
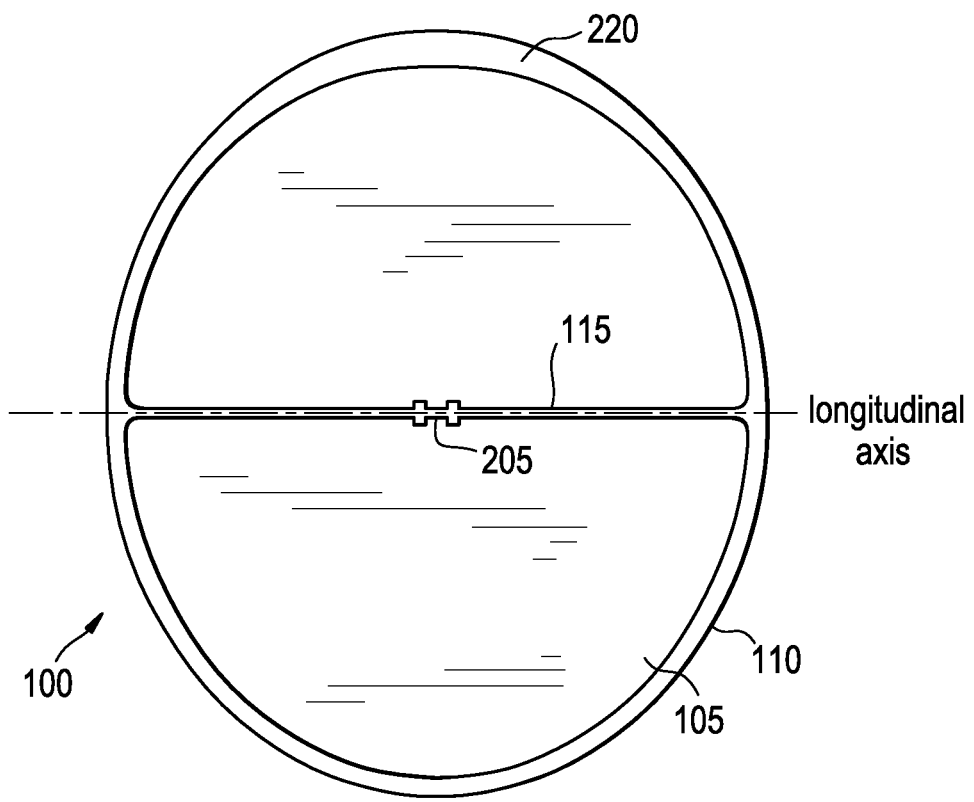
FIG. 2 is an illustration of a VCD according to one embodiment.

FIG. 2 illustrates one embodiment of a VCD 100, similar to the VCD illustrated in FIG. 1, implanted within a vessel. According to this embodiment, the VCD 100 includes a sealing membrane 105 and a peripheral support frame 110 at least partially supporting, and integrated or otherwise affixed at or near the peripheral edge of, the sealing membrane 105. In this embodiment, VCD 100 further includes a cross-member support 115 extending between opposite sides of the peripheral support frame 110. Here, the VCD 100 has a circular or oval shaped sealing membrane 105 and a circular or oval shaped peripheral support frame 110 that approximately follows the shape of the sealing membrane 105. However, as stated herein, the shape of the sealing membrane and the peripheral support frame may vary, according to other embodiments, as desired.

With reference to the embodiment of FIG. 2, the peripheral support frame 110 is formed in a pre-shaped configuration such that in its natural stable state the peripheral support frame 110 has a radius of curvature larger than (i.e., flatter and having a greater radius) than the radius of curvature of the vessel interior within which it will be implanted. For example, if the vessel within which the VCD 100 will be implanted has a diameter ranging between approximately 4.5 mm and approximately 9 mm (e.g., like that of a common femoral artery), then the peripheral support frame 110 may be pre-shaped with a larger radius of curvature that results in a diameter between approximately 7 mm and 20 mm. It is appreciated that the radius of curvature may vary, depending upon the anatomy of the vessel within which the VCD 100 is to be implanted and the desired amount of force exerted by the peripheral support frame 110. Generally, the larger the radius of curvature of the VCD 100 relative to the radius of curvature of the vessel, the greater the force exerted by the support frame 110. At least a portion of the peripheral support frame 110 is formed from a material having elastic properties that will permit rolling or otherwise collapsing the peripheral support frame 110 during delivery and then expanding to its natural stable state upon implantation.

Thus, by having a natural stable state with a larger radius of curvature than the interior vessel wall, the peripheral support frame 110 will expand during implantation to exert a force against the vessel inner wall. This force, coupled with the pressure created by the blood pressure exerted against the membrane 105 and peripheral support frame 110, retains the VCD 100 in place at or near the puncture site. However, the amount of force exerted against the vessel wall is to be limited to avoid injury to the vessel wall. For example, when in an expanded configuration, the VCD 100 (and any other VCD embodiments described herein) may exert a pressure on the vessel inner wall ranging between approximately 0.3 mm Hg to approximately 400 mm Hg, in various embodiments, and in one embodiment, a pressure between approximately 2 mm Hg and approximately 50 mm Hg can be exerted on the vessel inner wall. To achieve a pre-shaped peripheral support frame 110 having the desired shape and curvature described herein, a shape memory metal or alloy, such as nickel-titanium alloy (e.g., Nitinol), a shape memory polymer, or any combination thereof, and/or temperature treatments thereof, may be used to fabricate all or a portion of the peripheral support frame 110.

The cross-sectional thickness of the members comprising the peripheral support frame 110 may contribute to the amount of force exerted by the VCD 100 when in the natural stable (expanded) configuration. For example, according to various embodiments, the thickness may range between approximately 0.01 mm and approximately 2.0 mm, and in some embodiments between approximately 0.04 mm and approximately 0.2 mm, while in other embodiments the thickness may range between 0.2 mm and approximately 0.7 mm. For example, in one embodiment, the members of the peripheral support frame 110 are formed to have a greater width (the dimension lying along the surface of the sealing membrane 105) than the thickness (the dimension perpendicular to the top and the bottom of the sealing membrane 105 surface), such as a width ranging between approximately 0.05 mm and approximately 1.5 mm, or between approximately 0.2 mm and approximately 0.7 mm in one embodiment, and a thickness ranging between approximately 0.01 mm and approximately 0.3 mm, or between approximately 0.04 mm and approximately 0.1 mm in another embodiment. It is appreciated that these dimensions are illustrative and are not intended to be limiting. The width and thickness of the peripheral support frame 110 members may vary as desired and may depend upon the intended implantation.

A VCD 100 having a peripheral support frame 110 also minimizes interference during subsequent vessel access if the VCD 100 (or at least the peripheral support frame 110) remains within the vessel. The peripheral support frame 110 is distanced from the current puncture site because it is oriented only around the periphery of the sealing membrane 105. In addition, by having a support frame only around the periphery of the sealing membrane 105 (and optionally a cross-member support 115), the space occupied by the peripheral support frame 110 can be minimized. In many circumstances, there are a limited number of vessels that provide suitable access for vasculature intervention procedures. Access is especially limited for patients having vessels suffering from stenosis or calcification. Accordingly, in some instances, it may be desirable to reduce the amount of additional vessel obstruction by minimizing the components of the VCD 100 that may remain within the vessel or otherwise inhibit subsequent access, which may include the peripheral support frame 110.

According to some embodiments, the sealing membrane 105 is biodegradable. Thus, after time, at least the sealing membrane 105 will degrade and will not itself obstruct vessel access. According another embodiment, the sealing membrane 105, whether biodegradable or not, is sufficiently thin or composed of material weak enough to not substantially interfere with vessel re-accessing. For example, in some embodiments, the sealing membrane 105 can be partially, or completely, fabricated from a biodegradable material, such as, but not limited to, modified cellulose, collagen, fibrin, fibrinogen, elastin, tissue, biological membrane (e.g., pericardium, etc.), or other connective proteins or natural materials; polymers or copolymers, such as, but not limited to, aliphatic polyester (e.g., poly-L-lactide (PLLA), poly-D-lactide (PDLA)), polyglycolide (PGA), poly(glycolic-co-lactic acid) (PLGA), polydioxanone (PDS), polycaprolactone (PCL), poly(glycolide-co-trimethylene carbonate) (PGA-TMC), polygluconate, polylactic acid-polyethylene oxide copolymers, poly(hydroxybutyrate), polyanhydride, polyphosphoester, poly(amino acids), poly(alpha-hydroxy acid), or any other similar copolymers; magnesium or magnesium alloys; or aluminum or aluminum alloys; as well as any composites and combinations thereof, and combinations of other biodegradable materials, which, after a period of time resorb into the body. In other embodiments, the sealing membrane is partially, or completely, fabricated from any other biocompatible material, which may not be completely bioabsorbable, such as, but not limited to, expanded polytetrafluoroethylene (ePTFE), polyethylene, polypropylene, polyester, polyurethane, silicone, Dacron, urethane, polyaryletheretherketone (PEEK), stainless steel, titanium, nickel-titanium, cobalt, nickel-chromium, gold, platinum, and/or any composite, alloy, or combination of these or other suitable materials. It is appreciated that in some embodiments, the sealing membrane may be fabricated from a combination of one or more biodegradable materials and non-absorbable materials.

Moreover, according to some embodiments, the sealing membrane 105 may be formed as a continuous material, while, in other embodiments, the sealing membrane 105 may be formed in a woven or mesh configuration. A woven or mesh configuration facilitates forming a barrier to blood leakage by sealing as thrombus or other body material or cells attached to the woven or mesh sealing membrane 105. Similarly, the sealing membrane 105 may include holes, perforation, or partial perforation, at least at or near the area designed to be positioned at or near the puncture site. In some embodiments, holes may be provided only at a portion of the sealing membrane 105; though, in other embodiments, as much as 60% or more of the sealing membrane 105 may include holes or perforation. The holes or perforations may be formed in any suitable size, such as having a diameter ranging from approximately 0.05 mm to approximately 2 mm in one embodiment; though, holes or perforations may have other dimensions in other embodiments. Holes or perforations serve to promote cell growth over the sealing membrane 105 and the sealing membrane's 105 integration to the vessel. Moreover, a perforated sealing membrane 105 also reduces the total amount of foreign matter (e.g., the sealing membrane 105) implanted within the patient, and thus promotes membrane degradation. According to some embodiments, sealing membrane 105 materials are chosen to exhibit one or more of the following traits: to avoid inflammation or toxic response when implanted, to have acceptable shelf life, to control degradation rate if biodegradable, to metabolize if biodegradable, and/or to be easily sterilized.

In some embodiments, the peripheral support frame 110 can also be fabricated at least partially from biodegradable materials, such as, but not limited to, those described above. According to one embodiment, the peripheral support frame 110 may be fabricated from materials such as, but not limited to, aliphatic polyester (e.g., poly-L-lactide (PLLA), poly-D-lactide (PDLA), polyglycolide (PGA), poly(glycolic-co-lactic acid) (PLGA)), polydioxanone (PDS), polycaprolactone (PCL), poly(glycolide-co-trimethylene carbonate) (PGA-TMC), polygluconate, polylactic acid-polyethylene oxide copolymers, poly(hydroxybutyrate), polyanhydride, polyphosphoester, poly(amino acids), poly(alpha-hydroxy acid), or any other similar copolymers; magnesium or magnesium alloys; or aluminum or aluminum alloys; as well as any composites or combinations thereof, or combinations of other biodegradable materials, which, after a period of time resorb into the body. However, in other embodiments, the peripheral support frame 110 is at least partially fabricated from non-absorbable materials, including, but not limited to, nickel-titanium alloy (Nitinol), stainless steel, titanium, cobalt-based alloy, chromium alloys, gold, platinum, tantalum, a biocompatible polymer, such as a shape memory polymer, or any combination thereof. Thus, for embodiments in which the peripheral support frame 110 is fabricated from non-absorbable materials, it may be desirable to minimize the size and space occupied by the frame, such as is accomplished by its orientation around the periphery of the sealing membrane 105. Moreover, as described above, many of the aforementioned materials or combinations thereof exhibit elastic, super-elastic, and/or shape memory characteristics that can beneficially be formed into a desired shape to permit self-expansion of the VCD 100 to a stable natural state from a flexed or otherwise altered state during implantation and to improve securement of the VCD 100 within a vessel.

Figure 3A:
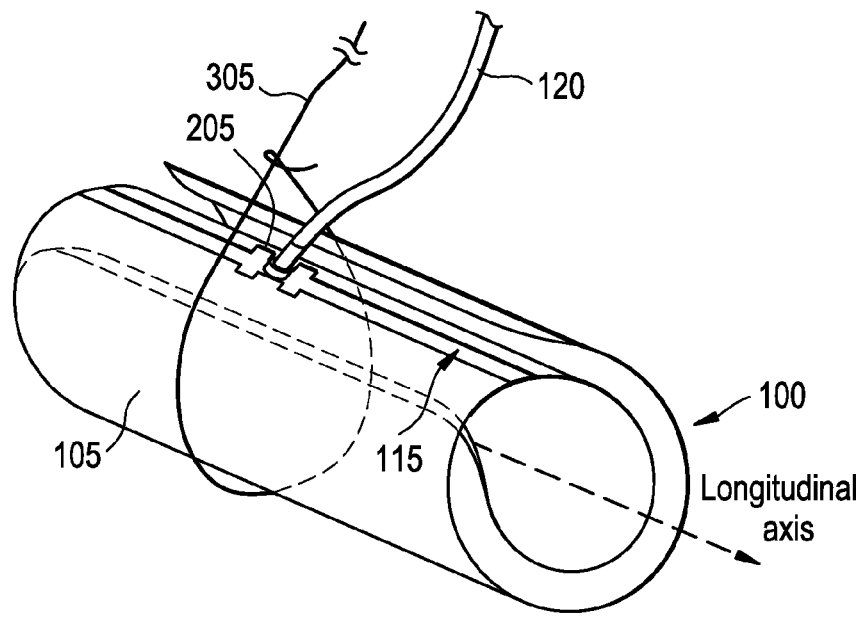
FIGS. 3A-3D are illustrations of a VCD and corresponding containment mechanism according to some representative embodiments.

The cross-member support 115 extending between opposite sides of the peripheral support frame 110 serves at least two functions. First, the cross-member support 115 supports the sealing membrane 105 at or near its center to avoid sagging where it will be in contact with a vessel puncture site, thus improving the seal created therebetween. Second, the cross-member support 115 may include an attachment means 205 for attaching an anchoring tab and/or pull string to the VCD 100, such as is described with reference to FIG. 1. The attachment means 205 may include, but is not limited to, an aperture, a hook, an eye, a post, a tab, adhesive, heat welding, laser welding, mechanical attachment, and the like. For example, in one embodiment, an anchoring tab and/or pull string is releasably affixed to the attachment means 205 prior to implantation (e.g., during manufacturing or prior to delivery). In other embodiments, the anchoring tab and/or pull string may be more permanently affixed to the sealing membrane 105 and/or the cross-member support 115, such as if the anchoring tab is formed from excess sealing membrane material, for example. Additional details regarding anchoring tab and/or pull string configurations are described below. For example, FIG. 3A illustrates a VCD 100 in a collapsed configuration for delivery.

In one embodiment, the cross-member support 115 is fabricated from a material having additional strength and/or rigidity relative to the rest of the peripheral support frame 110, such as is described with reference to straight edge portion of FIG. 4A. Providing additional rigidity to the cross-member support 115 increases the stiffness of the VCD 100 along the longitudinal axis and its center, which will further facilitate maintaining the desired shape when in collapsed configuration, as is described with reference to FIG. 3A. Rigidity of the cross-member support 115 may be enhanced in any number of ways, including, but not limited to, increasing the cross-sectional profiles of the cross-member support 115 relative to the rest of the peripheral support frame 110, forming the cross-member support 115 from a more rigid frame material, reinforcing the cross-member support 115 with a more rigid frame material, or any combination thereof.

According to one embodiment, the cross-member support 115 is fabricated from a biodegradable polymer, a biodegradable metal or metal alloy, any other biodegradable material, or any combination thereof. A biodegradable cross-member support 115 will improve subsequent access to the vessel at or near the implantation site at any time after its degradation. Because the cross-member support 115, in this embodiment, will span across or be located proximate the puncture site, being formed from a biodegradable material will avoid impeding access to the puncture site. In one example embodiment, the cross-member support 115 may be configured as a wire, extending between, but separate from, the peripheral support frame 110 at or near the same position as shown in FIG. 2, which may be biodegradable or non-biodegradable. In other embodiments, a VCD 100 may include a cross-member support 115 fabricated at least partially from a non-absorbable material. In yet other embodiments, a VCD 100 may not include the cross-member support 115, and/or may not include an anchoring tab 120 or pull string, as described above.

According to one embodiment, a VCD 100 having some or all components fabricated from biodegradable materials, is manufactured in a manner to result in a predictable degradation rate. For example, in one embodiment, biodegradable components are fabricated from a material having at least 1 day degradation time, and can be up to at least 720 days. For example, in one embodiment, the degradation time may be between approximately 20 days and approximately 120 days. These degradation rates are illustrative purposes only and are not intended to be limiting. In other embodiments, the degradation time may be greater than or less than these ranges as desired, which may depend upon the implantation site and/or procedure being performed. Moreover, in some embodiments, different components of a VCD 100 can degrade at different rates, such as a VCD 100 having a sealing membrane 105 that degrades at a quicker rate than the peripheral support frame 110 and/or the cross-member support 115.

In addition, the material from which the VCD 100 components are fabricated should be stable over a wide range of temperatures to avoid degradation or defects during manufacturing, sterilization, and storing. Example temperature ranges over which VCD 100 components should be stable may range from approximately −20° C. to approximately 65° C., or, in some embodiments, from approximately −10° C. to approximately 45° C. It is appreciated that, according to some embodiments, VCD 100 components may be stable at temperatures above and below this range. Example materials which exhibit desirable qualities for manufacturing biodegradable VCD 100 components include, but are not limited to, the Resomer® products manufactured by Boheringer Ingelheim GmbH, of Ingelheim am Rhein, Germany, which are based on lactic acid and glycolic acids.

In other embodiments, the VCD 100, including the sealing membrane 105 and the peripheral support frame 110, may be configured in a different shape, such as, but not limited to, oval, asymmetrical, elliptical, rectangular, rhombus, triangular, pentagonal, hexagonal, or any other polygonal shape. In embodiments having a sealing membrane 105 configured in a different shape than that illustrated in FIG. 2, one or more portions of the peripheral support frame 110 may be formed from a material having additional strength and/or rigidity relative to the rest of the peripheral support frame 110, which is illustrated by a portion 220 along one end of the peripheral support frame, which may serve to contain the VCD 100 in the desired collapsed shape during delivery and/or to avoid flaring of the edges or at least a portion of the edges of the sealing membrane 105 during delivery and/or upon implantation. Other representative VCD shapes are described with reference to FIGS. 4A-5G.

In the embodiment shown in FIG. 2, the sealing membrane 105 completely covers the peripheral support frame 110. However, in other embodiments, the sealing membrane 105 may only partially cover the peripheral support frame 110, such as if the sealing membrane 105 extends from the peripheral support frame 110 at or near the center of the VCD 100 and, thus, to allow covering a puncture site within a vessel upon implantation, while the peripheral support frame 110 may extend beyond the sealing membrane 105 along one or more of the edges of the VCD 100. The sealing membrane 105 may be coupled to the peripheral support frame 110 at one or more points along the frame and/or the cross-member support 115 by any suitable manufacturing method, such as described in more detail herein.

To provide the desired hemostasis, the dimensions of the sealing membrane 105 are at least as large as or larger than the puncture site according to one embodiment, such as is illustrated by FIG. 1. The sealing membrane may be larger than the puncture site. However, in other embodiments, the dimensions of the sealing membrane 105 are smaller than that of the puncture site. For example, the sealing membrane 105 may be approximately 10% smaller, or even as much as 50% smaller, than the puncture site, which can still be effective because the hole at the puncture site tends to reduce in size after a delivery sheath or other delivery system is removed from the puncture site. According to various embodiments, the thickness of the sealing membrane 105 is between approximately 5 microns and approximately 500 microns, between approximately 10 microns and approximately 200 microns, or between approximately 30 microns and approximately 150 microns. The thickness of the sealing membrane 105 may be determined at least in part by the method of manufacture, as described herein. Moreover, the thickness of the sealing membrane 105 (and optionally the porosity of the sealing membrane 105) may impact, and thus be adjusted to control, the degradation rate.

The sealing membrane 105 may be formed in any number of configurations, including, but not limited to, a woven membrane, a non-woven membrane, a mesh, a film, a gel, a single membrane, a multilayer membrane, or any combination thereof. The sealing membrane 105 may be constructed according to any number of techniques, including, but not limited to, extrusion, solution deposition, coating, molding, electrospinning, weaving, or any other suitable method for manufacturing polymeric sheets, textiles, or membranes.

According to one embodiment, the sealing membrane 105 is produced either by weaving, air spinning, or electrospinning, which uses an electrical charge to draw fibers from a liquid form. Weaving, air spinning, and electrospinning allow controlling the density, the surface area topography, and the flexibility of the sealing membrane 105. As a result, increased control is provided over the sealing membrane's 105 degradation rate, whereby a larger effective surface area results in faster degradation. Controlling membrane flexibility allows controlling the ability of the sealing membrane 105 to roll or fold into the collapsed configuration during delivery, while also avoiding significant wrinkles or creases, which may otherwise occur with extruded membranes. Moreover, a sealing membrane 105 with reduced density, such as may be accomplished by weaving or electrospinning, increases the compressibility of the sealing membrane 105, which improves the ability of the sealing membrane 105 to adjust to vascular inner wall topography (e.g., surface roughness that may occur from calcification, etc.) and improves its sealing capabilities.

The sealing membrane 105 may be a single material or it may be a composite material. The single or composite material may be porous, non-porous, or a combination thereof.

According to various embodiments, the sealing membrane 105 may have substantially uniform properties throughout, or the sealing membrane 105 may exhibit varied properties, such as including multiple layers of different materials and/or including layers having different densities or porosities. For example, according to one embodiment in which the sealing membrane 105 is formed from multiple layers, the sealing membrane 105 is constructed from at least a first porous material forming a first layer and a second layer formed from a less porous and, thus, smoother material. The first layer may be the same material as the second layer but fabricated in a different manner to generate different porosities, or the first and second layers may be formed from different materials. In one example, a VCD 100 with a sealing membrane 105 having a more porous surface facing inward toward the vessel lumen relative to the surface facing outward toward the vessel's inner wall allows faster degradation of the sealing membrane 105 on its inner surface facing the vessel interior. In another embodiment, however, a less porous layer may face outward toward the vessel wall, providing the smoother surface in contact with blood flowing through the vessel. Weaving and electrospinning, for example, may be used to create various combinations of densities, porosities, and surface area properties, which may differ from the representative examples described herein.

The sealing membrane 105 may be integrated with or otherwise coupled to the peripheral support frame 110 at one or more points along the peripheral support frame 110 and/or the cross-member support 115 using any number of suitable techniques, including, but not limited to, adhesive, solvent adhesion, heat welding, laser welding, ultrasonic welding, mechanical attachment, layered integration, or any combination thereof. The technique chosen to couple the sealing membrane 105 to the peripheral support frame 110 may depend in part on the manufacturing technique utilized to fabricate the sealing membrane 105 and/or the peripheral support frame 110.

According to one embodiment, the peripheral support frame 110 may be sandwiched between two membrane layers forming the sealing membrane 105 and securing the peripheral support frame 110 in position therebetween. For example, in one technique, a first membrane layer is formed over a mandrel, which provides the same, or slightly larger, radius of curvature (and, thus, relatively flatter) as the vessel into which the VCD 100 is intended to be implanted. After forming the first membrane layer of the mandrel, the peripheral support frame 110 is placed over the first membrane layer. In one embodiment, at this step the peripheral support frame 110 is treated into its natural stable state around the mandrel, such as if the peripheral support frame 110 is fabricated from a shape memory metal, metal alloy, or polymer. Though, in other embodiments utilizing shape memory metals, metal alloys, or polymers, the peripheral support frame 110 can be treated to its natural stable state at another stage of manufacturing (e.g., before or after), or the peripheral support frame 110 may not be fabricated from shape memory metals, metal alloys, or polymers at all.

According to one embodiment, the support frame 110 is manufactured from a shape memory alloy, such as nickel-titanium alloy, either by cutting the frame from a sheet of desired dimensions, by cutting from a tube of desired dimensions, or formed from a wire (flat or round cross-section) by crimping, brazing, welding, and the like. Nickel-titanium alloy may be cut by a laser, chemical etching, electro-erosion, or any combination thereof. After cutting and/or otherwise forming the support frame 110 into its desired dimension, the support frame 110 is pre-shaped to its desired natural stable shape (e.g., its super-elastic state, etc.), such as by thermal treatment, as is known in the art for shape memory materials. Pre-shaping may be performed on the mandrel, or separately. According to some embodiments, the support frame 110 surface is further treated, such as, but not limited to, removing oxides, smoothing, electropolishing, passivating to improve corrosion resistance, and/or increasing surface roughness to improve adhesion to a sealing membrane 105. The aforementioned example of forming a support frame 110 is illustrative and is not intended to be limiting.

After applying the peripheral support frame 110 to the mandrel over the first membrane layer, a second membrane layer may be formed over the peripheral support frame 110 and the sealing membrane 105. Accordingly, by fusing or otherwise affixing the two membrane layers with the peripheral support frame 110 sandwiched therebetween, the sealing membrane 105 and the peripheral support frame 110 become an integrated component. Similar techniques may be used in embodiments including a cross-member support 115 or any other support frame structure. Other suitable techniques for coupling a sealing membrane to a support frame can be performed, such as techniques similar to those used for the design and manufacturing of covered stents or stent grafts.

In one embodiment, the sealing membrane 105 and/or the peripheral support frame 110 may be coated, impregnated, covered, and/or include means for releasing chemical components into the surrounding environment, such as within the vessel at or near the puncture site after implantation. Examples of such chemical components include, but are not limited to, hemostatic agents, drugs, biological agents, viruses, cells, or any other material that may influence or control biological processes. For example, one or more chemical components can be utilized to promote the healing of the blood vessel and/or the puncture site; to control, reduce, or mitigate cell proliferation, such as is similar to that utilized by a drug eluting stent; to control, reduce, or mitigate blood coagulation (e.g., by releasing heparin, etc.); to enhance blood coagulation (e.g., by releasing thrombin, etc.); and/or to reduce the risk of infection by releasing antibiotics or other medicinal substances. Chemical components may be applied to the peripheral support frame 110, to the sealing membrane 105, and/or to the anchor tab 120 or pull string by at least partially coating its surface. In other embodiments, the chemical components may be coupled, either mechanically or chemically, to at least one of the materials forming the peripheral support frame 110 and/or the sealing membrane 105, or may be mixed into the sealing membrane 105 during its manufacturing. According to one embodiment, one or more chemical components are released upon the absorption, degradation, or erosion of one or more components of the VCD 100.

According to various embodiments, the total length of the VCD 100, from one edge of the sealing membrane 105 to an opposite edge along the longitudinal axis, may range between approximately 4 mm to approximately 50 mm, and in one embodiment, between approximately 5 mm and approximately 25 mm. According to various embodiments, the diameter of the VCD 100 in a collapsed state, such as is illustrated by and described with reference to FIG. 3A, is at least less than approximately 9 mm, which would be compatible with a 27 Fr introducer sheath, less than approximately 7 mm, which would be compatible with a 21 Fr introducer sheath, or even less than approximately 6 mm, which would be compatible with a 18 Fr introducer sheath. In yet other embodiments, the diameter is less than approximately 4 mm, which would be compatible with a 12 Fr introducer sheath, or even less than approximately 3 mm, which would be compatible with a 9 Fr introducer sheath. In yet another embodiment, the VCD 100, when in a collapsed state, is compatible with, and can be deployed by, anywhere between a 4 Fr to a 8 Fr introducer sheath. The aforementioned dimensions are illustrative and are not intended to be limiting. In other embodiments, the VCD 100 in collapsed or in expanded configurations may be larger than or smaller than the representative examples described herein.

The aforementioned materials, manufacturing techniques, and characteristics of the VCD 100 and individual components may likewise apply to any other VCD embodiment described herein.

FIG. 3A illustrates one embodiment of VCD 100, similar to that illustrated in and described with reference to FIG. 2, in a collapsed configuration for delivery. The VCD 100 can be delivered utilizing a delivery system, such as those described with reference to FIGS. 6-10P, initially inserted and delivered in a collapsed configuration as illustrated in FIG. 3A. Here, VCD 100 is rolled into a collapsed or rolled configuration by rolling the device along the longitudinal axis. The cross-member support 115 may further serve to increase the longitudinal rigidity and stability of the VCD 100 when in a rolled configuration. Without the rigidity provided by the peripheral support frame 110 and/or the cross-member support 115, a containment mechanism, such as is described below, positioned at or near the center of the VCD 100 may cause the edges to flare and/or the sealing membrane 105 to wrinkle. Though, as described herein, in other embodiments, the VCD 100 does not include a rigid cross-member support 115, and may optionally include a non-rigid member cross-member support 115 instead, such as a biodegradable or non-degradable wire. Flaring or wrinkling may thus be reduced by rolling the VCD 100 into a collapsed state.

Also shown with the VCD 100 is a containment mechanism 305 embodied as one or more strings, wires, ribbons, bands, or cords encircling the VCD 100 to releasably retain the VCD 100 in a collapsed configuration. Upon releasing the containment mechanism 305 after suitable positioning within a vessel, the VCD 100 expands to its expanded configuration. As shown in the embodiment of FIG. 3A, the containment mechanism 305 is configured as a thread or other looped member encircling and compressing the VCD 100, such as by using a slip knot, lanyard, or other releasable securing means to selectively release the containment mechanism 305 from around the VCD 100. The containment mechanism 305 further includes at least one end extending from the VCD 100 (and optionally into a delivery system, as described herein) to allow operation and release of the containment mechanism 305 by an operator. In another embodiment, a containment mechanism includes one or more removable pins, one or more releasable wire loops, one or more releasable straps, releasable mesh, or another similar releasable mechanism for restraining the VCD 100 that can be released by an operator. In still another embodiment, a thin restraining tube with a rip cord is assembled over the compressed VCD 100, whereby the rip cord causes the restraining tube to tear or otherwise separate when pulled, releasing the compressed VCD 100. The containment mechanism 305 can also be used for positioning the VCD 100 into its final position across the vessel puncture.

Figure 3B:
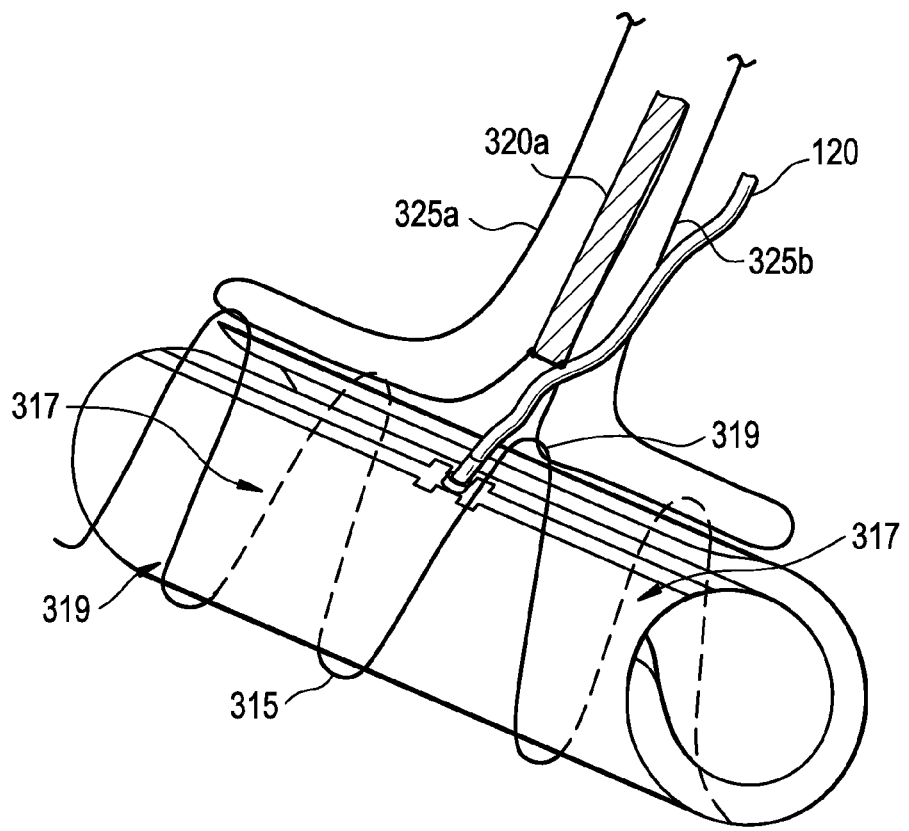
Figure 3C:
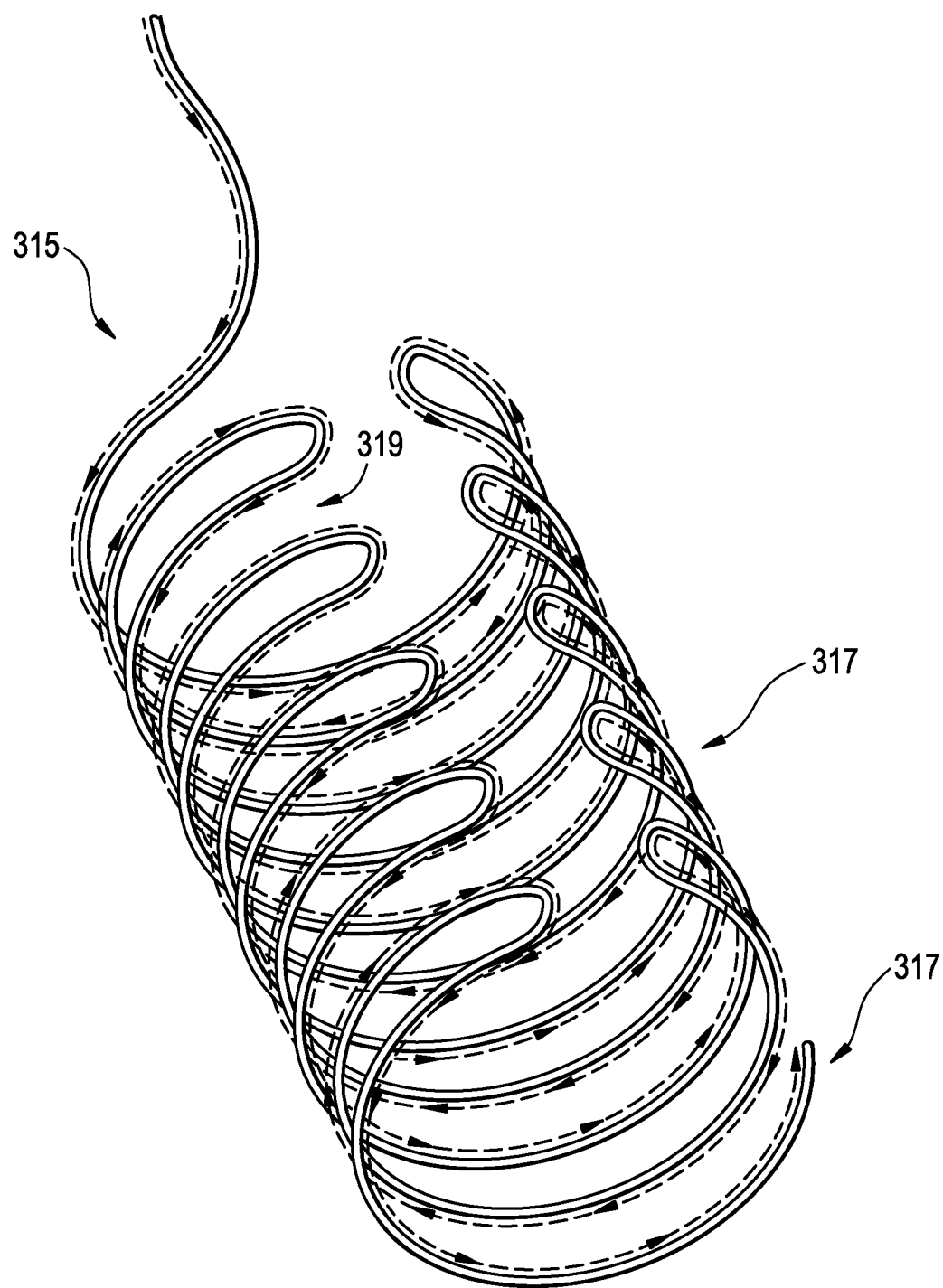

FIG. 3B illustrates another embodiment of a containment mechanism for a VCD 100. In this embodiment, the containment mechanism includes a looped wire 315 formed into alternating series of loops 317, 319. The series of alternating loops 317, 319 are oriented such that a first loop 317 is positioned on one side of the VCD 100 when rolled and the second loop 319, adjacent to the first loop 317, passes under and is positioned on the opposite side of the VCD 100. Any number of adjacent loops may be formed, which create a cradle surrounding the VCD 100 and retaining it in a collapsed configuration. FIG. 3C illustrates the looped wire 315 and its alternating series of loops 317, 319 without the VCD 100 for additional clarity. The looped wire 315 is illustrated with arrows showing the path of the loops 317, 319 as they would traverse along the length of a VCD positioned therebetween. In one embodiment, each end of the looped wire 315 passes from a delivery system over a collapsed VCD 100 on the same side of the VCD 100, such that when released, the looped wire 315 does not restrain expansion of the VCD 100 and is retrievable by the delivery system or other means.

With reference to FIG. 3B, the containment mechanism further includes a pull means 320 attached at some point along a release wire 325 between a first side 325a and a second side 325b of the release wire 325. The pull means 320 can be a wire, a string, a thread, a rod, or any other member securable to the release wire 325. The release wire 325 is threaded between the apex of each of the alternating series of loops 317, 319, securing the looped wire 315 around a collapsed VCD 100. Accordingly, when tension is placed on both sides 325a, 325b of the release wire 325, the alternating series of loops 317, 319 are pulled taut against the collapsed VCD 100, maintaining it in a tight, collapsed configuration during delivery. When either or both sides 325a, 325b of the release wire 325 are released, tension on the alternating series of loops 317, 319 is relieved, and the VCD 100 begins to expand. The pull means 320 when pulled retrieves the release wire 325 and completely releases the alternating series of loops 317, 319 of the looped wire 315. In one embodiment, the looped wire 315 is retrievable after releasing the VCD 100.

Figure 3D:
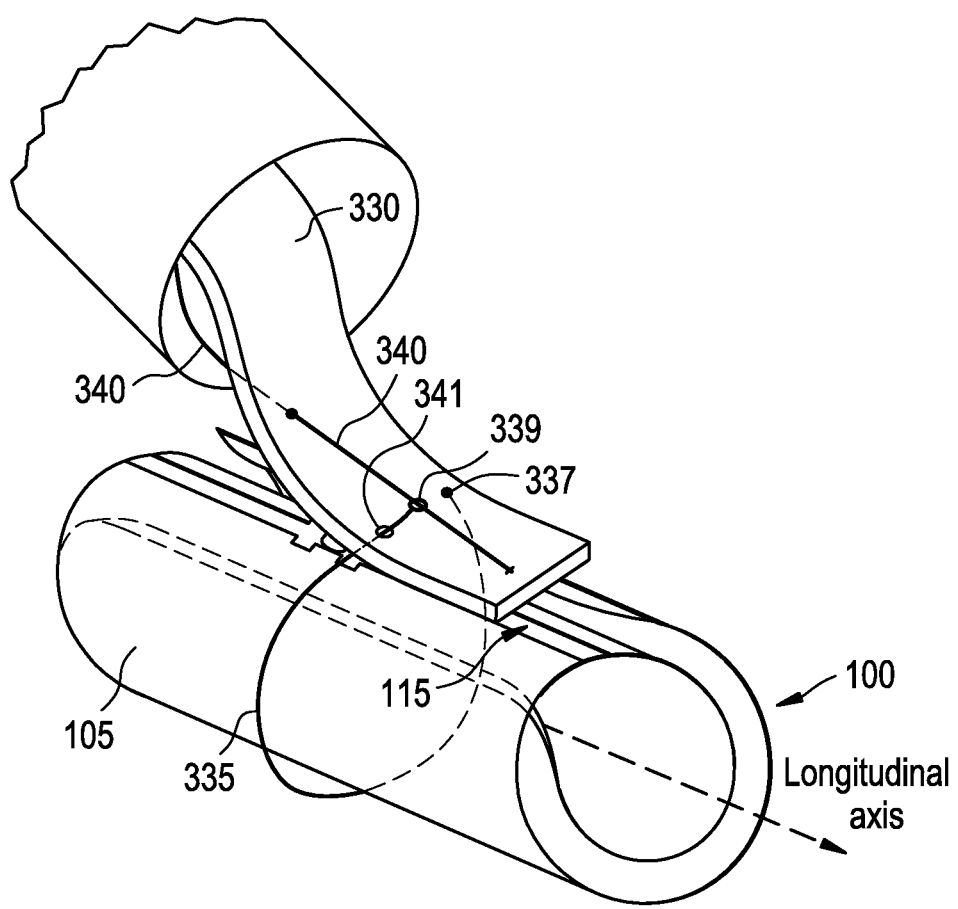

FIG. 3D illustrates another embodiment of a containment mechanism for a VCD 100. According to this embodiment, the containment mechanism includes a loop retainer support 330 adapted to extend from the distal end of a delivery device and a loop 335 having a secured end 337 secured to the loop retainer support 330 and a looped end 339, optionally passing through a hole 341 in the loop retainer support 330, having a loop or other retaining means formed thereby. The containment mechanism further includes a retainer pin 340 adapted for selective actuation during delivery of the VCD 100, which operates to release the looped end 339 from the retainer pen and, thus, freeing the loop 335 from around the VCD 100. As shown, when in secured configuration, the loop 335 is positioned around and maintains the VCD 100 in collapsed (e.g., rolled) configuration. The secured end 337 of the loop 335 is secured by any suitable means to the loop retainer support 330, while the looped end 339 of the loop 335 is releasably threaded over the retainer pin 340. The retainer pin 340 may be moveably secured to the loop retainer support 330 by any suitable means, such as, but not limited to, extending through one or more passages (shown in FIG. 3D), strapped thereto, passing through a channel, and the like, and extend proximally through a channel of the selected delivery device.

In operation, the containment means releases the VCD 100 from its collapsed position by pulling the loop retainer pin 340 in the proximal direction. Any suitable actuating mechanism may be included with the chosen delivery device to allow pulling the loop retainer pin 340. By pulling the loop retainer pin 340 in the proximal direction, the looped end 339 of the loop 335 is released and the VCD 100 is freed and allowed to expand to its stable expanded configuration. Because the loop 335 remains secured to the loop retainer support 330 at its secured end 337, the loop 335 can be removed from the vessel by removing the loop retainer support 330 and/or the delivery device utilized.

According to one embodiment, the loop retainer support 330 is formed from a flexible film having a thickness between approximately 0.05 mm and approximately 5 mm, or between approximately 0.1 mm and approximately 0.5 mm in other embodiments, for example. The width of the loop retainer support 330 may be between approximately 1 mm and approximately 5 mm in one embodiment, or between approximately 2 mm and approximately 4 mm in other embodiments, for example. The loop retainer support 330 may be made from any flexible materials, such as, but not limited to, a polymer (e.g., polytetrafluoroethylene or other fluoropolymer, polyethylene, polyurethane, polyamide, polyimide, PEEK, or any other suitable polymer), or a metal (e.g., Nitinol, stainless steel, cobalt alloys, or any other suitable metal), or any combination thereof. However, other suitable loop retainer support 330 configurations and dimensions can be provided, such as a more rigid member and/or one formed from different suitable materials, such as any other biocompatible material described herein.

According to various embodiments, the loop retainer pin 340 may have a cross-sectional diameter ranging between approximately 0.02 mm and approximately 3 mm, or between approximately 0.05 mm and approximately 0.5 mm in other embodiments. As described, in one embodiment, the loop retainer pin 340 extends through the delivery device and is connected to an actuation mechanism for actuation by an operator, such as, but not limited to, a slider, a push button, a wheel, opposing handles, or any other suitable means for pulling the loop retainer pin 340 in the proximal direction. In other embodiments, the loop retainer pin 340 may have a shorter length, such as between approximately 2 mm and approximately 50 mm, or between approximately 4 mm and approximately 15 mm in other embodiments, and is connected to an actuating mechanism by an intermediary member, such as a string or wire. According to various embodiments, the loop retainer pin 340 is formed from a polymer (e.g., polytetrafluoroethylene or other fluoropolymer, polyethylene, polyurethane, polyamide, polyimide, PEEK, or any other suitable polymer), or a metal (e.g., Nitinol, stainless steel, cobalt alloys, or any other suitable metal), or any combination thereof. Although not shown, the VCD 100 may further include an anchoring tab 120 and/or pull string, such as is illustrated in FIG. 3A, to allow positioning the VCD 100 after released from the loop 335. The containment mechanisms described with reference to FIGS. 3A-3D are provided for illustrative purposes only. Any other suitable means to releasably retain a VCD in a collapsed configuration may be provided. For example, with reference to FIG. 3B, instead of alternating loops, the looped wire 315 may be formed as a spiral around a collapsed VCD along its length and be completely released by pulling one end. As another example, instead of a looped wire 315, a releasable mesh or tubular member may surround at least a portion of the VCD, such that the mesh or tubular member may be opened or otherwise split to free the VCD therefrom. Additional containment mechanisms are also illustrated by and described with reference to the various embodiments of delivery devices described with reference to FIGS. 6-10P.

FIGS. 4A-4J illustrate additional configurations of a VCD each having different shaped sealing membranes and/or support frames. Although the shape and/or configuration of the VCDs of these embodiments differ at least in part from that described with reference to FIGS. 1-2, each may be formed in the same or similar manner and may be collapsed in a rolled configuration for delivery in the same or similar manner.

Figure 4A:
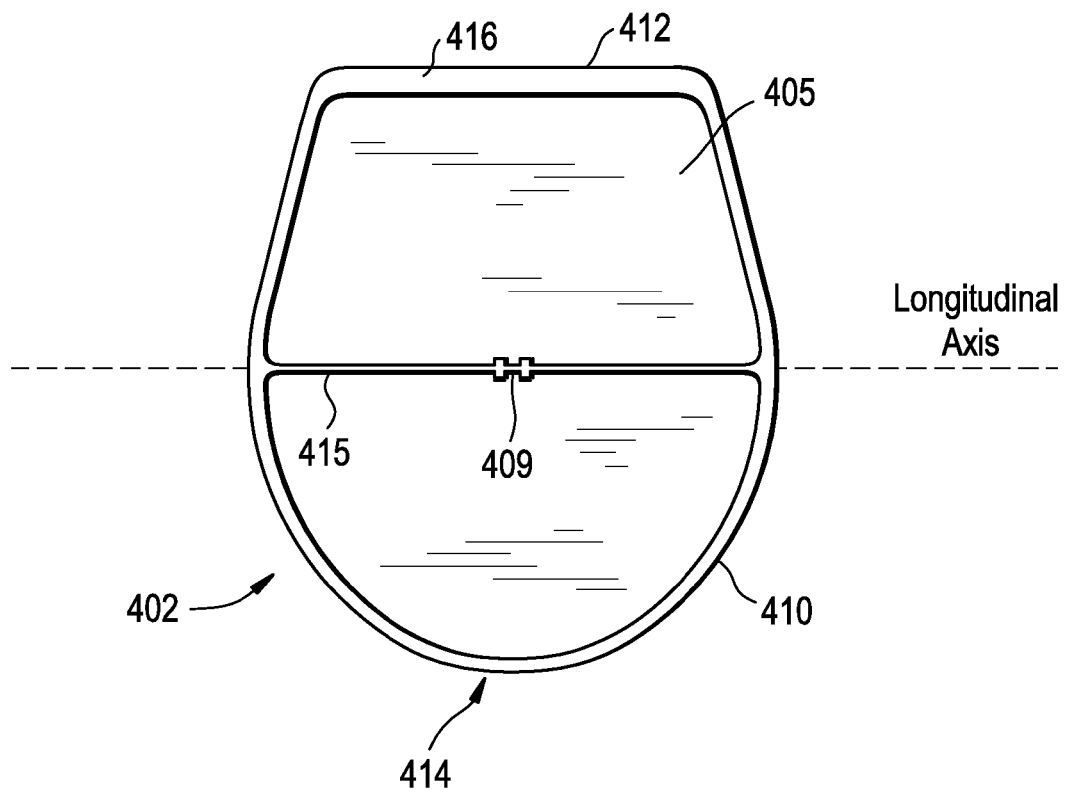
FIGS. 4A-4J are illustrations of VCDs according to some representative embodiments.

FIG. 4A illustrates a VCD 402, according to one embodiment, that includes a sealing membrane 405 that is asymmetrical with respect to at least one axis—the longitudinal axis. In the embodiment illustrated in FIG. 4A, the sealing membrane 405 is shaped with one side having an arcuate edge 414 and the opposite side having a substantially straight edge 412. The peripheral support frame 410 generally follows the same or similar shape of the sealing membrane 405 outer edges, formed in an arcuate shape on one side and a substantially straight shape on the opposite side.

One purpose served by the arcuate edge 414 and opposing straight edge 412 is to prevent flaring of the edges of the sealing membrane 405, such as may occur during delivery when in a collapsed configuration or after implantation. The arcuate edge 414 reduces the surface area of the sealing membrane 405 on at least one side, minimizing the additional drag created by fluid flowing thereover during implantation. In addition, the peripheral support frame 410 along the straight edge 412 may be stiffer and thus more rigid than the support frame along the arcuate edge 414. In the embodiment shown in FIG. 4A, the peripheral support frame 410 has a larger profile 416 (e.g., thicker, wider, or both) along the straight edge 412, which enhances its strength and rigidity. Strength and rigidity of the peripheral support frame 410 may be enhanced along the straight edge 412 in any number of ways, including, but not limited to, increasing the cross-sectional profile of the frame along the straight edge 412 relative to the rest of the peripheral support frame 410, forming the peripheral support frame 410 along the straight edge 412 from a more rigid frame material, reinforcing the peripheral support frame 410 along the straight edge 412 with a more rigid frame material, or any combination thereof.

In addition, providing a stiffer peripheral support frame 410 along the straight edge 412 also serves to reduce flaring when in a collapsed configuration, as shown above in FIG. 3A, because the arcuate edge 414 is rolled underneath and contained by the straight edge 412. Thus, the more rigid peripheral support frame 410 along the straight edge 412 prevents flaring of the other sealing membrane 405 edges when rolled underneath. The portion of the peripheral support frame 410 along the straight edge 412 is chosen as having increased rigidity and strength because the straight shape still allows rolling the relatively less rigid, more flexible portions of the peripheral support frame 410. Otherwise, if the arcuate portion of the peripheral support frame 410 is formed with increased rigidity, then the ability to effectively roll at least the arcuate half of the VCD 402 into a collapsed configuration is inhibited due to the more rigid arcuate portion. Moreover, strengthening the peripheral support frame 410 along the straight edge 412 provides a larger area having increased rigidity and support covering the remaining portion of the VCD 402 rolled thereunder.

Figure 4B:
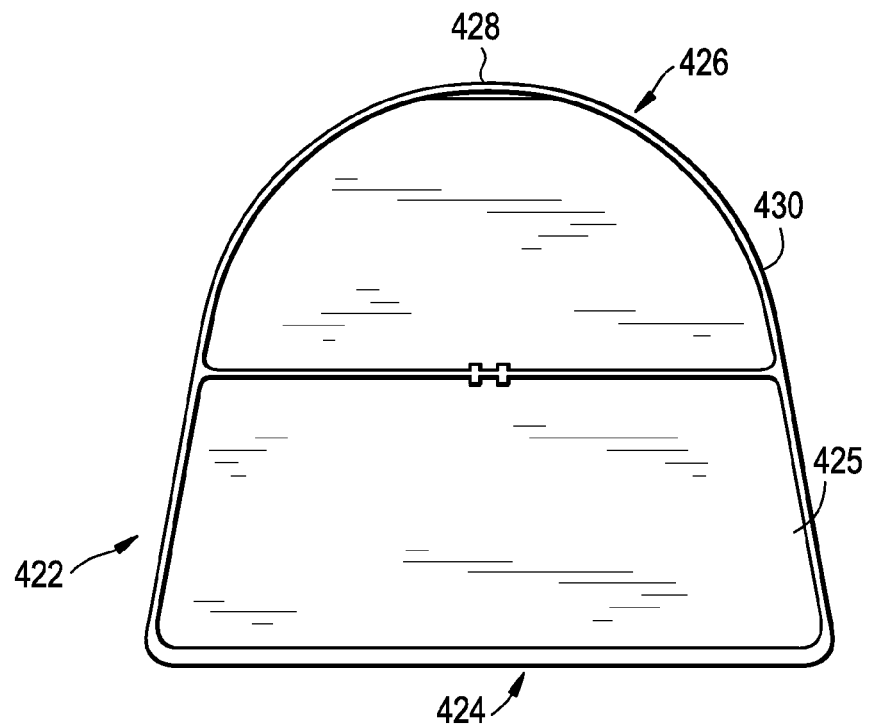

FIG. 4B illustrates another embodiment of a VCD 422 having an asymmetrical shape, which is slightly different than the asymmetrical shape of the VCD 100 shown in FIG. 2. According to this embodiment, the VCD 422 includes a sealing membrane 425 and a peripheral support frame 430 that are both formed to have a substantially straight edge 424 and an opposite arcuate edge 426. Like the VCD 100 described with reference to FIG. 1, the asymmetrical shape and straight edge 424 facilitate maintaining the VCD 422 in its rolled collapsed configuration, especially with a peripheral support frame 430 having increased rigidity along at least a portion of the straight edge 424. In addition, at least one other portion of the peripheral support frame 430 may include a more rigid area for increasing the rigidity and support of the peripheral support frame 430. In this embodiment, a strengthened area 428 is oriented at or near the apex of the arcuate edge 426 and opposite the straight edge 424. Only a portion of the peripheral support frame 430 along the arcuate edge 426 includes a strengthened area 428 to still permit rolling the peripheral support frame 430 along the longitudinal axis.

Figure 4C:
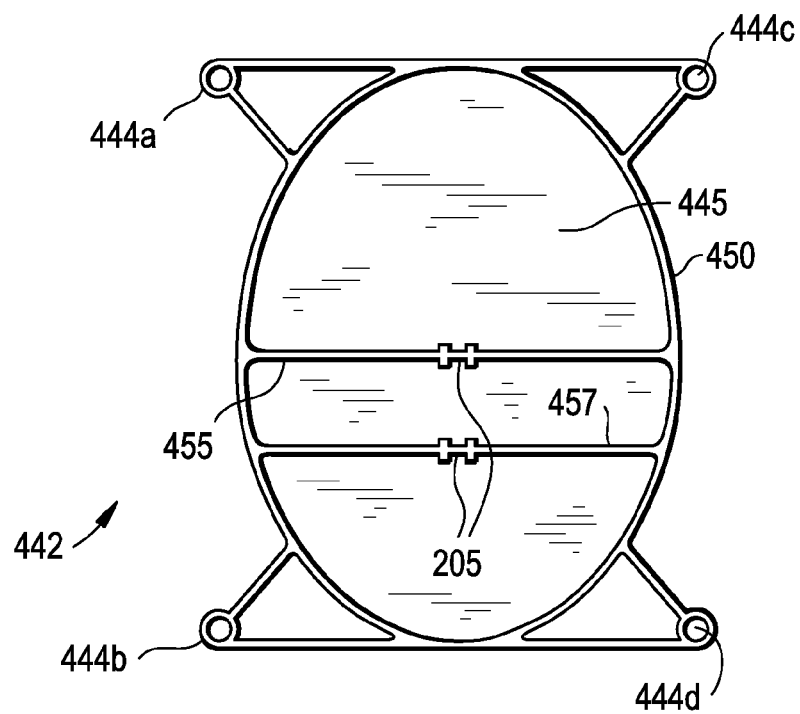

FIG. 4C illustrates a VCD 442 having an elliptical shaped sealing membrane 445. According to this embodiment, the VCD 442 also includes a peripheral support frame 450 that generally follows the elliptical shape of the sealing membrane 445 at or near its outer edge, but also includes at least two apertures or eyes 444 extending therefrom that facilitate containing the VCD 442 in its collapsed configuration. For example, the VCD 442 illustrated in FIG. 4C includes four eyes 444a, 444b, 444c, 444d that extend from opposite portions of the sealing membrane 445 and/or the peripheral support frame 450. When in a collapsed configuration and rolled along the longitudinal axis, opposing pairs of eyes 444a, 444b and 444c, 444d align for receiving a containment mechanism through the eyes to releasably hold the VCD 442 in its rolled collapsed configuration. For example, according to one embodiment, a first release pin can be releasably inserted through the eyes 444a, 444b and a second release pin can be releasably inserted through the eyes 444c, 444d when the VCD 442 is rolled, which will serve to retain the VCD 442 in its rolled configuration. During delivery, each release pin is removed to allow the VCD 442 to expand to its expanded configuration under the force of the peripheral support frame 450 expanding to its natural stable shape.

In other embodiments, instead of a release pin, one or more wires, cords, or string members are provided, such as the containment mechanism 305 described with reference to FIG. 3A, or any other member which may be releasably inserted through opposing pairs of eyes 444. Moreover, a VCD 442 containing one or more pairs of apertures or eyes 444 can be formed in any other shape, such as any of the VCDs described herein or any other suitable shape as desired. Similarly, the one or more pairs of eyes 444 can be incorporated into any other VCD described herein as desired. In another embodiment, the eyes 444 are formed through a portion of the sealing membrane 445 instead of, or in addition to, being formed by a portion of the peripheral support frame 450.

In addition, the VCD 442 in this embodiment includes two cross-member supports 455, 457, similar to the cross-member support 115 shown in FIG. 2, spaced apart and positioned between opposite sides of the peripheral support frame 450. Having two more rigid cross-member supports 455, 457 provides additional longitudinal support across the sealing membrane 445 when in a rolled and expanded configuration.

Moreover, according to this embodiment, a first cross-member support 455 is oriented at or near the latitudinal center of the sealing membrane 445, while a second cross-member support 457 is oriented off-center from the latitudinal center. Having the second cross-member support 457 oriented off-center provides additional support and rigidity to the sealing membrane 445 and further prevents the support frame 450 and/or sealing membrane 445 edges from flaring or otherwise undesirably deforming when in a rolled or collapsed configuration. Any of the VCD embodiments described herein may optionally include more than one cross-member support, any of which may be centered or off-center. Similarly, the attachment means 205 may be oriented off-center along the longitudinal axis to allow for more effective centering of the VCD 100 along the longitudinal axis.

Figure 4D:
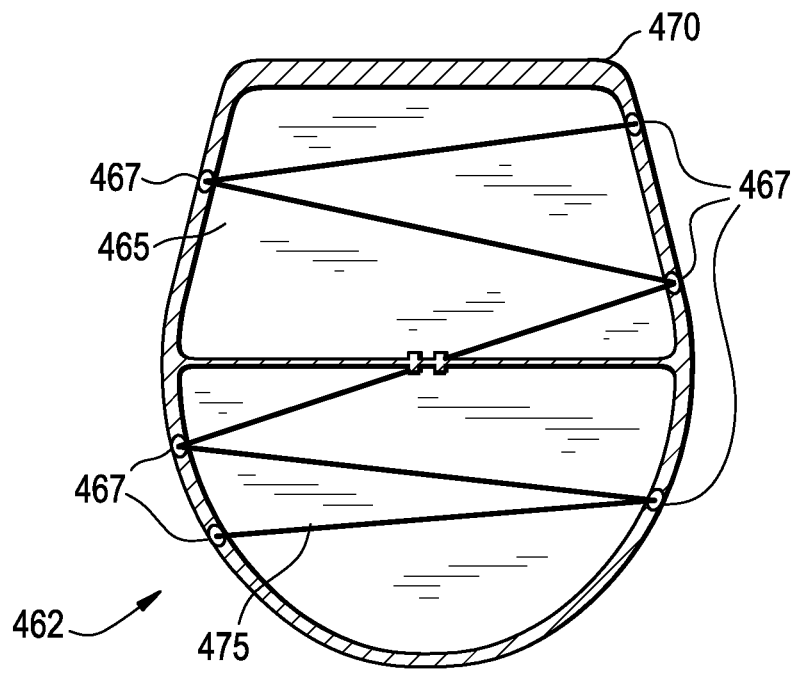

FIG. 4D illustrates a VCD 462 incorporating a different stiffening and support means. Here, the VCD 462 includes a peripheral support frame 470 and at least one support wire 475 threaded through multiple eyes 467 formed along the periphery of the VCD 462 on opposite sides. The eyes 467 may be formed through the peripheral support frame 470 and/or through the sealing membrane 465, both of which are formed and configured in the same or similar manner as described with reference to other embodiments herein. The support wire 475 provides additional support across the sealing membrane 465 between the peripheral support frame 470. In the illustrated embodiment, the support wire 475 is threaded through the eyes 467 in a back-and-forth configuration, much like lacing the two opposite sides of the VCD 462. The support wire 475 may be formed from any suitable biocompatible, metal, metal alloy, polymer, or any other suitable material, such as described above with reference to FIG. 2. The support wire 475 may be completely biodegradable, partially biodegradable, or not degradable, absorbable, or erodable, according to various embodiments. The support wire 475 may be loose and separate from the sealing membrane 465, or may be taut and/or affixed to the sealing membrane 465, either on the underneath side of the sealing membrane 465 facing inward toward the vessel interior or on the upper side of the sealing membrane 465 facing toward the vessel wall. Otherwise, similar to the fabrication techniques described with reference to FIG. 2, the support wire 475 may be more integrated with the sealing membrane 465 and the peripheral support frame 470, such as being sandwiched between two membrane layers. The support wire 475 and eyes 467 may be adapted for use with any VCD embodiment described herein.

Figure 4E:
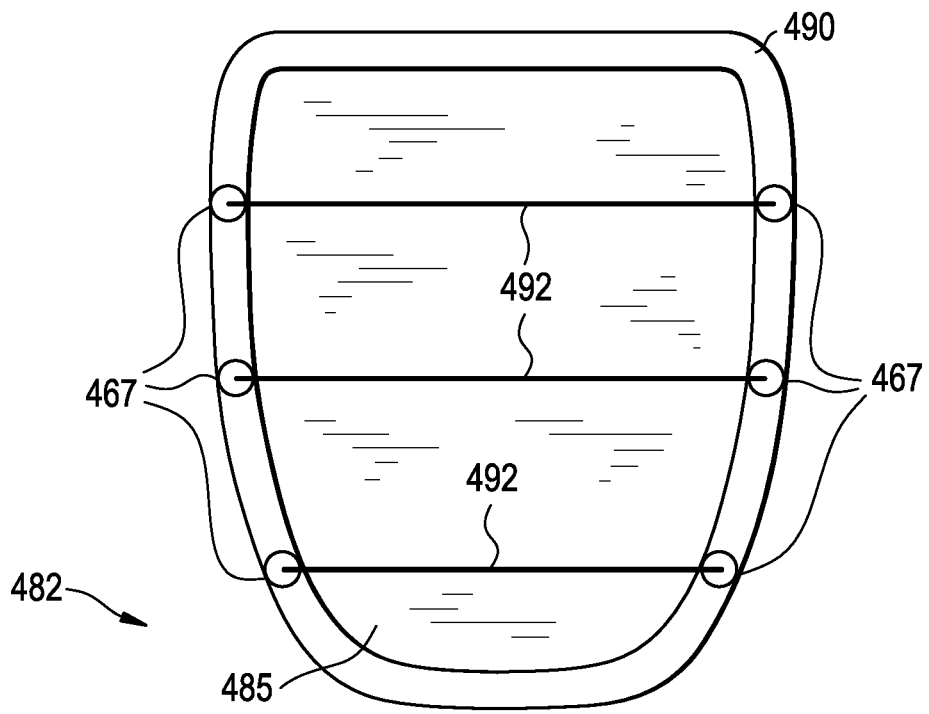

FIG. 4E illustrates a similar VCD 482, which includes multiple support wires 492. According to this embodiment, each support wire 492 is separately threaded through a pair of opposite eyes 467 or otherwise secured to the peripheral support frame 490 laterally. Having multiple support wires 492 spaced apart and positioned in a substantially lateral orientation improves the ability to roll the VCD 482 into a collapsed configuration along the longitudinal axis, while still providing additional support for the sealing membrane 485 stretched between the peripheral support frame 490.

Figure 4F:
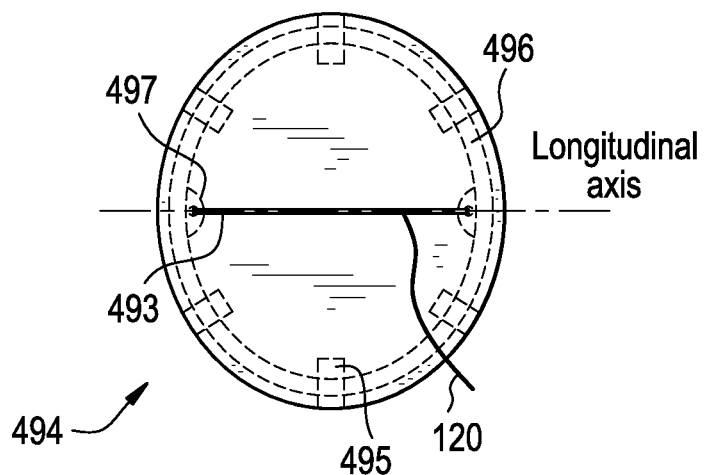
Figure 4G:
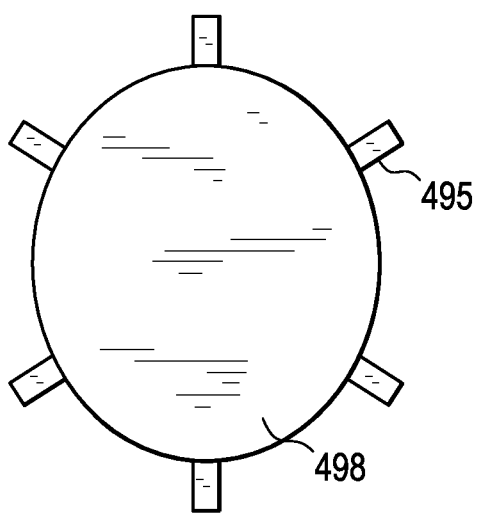
Figure 4H:
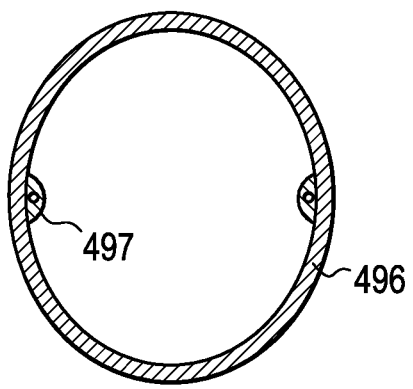

FIGS. 4F-4H illustrate another embodiment of a VCD 494 that includes a circular or elliptical sealing membrane 498 coupled to a circular or elliptical peripheral support frame 496. FIG. 4F illustrates an assembled VCD 494 having the sealing membrane 498 attached to the peripheral support frame 496. FIGS. 4G and 4H separately illustrate the sealing membrane 498 and the peripheral support frame 496, respectively. According to this embodiment, the sealing membrane 498 is coupled to the peripheral support frame 496 at one or more locations along its periphery.

As described herein, it is advantageous for the sealing membrane to conform to the inner vessel shape and to cover the vessel puncture site to facilitate hemostasis. According to various methods, conforming the sealing membrane to the vessel shape may be aided by the natural elasticity and/or deformability of the sealing membrane material, by any excess sealing membrane material relative to the peripheral support frame that allows variability in the membrane surface shape, and/or by multiple attachment points intermittently attaching the sealing membrane to the support frame to allow movement of the membrane relative thereto, such as provided according to this embodiment.

As shown by FIG. 4G, the sealing membrane 498 may be cut or formed with at least two tabs 495 extending from the membrane its periphery. In the embodiment shown, six tabs 495 are provided; however, any number of tabs may be provided in other embodiments. The tabs 495 are configured to encircle or otherwise attach to a respective portion of the support frame 496. For example, each tab 495 is configured to loop around (or at least partially around) the support frame 496, such as by a loop member or a hook member. According to one embodiment, each tab 495 is integral with the sealing membrane 498, and not separately attached to the sealing membrane 498. However, in other embodiments, the sealing membrane 498 may first be formed and then each tab 495 separately attached thereto.

In one embodiment, the sealing membrane 498 is coupled to the support frame 496, such that the membrane 498 is positioned over the vessel facing surface of the support frame 496, positioning the sealing membrane 498 between the inner vessel wall and the support frame 496 upon implantation. In one embodiment, the tabs 495 are folded around the top of the support frame 496 and affixed to the sealing membrane 498 bottom surface (e.g., the surface facing away from the vessel wall upon implantation). Fixation of the tabs 495 to the sealing membrane 498 surface may be accomplished using, but not limited to, glue, solvent, heat, ultrasonic welding, or any other means to affix polymer surfaces. In various embodiments, the sealing membrane 498 can be coupled to the support frame 496 by tabs 495 at any number of locations, such as any number greater than two locations. For example, in various embodiments, two to twelve tabs 495 are used, or two to six tabs 495 are used.

According to one embodiment, all or some of the tabs 495 and the coupling means allow a small amount of relative movement between the sealing membrane 498 and the support frame 496. Movement may serve to reduce the strain on the sealing membrane 498, while also allowing the membrane 498 to conform to the vessel wall shape at or near a vessel puncture site to promote hemostasis. Moreover, in circumstances when vessel re-access is desired at the same puncture site, sliding attachment tabs 495 will allow continued support of the sealing membrane 498 by the support frame 496 while the membrane 498 is punctured, minimizing the portion of the sealing membrane 498 entering the vessel and possibly blocking the blood flow during the subsequent procedure. According to various embodiments, the range of relative movement between the sealing membrane 498 and the support frame 496 may vary between approximately 0.1 mm to approximately 5 mm, for example.

According to one embodiment, the sealing membrane 498 is also coupled to the support frame 496 near the longitudinal axis (e.g., in proximity to the support member 493 connecting means 497, described below). In one embodiment, the sealing membrane 498 is attached to the support frame 496 only at or near the longitudinal axis, which allows the sealing membrane 498 to otherwise move independently of the support frame 496, subject to the radial force applied by the support frame 496 against the vessel wall. In embodiments in which the sealing membrane 498 is only connected to the support frame 496 at or near the longitudinal axis, the sealing membrane 498 may be shaped and sized to have the same or larger dimension than the support frame 496. For example, the sealing member may be up to approximately 6 mm greater, or even larger, in some embodiments. In another embodiment, the sealing membrane 498 is attached to the support frame 496 at or near the longitudinal axis and at one or more other locations along the support frame 496.

According to one embodiment, as illustrated, the peripheral support frame 496 does not include an integrated cross-member support, such as a cross-member support 115 described herein with respect to other embodiments. However, in one embodiment, such as is illustrated by FIGS. 4F-4H, the peripheral support frame 496 includes connecting means 497 for connecting a support member 493 across a portion of the peripheral support frame 496. The support member 493 may therefore be permanently or removably attached to the support frame 496 by the connecting means 497. According to various embodiments, the connecting means 497 may include, but are not limited to, eyes, hooks, tabs, pressure- or friction-fit slots, and the like. According to various embodiments, the support member 493 may be a wire or string formed from pliable or rigid materials, such as, but not limited to, any polymers (biodegradable or non-biodegradable), metals, alloys, or combinations thereof, as are described herein. In other embodiments, however, a cross-member support, such as a cross-member support 115 described with reference to FIGS. 1-2, may be included with the support frame 496, as desired.

Also, as shown in FIG. 4F, the VCD 494 may further include an anchoring tab 120 and/or pull string, which may be connected to the support frame 496, the support member 493, and/or a cross-member support, depending upon the VCD 494 configuration. As described herein, the anchoring tab 120 and/or pull string may be constructed from biodegradable materials or non-biodegradable materials.

It is appreciated that the features of a sealing membrane coupled to a support frame described with reference to the embodiment of FIGS. 4F-4H may be applied to any other VCD embodiment described herein.

Figure 4I:
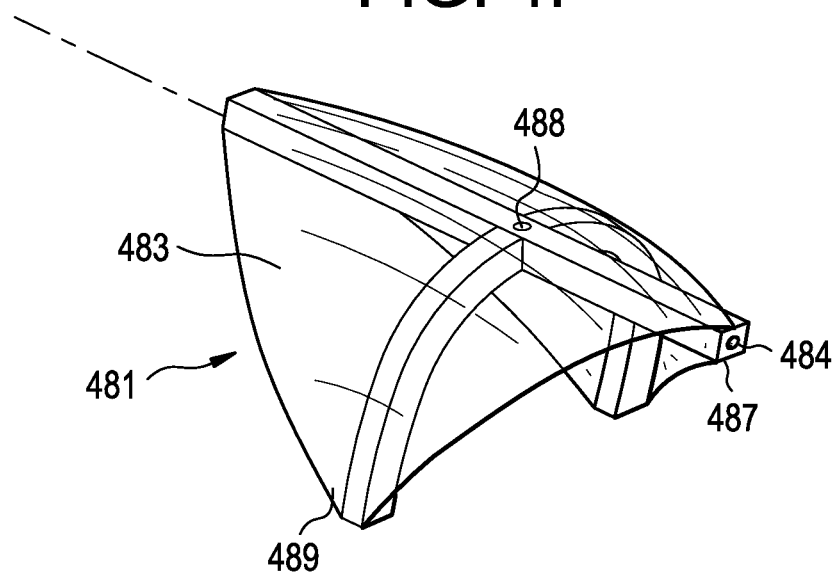
Figure 4J:
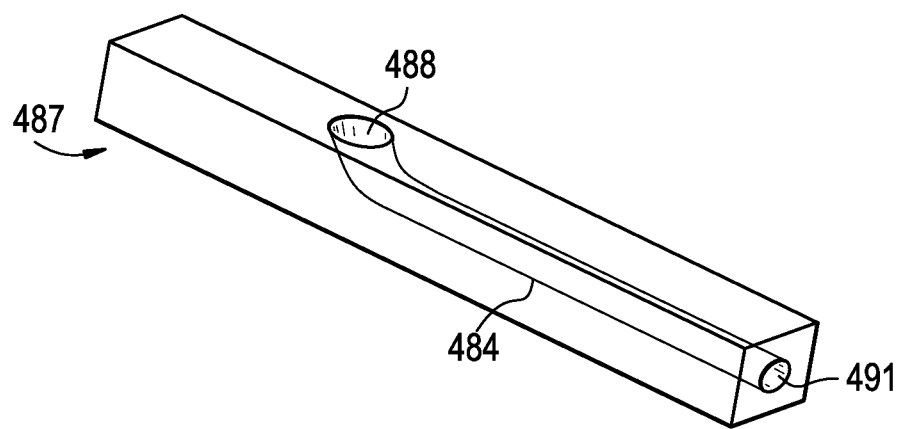

FIGS. 4I-4J illustrate another embodiment of a VCD 481 that includes a sealing membrane 483, a support frame 489, and a cross-member support 487. In this embodiment, the support frame 489 consists of a single member oriented approximately perpendicular to the longitudinal axis, such that when expanding, the support frame will expand radially or along the circumference of the vessel in which it is positioned. The support frame 489 may be formed from any biodegradable or non-absorbable materials, such as those described with reference to FIG. 2. In one embodiment, the support frame 489 is pre-shaped to a desired shape and curvature utilizing a shape memory metal or metal alloy, such as nickel-titanium alloy (e.g., Nitinol), a shape memory polymer, or any combination thereof. For example, according to one embodiment, support frames 489 is pre-shaped to expand to a have a slightly larger radius of curvature than the radius of curvature of the vessel into which the VCD 481 is to be implanted.

The sealing membrane 483 of this embodiment is formed in a quadrilateral geometry (e.g., square, rectangle, diamond, etc.) with two opposing corners being oriented at respective ends of the support frame 489 and the other two opposing corners being oriented at respective ends of the cross-member support 487. The quadrilateral geometry reduces flaring or deformation of the sealing membrane 483 along its edges. The sealing membrane 483 may be constructed of any biodegradable or non-absorbable materials, or a combination thereof, such as those described with reference to FIG. 2.

According to one embodiment, the cross-member support 487 differs from other cross-member supports described herein by including a guide channel 484 passing therethrough. The guide channel 484 is sized and configured to allow one or more guide wires to pass therethrough, which are used to facilitate delivery and placement of the VCD 481 using conventional guide wire techniques and/or to preserve access for the guide wire after VCD deployment. As illustrated in FIGS. 4I-4J, according to one embodiment, the guide channel 484 is formed with a curve, having a point of entry 491 through one end and exiting the cross-member support 487 at some intermediate location 488. FIG. 4J illustrates the cross-member support 487 without the sealing membrane 483 or the support frame 489 integrated therewith. When integrated or otherwise affixed to the sealing membrane 483, the cross-member support 487 may be oriented such that the intermediate exit faces away from the sealing membrane 483. In another embodiment, however, a hole is formed through the sealing membrane to allow a guide wire to exit the guide channel 484 and pass through the sealing membrane 483. In some embodiments, an anchoring tab or pull string may also pass through the this same exit point through the sealing membrane 483, to allow further sealing the exit point 488 formed in the sealing membrane 483. In embodiments including a curved guide channel 484, the curve may be formed gradually, so as to facilitate passage of a guide wire therethrough. Moreover, in one embodiment, at least the entry 491, and optionally the exit 488, of the guide channel 484 is formed in a conical shape or a wider shape to facilitate inserting a guide wire therethrough.

A guidewire may be utilized to facilitate advancing and positioning the VCD within a vessel or other lumen. According to some embodiments, a guidewire may be removed after delivering and prior to releasing the containment means. In other embodiments, a guidewire may be removed after the VCD is in position and its performance is observed. A guidewire, thus, eases subsequent access within the vessel, such as may be performed in the case of a VCD malfunction, failure, or other reason calling for the removal of a delivered VCD. Upon removal of an initial VCD, a replacement VCD may be delivered over the guidewire. Moreover, a guidewire further facilitates introducing additional means to prevent and/or reduce bleeding from an un-sealed puncture, such as may be useful during replacement or repositioning of a VCD prior to sealing the puncture.

It is appreciated that any of the VCD embodiments described or illustrated herein may be delivered utilizing one or more guidewires in a same or similar manner as described with reference to FIGS. 4I-4J. In embodiments in which a support structure does not include a guide channel, such as the guide channel described with reference to FIGS. 4I-4J, then a guidewire may be passed through an interior space defined by a VCD in its collapsed configuration, such that the VCD is effectively rolled over the guidewire and the guidewire oriented along or parallel to its longitudinal axis. In other embodiments, a VCD may include an additional channel or aperture through which a guidewire may be passed, orienting the guidewire along or parallel to the VCDs longitudinal axis when in a collapsed or rolled configuration. In yet other embodiments, a guidewire may be positioned with and/or coupled to one or more other components of the VCD delivery means, such as a loop retainer support described and illustrated with reference to FIG. 3D, for example.

According to various embodiments, the cross-member support 487 has a length between approximately 3 mm to approximately 50 mm, and between approximately 4 mm to approximately 20 mm in one embodiment. The thickness or width of the cross-member support 487 may range between approximately 0.5 mm and approximately 3 mm, and between approximately 1 mm to approximately 2 mm in one embodiment. In other embodiments, instead of a square or rectangular cross section as illustrated in FIG. 4F, the cross-member support 487 may have an approximately circular cross section, or any other cross section profile, as desired. In addition, the guide channel 484 of a cross-member support 487 may have an inner diameter large enough to accommodate guide wires ranging from approximately 0.1 mm to approximately 1.1 mm in diameter. The guide channel 484 may be formed larger or smaller to accommodate guide wires having other dimensions, as desired, which may depend upon the procedure being performed and/or the patient's anatomy. According to various embodiments, the cross-member support 487 may be constructed of any biodegradable or non-absorbable materials, or a combination thereof, such as those described with reference to FIG. 2.

The VCD 481 of this embodiment therefore provides an advantageous configuration by including a limited number of non-biodegradable or non-absorbable components having a minimized size relative to other embodiments described herein, such as only the cross-member support 487 and/or the single member forming the support frame 489. The reduced number and size of support components also allows the VCD 495 to be rolled or otherwise compressed into a collapsed configuration that may ultimately be smaller than other embodiments described herein, and thus capable for delivery through smaller punctures and/or utilizing smaller delivery systems.

It is appreciated that any of the features described with reference to the additional example VCD embodiments of FIGS. 4A-4J may be incorporated with any other VCD embodiment described and/or illustrated herein. Moreover, according to various embodiments, any or all of the components of the peripheral support frame may be fabricated from at least partially biodegradable materials, such as those described by example with reference to FIG. 2, allowing most, if not all of the VCD to degrade over time after implantation. However, in other embodiments, the peripheral support frame and/or other components of the VCD may be constructed from materials that are not biodegradable, such as those described with reference to FIG. 2, resulting in at least a portion of the VCD components remaining within the vessel after implantation. Furthermore, the general shape, orientation, and/or composition of the VCDs and components described herein are illustrative and are not intended to be limiting.

Figure 5A:
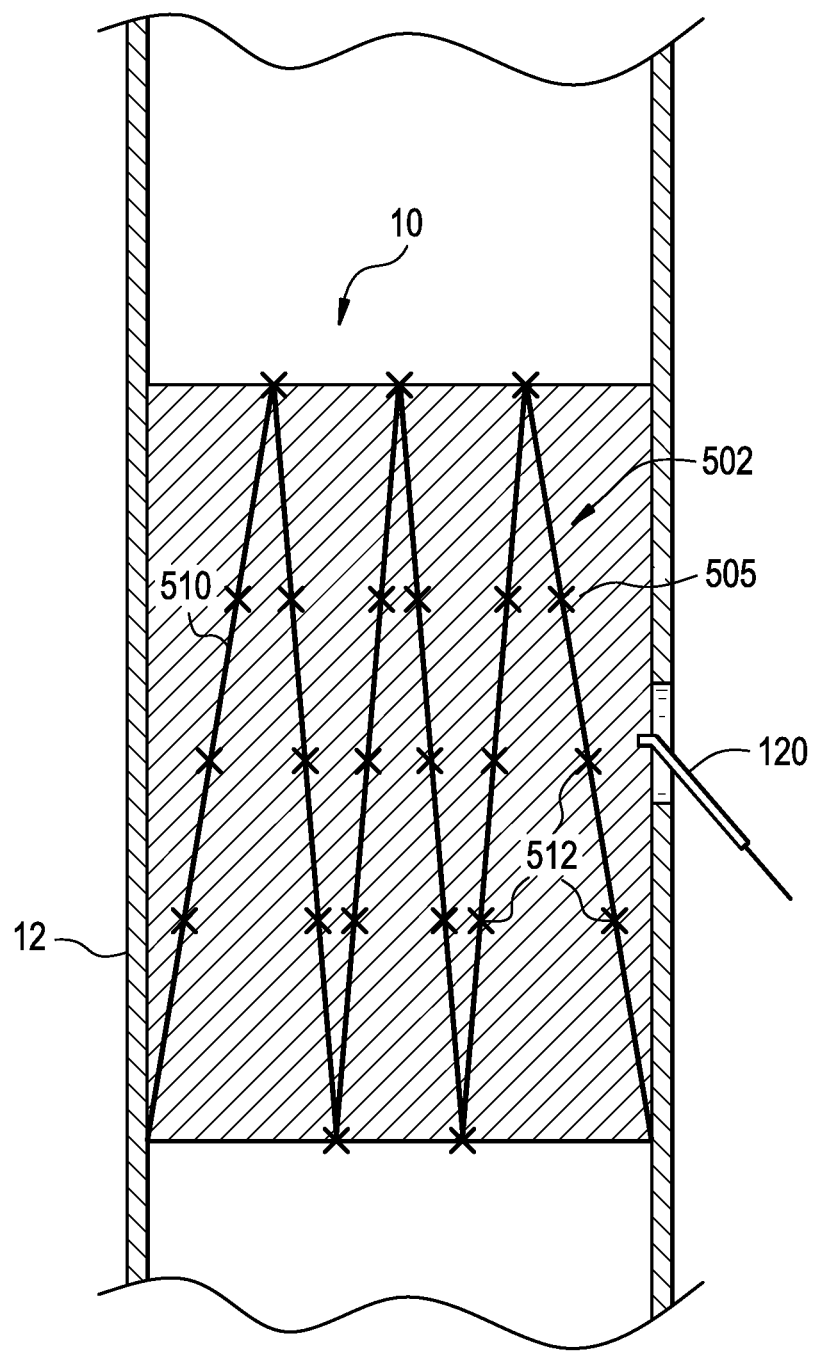
FIGS. 5A-5G are illustrations of additional VCDs according to some representative embodiments.

FIGS. 5A-5G illustrate other embodiments of a VCD, each having a different means for retaining the VCD within a vessel. FIG. 5A illustrates a VCD 502 having a radially expandable support frame 510 with a back-and-forth configuration (e.g., accordion-like) integrated or otherwise affixed to a sealing membrane 505. In one embodiment, the support frame 510 is formed having a tubular shape, and the sealing membrane 505 is also formed in a similarly dimensioned tubular shape, such that when expanded, the support frame 510 expands the sealing membrane 505 radially in all directions within a vessel 10. When in a collapsed configuration, the support frame 510 has a first circumference that is smaller than the inner circumference of the vessel wall 12 to allow delivery through a delivery system having a small channel diameter. The support frame 510 then expands to the expanded configuration, having a second circumference greater than the first circumference, which is either the same or slightly larger than the inner circumference of the vessel wall 12. Accordingly, when the VCD 502 is expanded within the vessel 10, the support frame 510 applies a low radial pressure to the interior of the vessel wall 12 as a result of its similar or larger circumference.

The sealing membrane 505 may be constructed at least partially from biodegradable materials, or may be constructed from non-absorbable materials, such as any of those materials described by example with reference to FIG. 2. In addition, at least a portion of the support frame 510 may be pre-shaped to a desired shape and curvature utilizing a shape memory metal or metal alloy, such as nickel-titanium alloy (e.g., Nitinol), a shape memory polymer, or any combination thereof.

In one embodiment, the sealing membrane 505 is connected to the support frame 510 at one or multiple attachment points 512, either on the underneath side of the sealing membrane 505 facing inward toward the vessel 10 interior or on the upper side of the sealing membrane 505 facing toward the vessel wall 12. In the embodiment shown in FIG. 5A, the attachment points 512 are spaced apart and dispersed along the entire sealing membrane 505 and/or the support frame 510. However, in other embodiments, there may be fewer attachment points 512, which may be focused in a specific area of the VCD 502, such as at or near the center of the sealing membrane 505, along the edges of the sealing membrane 505, or a combination thereof. The attachment points 512 between the sealing membrane 505 and support frame 510 may be accomplished by any suitable means, including, but not limited to, sutures, adhesives, heat sealing, interweaving the support frame 510 and the sealing membrane 505, mechanically affixing, or any other similar methods. In other embodiments, the support frame 510 may be more integrated with the sealing membrane 505, fabricated in a manner similar to the fabrication techniques described with reference to FIG. 2, such as being sandwiched between two membrane layers.

According to this embodiment, the VCD 502 also optionally includes an anchoring tab 120 for passing through the puncture site 15 and securing to the patient's tissue to facilitate securing the VCD 502 in place, such as is described with reference to FIG. 2.

Figure 5B:
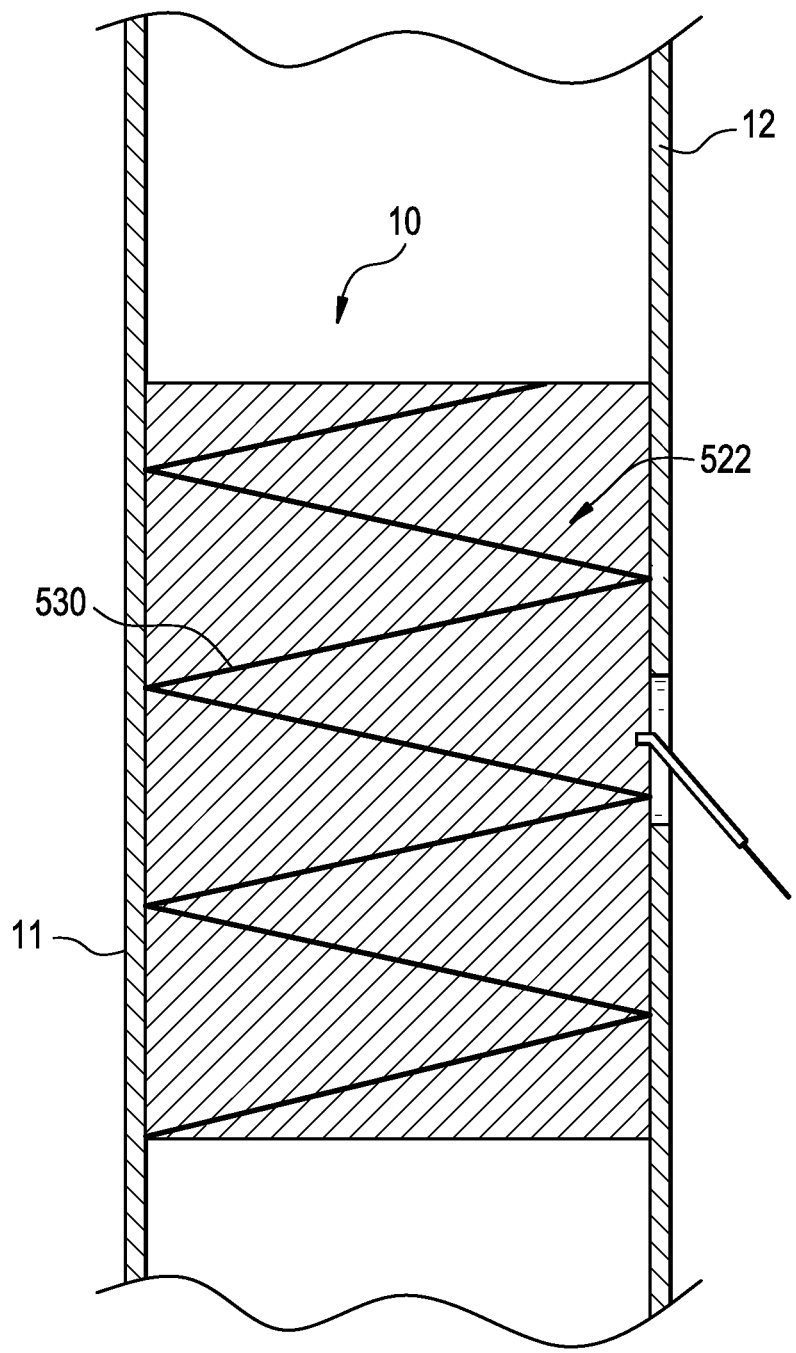

FIG. 5B illustrates yet another embodiment of a VCD 522 having a support frame 530 formed in a substantially coiled or helical shape, whereby successive coils run longitudinally through the vessel 10. As with other embodiments described herein, the support frame 530 can be constructed at least partially from biodegradable materials, or may be constructed from non-absorbable materials, such as any of those materials described by example with reference to FIG. 2. In addition, at least a portion of the support frame 530 may be pre-shaped to a desired shape and curvature utilizing a shape memory metal or metal alloy, such as nickel-titanium alloy (e.g., Nitinol), a shape memory polymer, or any combination thereof.

Figure 5C:
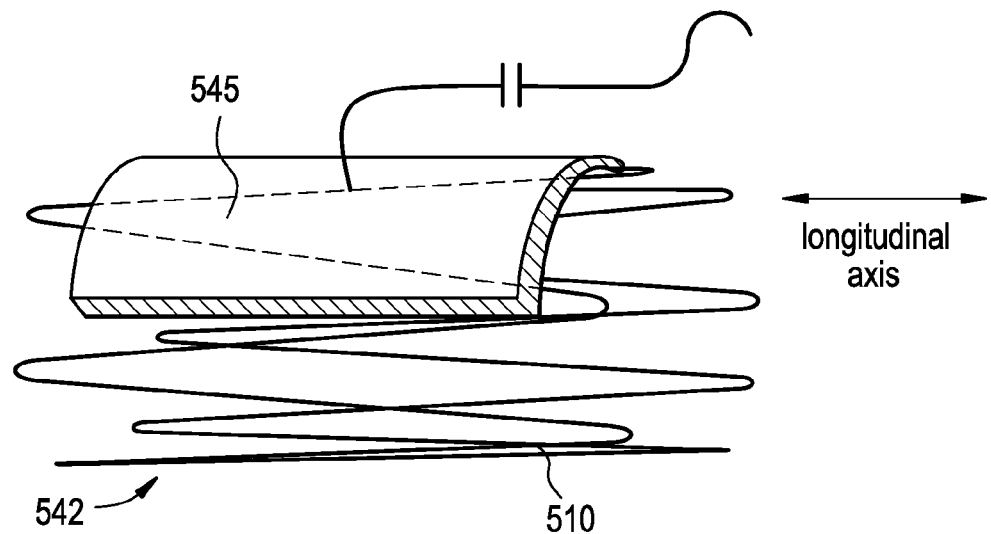

FIG. 5C illustrates another embodiment of a VCD 542 having a radially expanding back-and-forth support frame 510, as described with reference to FIG. 5A. In this embodiment, the sealing membrane 545 only partially covers the support frame 510. The sealing membrane 545 is sized and affixed to, or otherwise integrated with, the support frame 510 to permit positioning the sealing membrane 545 at or near a puncture site within a vessel and to at least partially cover the puncture site to facilitate hemostasis. While the support frame 510 shows a single element formed in a back-and-forth configuration, the support frame 510 in other embodiments may be configured with multiple woven elements in a back-and-forth configuration, such as in a "Chinese handcuff" configuration, as utilized in many woven, self-expanding stent devices. FIG. 5F illustrates an example embodiment in which the support frame is configured in a woven manner.

Figure 5D:
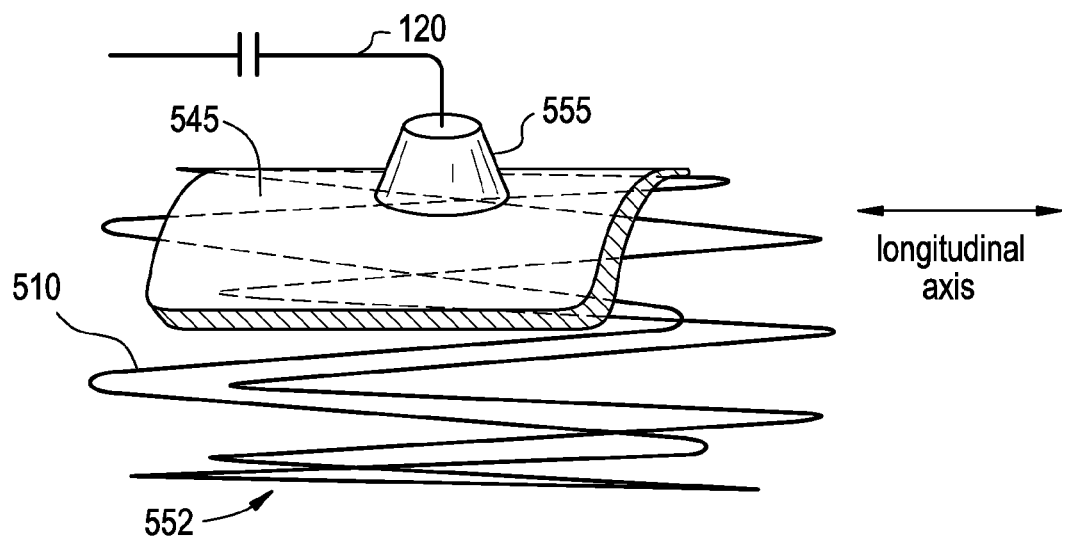

FIG. 5D illustrates another embodiment of a VCD 552 configured in a manner similar to that described with reference to FIG. 5A or 5C, but including a protrusion 555 extending from the support frame 510, the sealing membrane 545, and/or the anchoring tab 120. The protrusion 555 may extend from the approximate center or from any other position along the VCD 552. By positioning the protrusion 555 proximate to the puncture site, the protrusion 555 facilitates anchoring the VCD 552 in place and at least partially sealing a puncture site by extending into the puncture. According to one embodiment, the protrusion 555 also locally elutes or otherwise releases one or more chemical components for controlling biological processes, such as is described with reference to FIG. 2. According to various embodiments, a protrusion 555 may be formed in a conical, frustoconical, pyramidal, frustopyramidal, or other cross-sectional geometry. In one embodiment, the protrusion 555 is integrated with, or otherwise adapted to, the support frame 510.

According to one embodiment, the protrusion 555 is formed from multiple wire elements, such as braided or twisted wires, which provide structural support and at least partial rigidity to the protrusion 555. The wire elements may be formed from any biocompatible material, such as those described with reference to FIG. 2. In one embodiment, the wire elements of the protrusion 555 are spaced close enough together to promote hemostasis without requiring an additional sealing membrane, whereby the wire elements serve to seal the puncture site. In one embodiment, the spacing and/or the configuration of the wire elements forming the protrusion 555 creates a different density or shape than that of other portions of the support frame 510, permitting the protrusion 555 to serve additional or different functions than the support frame 510. For example, in one embodiment, the wire elements forming the protrusion 555, and optionally portions of the support frame 510, are spaced in a more dense configuration proximate to the vessel's puncture site to improve the ability to promote hemostasis without a sealing membrane placed thereover.

In another embodiment, however, the protrusion 555 is at least partially covered by a sealing membrane 545. The sealing membrane 545 may cover some or all of the support frame 510 in addition to the protrusion 555, or only cover the protrusion 555. In another embodiment, instead of, or in addition to, the protrusion 555 being formed from an underlying structure, the protrusion 555 may be formed from excess membrane material, which may be the same or different material forming the sealing membrane 545.

Figure 5E:
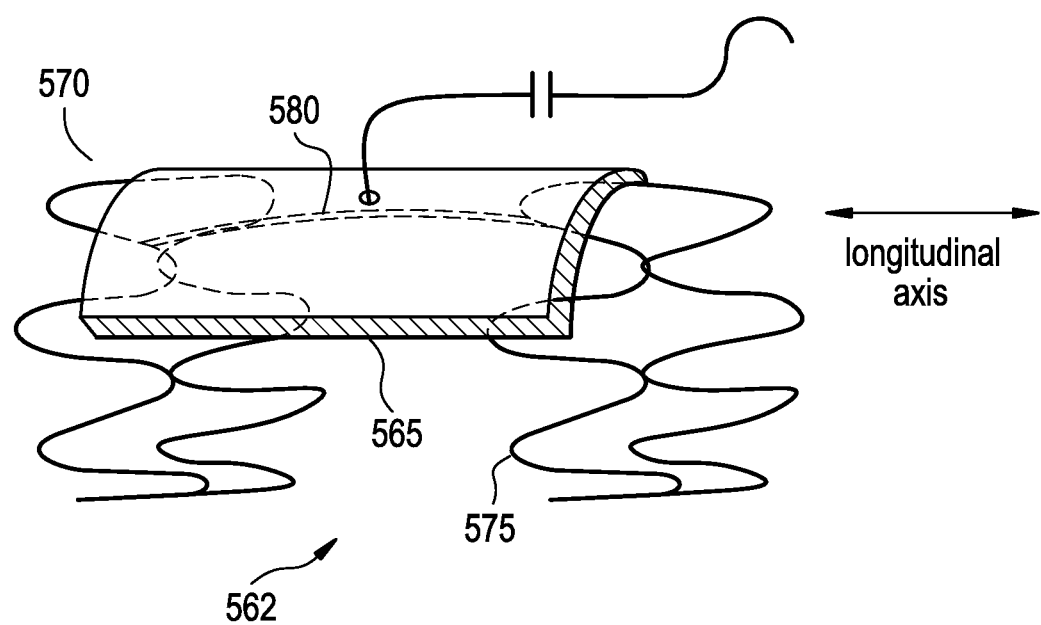
Figure 5F:
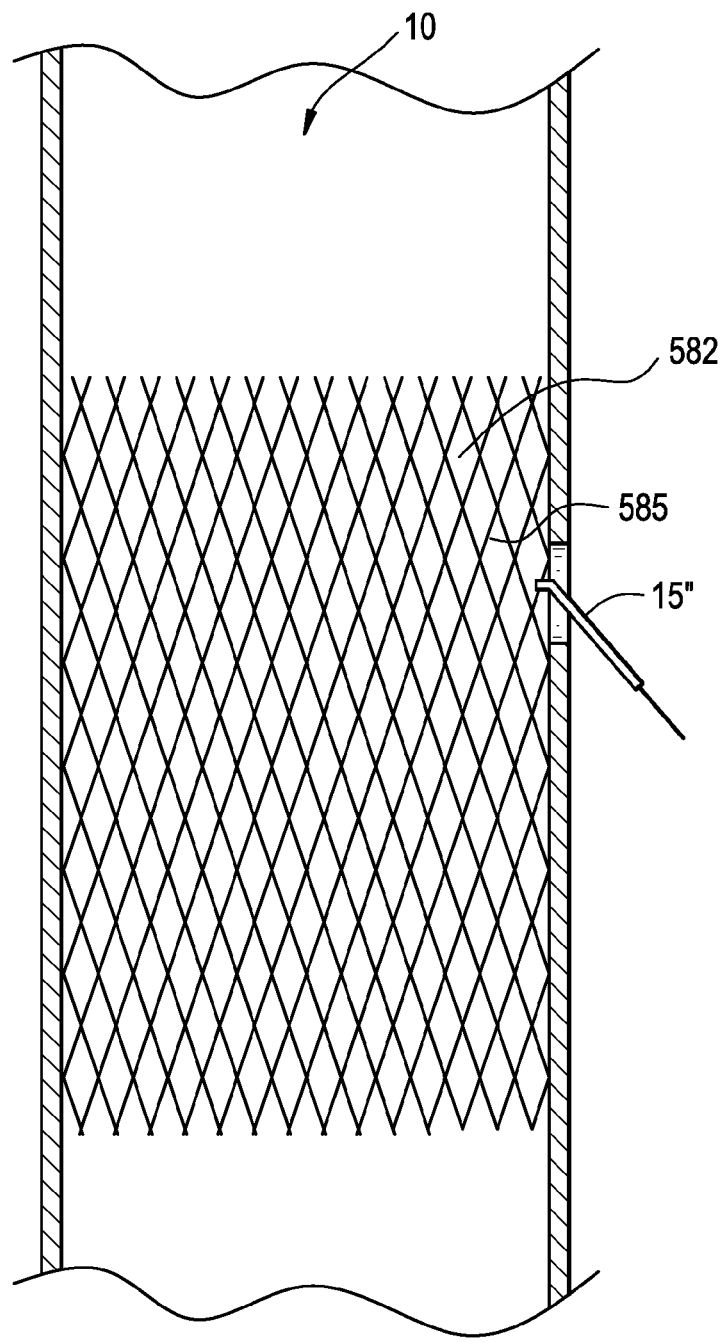

FIG. 5E illustrates another embodiment of a VCD. The VCD according to this embodiment is an articulated VCD 562 having an articulated support frame including a first radial support frame 570 portion and a second radial support frame 575 portion. Each radial support frame 570, 575 is configured in a manner similar to the support frame 510 described with reference to FIGS. 5A, 5C, and 5D. However, in this embodiment, each radial support frame 570, 575 is narrower in width (e.g., shorter along the longitudinal access) and spaced apart along the longitudinal axis to permit positioning on opposite sides of a punctures site upon implantation. In one embodiment, the two radial support frames 570, 575 are connected by at least one joint 580 and/or a sealing membrane 565 extending therebetween. As further described below with reference to FIGS. 10J-10M, an articulated VCD 562 having two support frames 570, 575 allows for additional loading and delivery techniques.

According to one embodiment, a sealing membrane 565 covers at least part of the support frames 570, 575 and/or at least part of the joint 580. The sealing membrane 565, the two radial support frames 570, 575, and/or the joint 580 may be fabricated from any biodegradable or non-absorbable material, or any combinations thereof, such as those described with reference to FIG. 2. In addition, the two radial support frames 570, 575 and/or the joint 580 may be pre-shaped to a desired shape and curvature utilizing a shape memory metal or metal alloy, such as nickel-titanium alloy (e.g., Nitinol), a shape memory polymer, or any combination thereof. For example, according to one embodiment, each of the radial support frames 570, 575 are pre-shaped to expand radially to a slightly larger diameter and circumference than the inner diameter and circumference of the vessel into which the articulated VCD 562 is to be implanted, while the joint 580 is pre-shaped to expand longitudinally from a crimped or folded position during delivery to space apart and position each of the radial support frames 570, 575.

According to various embodiments, the overall dimensions of an articulated VCD 562 may be the same or similar to that described with reference to FIG. 2. The width (in the longitudinal direction) of each radial support frame 570, 575 may range between approximately 2 mm to approximately 12 mm. The radial support frames 570, 575 may have substantially the same or similar width, or they may have different widths. Similar to that described with reference to FIG. 2, the articulated VCD 562 may collapse to a collapsed configuration capable of delivering via a delivery device having a sheath size ranging from a 4 Fr sheath size to a 27 Fr sheath size, for example.

FIG. 5F illustrates another embodiment of a VCD. According to this embodiment, the VCD 582 is formed from a support frame 585 that is substantially tube-shaped and composed of braided or interwoven wire elements. Braided or interwoven wire elements allow easy expansion and collapse of the VCD 582 within a vessel 10 in the same or similar manner as can be provided by various known stent devices, such as self-expanding metallic stents or other expandable or woven stents. The support frame 585 thus expands from a first circumference when in a collapsed configuration to a second circumference larger than the first circumference when in an expanded configuration; the second circumference being similar to or greater than the inner circumference of the vessel 10 within which the VCD 582 is intended to be implanted. The individual wire elements of the support frame 585 may be fabricated from any biodegradable or non-absorbable material, or any combinations thereof, such as those described with reference to FIG. 2. In addition, some or all of the support frame 585 may be pre-shaped to a desired shape and curvature utilizing a shape memory metal or metal alloy, such as nickel-titanium alloy (e.g., Nitinol), a shape memory polymer, or any combination thereof.

In one embodiment of the VCD 582, the spacing between the braided or interwoven wire elements of the support frame 585 is sufficiently small enough that hemostasis can be achieved without a sealing membrane. In other words, the wire elements perform the sealing function. According to some embodiments, the spacing between the braided or interwoven wire elements of the support frame 585 may differ and/or the wire elements may have different density or shape in different areas of the frame. For example, in one embodiment, the support frame 585 elements are denser at or near the area of the VCD 582 which is intended to be positioned proximate to the vessel's 10 puncture site 15, so as to achieve homeostasis without a sealing membrane.

According to various embodiments, the braided or interwoven wire elements described with reference to FIG. 5F may be included with other VCD embodiments to provide an easily expandable and collapsible support frame. In addition, other features described with reference to other embodiments, such as a sealing membrane, may be incorporated with the VCD 582 of FIG. 5F.

Figure 5G:
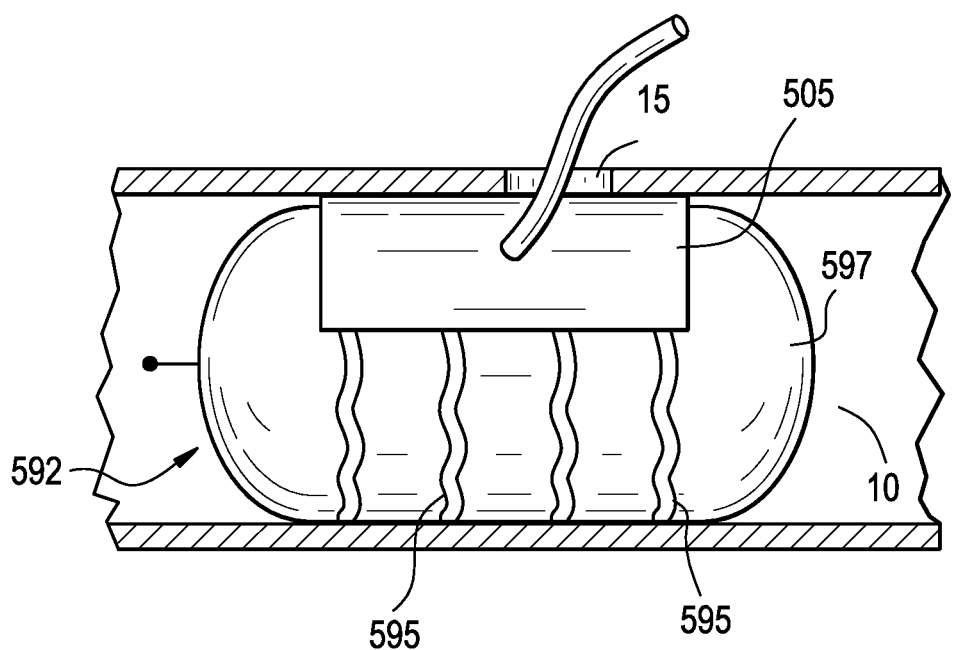

FIG. 5G illustrates another embodiment of a VCD. Here, the VCD 592 includes a sealing membrane 505 and expandable support frame 595 that are positioned over an expandable balloon 597, which is utilized to expand the support frame 595 and secure the VCD 592 within the vessel 10. In one embodiment, the support frame 595 includes straps or other members securing the sealing membrane 505 to the balloon. Similar to other embodiments, the sealing membrane 505 of this embodiment may cover all or a portion of the support frame 595 and the balloon 597. During delivery, the balloon 597 is maintained in a deflated state. Upon inserting the VCD 592 into the vessel 10 and upon positioning the sealing membrane 505 at or near the puncture site 15, the balloon 597 is inflated. Inflating the balloon 597 expands the support frame 595 and the sealing membrane 505 within the vessel 10 and at least partially covers the puncture site 15, thereby assisting hemostasis. The balloon 597 can be subsequently deflated for extraction through a small hole (e.g., less than approximately 2 mm, and even less than approximately 1 mm) in the sealing membrane 505 and then through the puncture site 15. The balloon may be expanded by any conventional means for intravascularly expanding compliant bodies, such as by delivering a liquid into the balloon.

A VCD 592 embodiment that includes an expandable balloon 597 to expand the support frame 595 permits the use of a non self-expanding material for forming the support frame 595. For example, the support frame 595 of this embodiment may be formed from, but is not limited to, bioabsorbable polymers or copolymers, including, but not limited to, polylactide (e.g., PLLA, PDLA), PGA, PLGA, PDS, PCL, PGA-TMC, polygluconate, PLA, polylactic acid-polyethylene oxide copolymers, poly(hydroxybutyrate), polyanhydride, polyphosphoester, poly(amino acids), poly(alpha-hydroxy acid), or any other similar copolymers; magnesium or magnesium alloys; or aluminum or aluminum alloys; as well as any composites and combinations thereof. Other combinations that may include biodegradable materials may also be utilized to form part or all of the support frame 595.

The foregoing VCD embodiments described with reference to FIGS. 1-5G are illustrative and are not intended to be limiting. Moreover, any of the materials, manufacturing techniques, and characteristics of the various VCD embodiments and individual components described herein may likewise apply to any other VCD embodiment described, unless explicitly stated to the contrary.

Methods of Delivery and Corresponding Delivery System

In various embodiments, the VCD and delivery systems are used by a physician, surgeon, interventional cardiologist, emergency medical technician, other medical specialist, or the like. In describing the methods of use of the VCD and deployment systems, such persons may be referred to herein as an "operator".

FIG. 6 is a process flow diagram of illustrating one embodiment of a method 600 for performing an endovascular procedure and delivering and implanting a VCD to close a vessel puncture. The method is described with additional reference to FIGS. 7A-7D illustrating stages of the method 600. The method 600 begins at block 605 by inserting a sheath 700 through a puncture site 15 formed in a vessel wall 12 into the lumen of the vessel 10. In one embodiment, the sheath 700 is optionally inserted with the assistance of a micropuncture needle, Seldinger needle, dilator, introducer, and/or another similar device. In one embodiment, the sheath 700 utilized to perform the endovascular procedure is the same as the sheath utilized to deliver and position a VCD. In another embodiment, a different sheath is used to deliver the VCD. Certain embodiments of delivery systems are described with reference to FIGS. 9A-10P.

Following block 605 is block 610, in which an endovascular procedure is performed via the access to the vessel 10 provided by the sheath 700. In one embodiment, the procedure is performed prior to delivery of the VCD 100. Representative examples of suitable endovascular procedures in this step include percutaneous valve replacement or repair, cardiac ablation, endovascular graft implantation, coronary or peripheral stent implantation, diagnostic catheterization, or carotid stent implantation. Essentially any procedure requiring access to a body lumen through a puncture site may be performed.

After the endovascular procedure is performed, the same sheath may be utilized to deliver the VCD or a different sheath may be utilized.

Figure 7C:
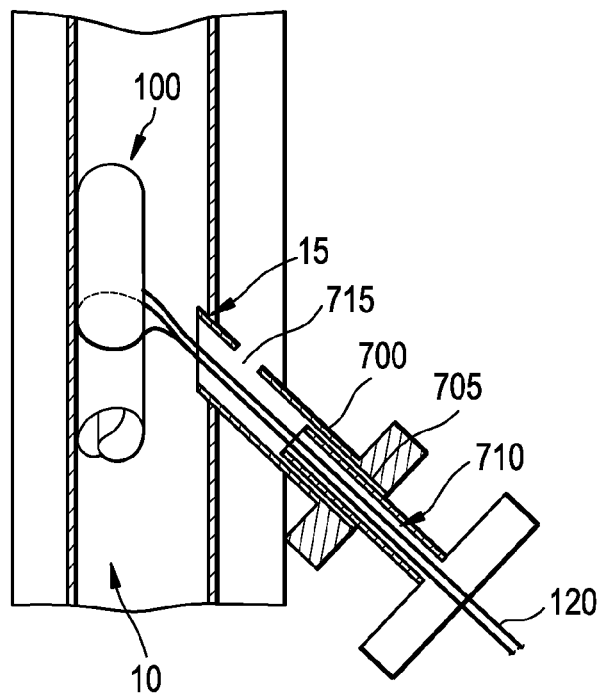

If a different sheath is utilized, blocks 615 and 620 are performed. At block 615, the first sheath is removed, leaving a guidewire within the puncture. At block 620, the VCD delivery sheath is inserted into the puncture site in the same or similar manner as described with reference to block 605 or otherwise according to suitable techniques. To position the sheath 700 (e.g., a different sheath than that positioned at block 605) within the vessel at block 620, the sheath 700 is retrieved in the proximal direction until its distal end is proximate the puncture site 15. In one embodiment, the sheath 700 is pulled proximally into the desired position with the visual aid of marks or gradations on the sheath 700 and/or by utilizing one or more sides hole 715 formed through the wall of the sheath 700. If included, blood will stop flowing through the side hole 715 when the side hole 715 is removed from the blood stream of the vessel 10, which indicates that the sheath 700 is in the desired position relative to the vessel 10, as shown by FIG. 7C. Accordingly, the side hole 715 is formed at a predetermined distance from the distal end of the sheath 700 to allow proper positioning of the sheath 700 and the VCD 100 within the vessel 10. In various embodiments, the position of the side hole 715 relative to the distal end of the sheath will vary according to the intended use and implant location for the VCD 100.

According to some embodiments, a guidewire may optionally be utilized to facilitate delivering and positioning the VCD 100 within the vessel 10. A guidewire may be delivered through the sheath 700 after the sheath is properly positioned, as described with reference to block 620. A guidewire can further be utilized to ease subsequent access within the vessel 10, such as may be performed in the case of a VCD 100 malfunction, failure, or other reason calling for the removal of a delivered VCD 100. Upon removal of the initial VCD, a replacement VCD 100 may be delivered over the guidewire. Moreover, a guidewire further facilitates introducing additional means to prevent and/or reduce bleeding from an unsealed puncture 15, such as may be useful during replacement or repositioning of a VCD 100 prior to sealing the puncture 15. If used, a guidewire may be removed after the VCD 100 is positioned (e.g., after block 640 below).

In yet other embodiments, a guidewire may be inserted after a collapsed VCD 100 is advanced into the vessel (e.g., after block 635 below). The guidewire may be delivered through the same delivery sheath 700 (e.g., parallel to the VCD 100), or, in some embodiments, the delivery system may include an additional passage or lumen through which the guidewire may be passed, positioning the guidewire parallel to the collapsed VCD 100.

Operations continue to block 625, in which a loading tube 705 housing a compressed VCD 100 is inserted into the sheath 700, as illustrated in FIG. 7A, according to one embodiment. Although the VCD is referenced as the VCD 100, it is understood that any of the VCD embodiments described herein may be delivered by similar techniques. The loading tube 705 provides easier insertion of the VCD 100 into the sheath 700 by already containing the VCD 100 in a collapsed configuration and having a diameter sized to fit within the sheath 700. In embodiments in which the sheath 700 includes a hemostasis valve to control bleeding and prevent air embolisms, the loading tube 705 is inserted past the hemostasis valve. The loading tube 705 may be pre-loaded prior to the procedure, or it may be loaded by the operator during the procedure. In another embodiment, a loading tube 705 is not used, and the VCD is loaded directly into the sheath 700.

Following block 625 is block 630, in which the VCD 100 is pushed through the loading tube 705 and the sheath 700 until it exits into the lumen of the vessel 10. In one embodiment, a push rod 710 (also interchangeably referred to herein as a "pusher" or "pusher device") is utilized to push the VCD 100 into the sheath 700 until it exits the sheath 700 into the vessel 10, such as is shown by FIG. 7B. In one embodiment, a push rod 710 includes marks, gradations, or other means for indicating the depth of the push rod 710 penetration within and relative to the sheath 700. In one embodiment, a push rod 710 includes a stopping mechanism to prevent further insertion of the push rod 710 and thus the VCD 100 through the sheath 700. Upon exiting the sheath 700, an anchoring tab 120 and/or a pull string attached to the VCD 100, such as is described with reference to FIGS. 1-2, extends from the VCD 100 and exits proximally from the sheath 700 to facilitate positioning and release of the VCD 100. In another embodiment, instead of a push rod, an actuator handle in operation with a loading tube 705 is utilized to advance the VCD 100 through the sheath 700, such as is described with reference to FIGS. 9C-9F.

Block 635 follows block 630, in which the sheath 700, the push rod 710, and the VCD 100 are retrieved in the proximal direction until its distal end is proximate the puncture site 15, such as is shown by FIG. 4C. In addition, the anchoring tab 120 and/or pull string is used to pull the VCD 100 into position proximate the puncture site 15. In another embodiment, the push rod 710 is used to facilitate positioning the VCD 100. In yet other embodiments, additional features may facilitate positioning of the VCD 100 in a desired intraluminal location. Examples of these features, some of which are further described herein, include curved tips, springs or biasing members, and the like. In addition, the sheath 700 may be further positioned according to the techniques described with reference to blocks 615 and 620. In other embodiments, however, the sheath 700 is fully removed from the vessel 10, and, optionally, from the patient's body, at block 635.

Figure 7D:
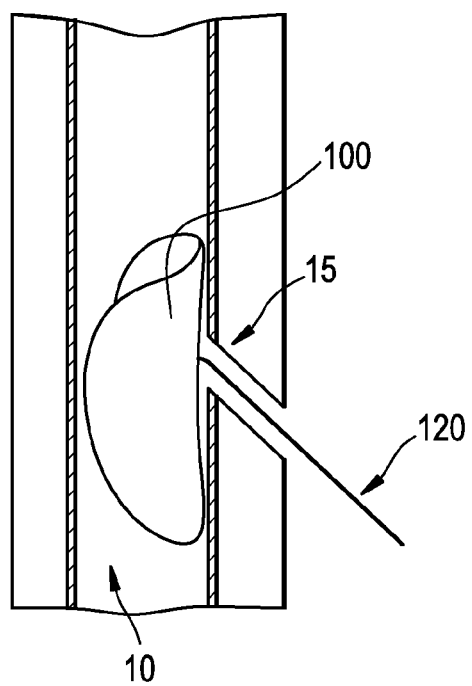

Following block 635 is block 640, in which, according to one embodiment, a containment mechanism releasably retaining the VCD 100 in a collapsed configuration is released to permit the support frame to fully expand and position the sealing membrane against the vessel puncture site 15, such as is shown by FIG. 7D. Example containment mechanisms and their operation are described in more detail with reference to FIGS. 3A-3C and 10A-10P. As part of releasing a containment mechanism, the anchoring tab 120 and/or pull string can be further manipulated to facilitate positioning the VCD 100 at or near the puncture site 15. For example, depending upon the attachment point location of the anchoring tab 120 and/or pull string to the VCD 100, pulling the anchoring tab 120 and/or pull string proximally will approximately center or otherwise align the VCD 100 at or near the puncture site 15 as desired. In some embodiments, a safety tab (not shown), as further described with reference to FIG. 9F, for example, is optionally included with the containment mechanism to prevent unintentional release of the VCD 100.

Block 645 follows block 640, in which the anchoring tab 120 is secured to the patient's tissue to further secure the VCD 100 within the vessel and to prevent intraluminal migration of the VCD. In certain embodiments, the anchoring tab 120 is secured to the patient's tissue at or near the vessel access site using suture, biocompatible adhesive, bandage, tape, or an integral hook. In another embodiment, the anchoring tab 120 is secured by suturing or taping closed the vessel access site, trapping the anchoring tab 120 therein.

Figure 11A:
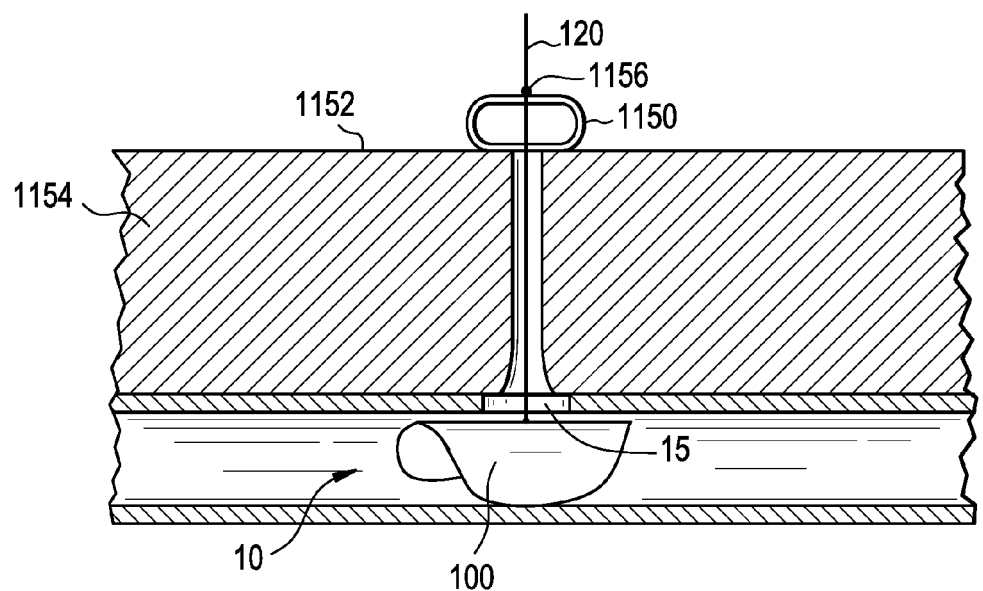
FIGS. 11A-11C are cross-sectional views illustrating securing a VCD within a vessel, according to one embodiment.
Figure 11B:
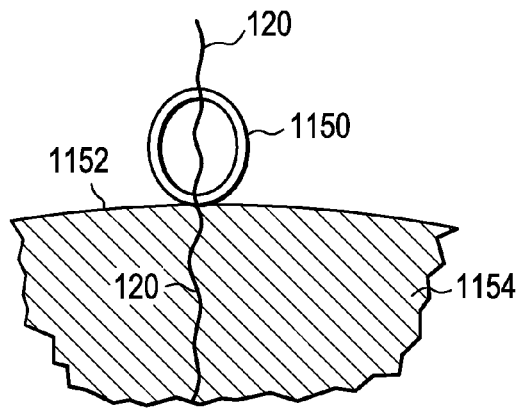
Figure 11C:
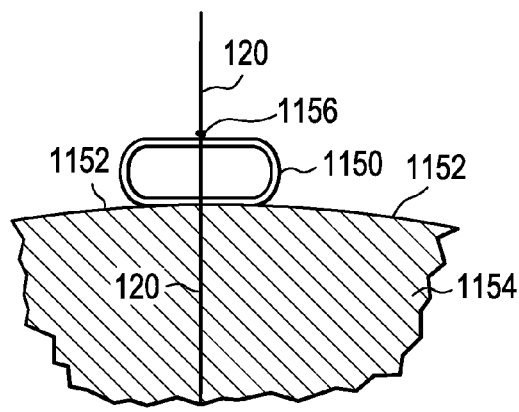

In another embodiment, as illustrated in FIGS. 11A-11C, instead of, or in addition to, securing the anchoring tab 120 to the patient's tissue, a rebounding member 1150 that applies a tensile force on the anchoring tab 120 is included to bias or otherwise secure the VCD 100 within the vessel against the puncture site 15. The rebounding member 1150 can be configured in any number of ways to provide an elastic member that rebounds from a compressed to an expanded configuration, including, but not limited to, a spring, an elastic tube, an elastic ring, an arm, a foam or other elastic member, and the like. For example, the rebounding member 1150 can be formed from an elastic polymer, such as, but not limited to silicone or latex, or from an elastic metal, or any combination thereof.

The anchoring tab 120 is threaded through or otherwise adjustably coupled to the rebounding member 1150. When positioning the VCD 100 within the vessel 10, the rebounding member 1150 is positioned against the patient's skin surface 1152. The anchoring tab 120, which extends through from the VCD 100 through the patient's skin tissue 1154, is then secured in a relatively taut position against the rebounding member 1150. In one embodiment, the anchoring tab 120 is secured in tension by a locking means 1156, which selectively locks the rebounding member 1150 against the anchoring tab 120 (or pull string extending therefrom). The locking means 1156 may be configured as, but is not limited to, a slip-knot, a clamp, a tab and teeth assembly, and or any other means operable to selectively secure the rebounding member 1150 at one or more positions along the anchoring tab 120.

FIG. 11B illustrates a partial view of the anchoring tab 120 and the rebounding member 1150 against the patient's skin 1152, but in a loose state. FIG. 11C illustrates a partial view of the anchoring tab 120 pulling the rebounding member 1150 against the patient's skin, compressing the rebounding member 1150 at least partially. Compression of the rebounding member 1150 maintains the anchoring tab 120 in tension and pulls the VCD 100 proximally against the inner vessel wall, as shown in FIG. 11A. The rebounding member 1150 described with reference to FIGS. 11A-11C may be utilized with any of the various embodiments described herein. Other means to secure the VCD 100 in place, such as securing the anchoring tab 120 to the patient's skin, are envisioned.

The method 600 may end after block 645, having delivered and secured a VCD 100 within a vessel 10 at or near a puncture site 15 to facilitate hemostasis at the puncture site. As discussed, after implantation of the VCD 100, some or all of the VCD 100 may degrade and/or absorb over time, reducing the contents remaining within the vessel. This characteristic of the VCD may be beneficial, for example, to simplify subsequent access at or near the same vessel site, for example if the patient needs another endovascular procedure.

In some instances, it may be desirable to remove a VCD from a vessel during or after implantation, such as in the case of device failure, surgical complications, or for any other reason. In one embodiment, a VCD having a peripheral support frame, such as those described with reference to FIGS. 2-4J, can be retrieved, even after expansion, by pulling an anchoring tab and/or pull string proximally while holding a delivery sheath in place. This proximal force will pull the VCD back against the distal end of the sheath. An expanded support frame, because it may optionally be formed from an at least slightly flexible material, will bend along any direction, allowing the VCD to collapse and be retrieved through the sheath or other delivery system. A VCD that is still in a collapsed configuration will be even easier to retrieve, by simply pulling proximally through the distal end of the sheath or the puncture directly. It is appreciated that additional guide wires or other guiding instruments may be passed through the delivery system to facilitate retrieval of a VCD.

The VCD may be retrieved using other methods and devices. For example, a snaring loop may be used to capture and grasp the VCD, and optionally collapse the VCD prior to retrieval. In another example, an elongated member, such as a wire or rod, having a hook at its distal end may be inserted into to the vessel, for example, through a sheath via the same puncture site through which the VCD was delivered. The elongated member and its hook enable capturing at least a portion of the VCD (e.g., a portion of the support frame, a cross-member support, the anchoring tab, etc.) to pull the VCD proximally, causing it to bend and allowing retrieval through a sheath.

After retrieving a VCD, the same sheath may be utilized for the re-delivery of the same or different VCD, or a new sheath may be inserted. The new sheath may be inserted over a guide wire inserted prior to removal of the prior sheath, or may be inserted over the anchoring tab and/or pull string extending through the puncture from a VCD prior to its removal. In one embodiment in which an anchoring tab and/or pull string is utilized to deliver a subsequent sheath, additional support is provided by passing a needle or other low profile sleeve over the anchoring tab and/or pull string, over which the new sheath is delivered. Other means for removing an expanded or collapsed VCD may be utilized. The aforementioned procedures are illustrative and are not intended to be limiting.

Figure 8:
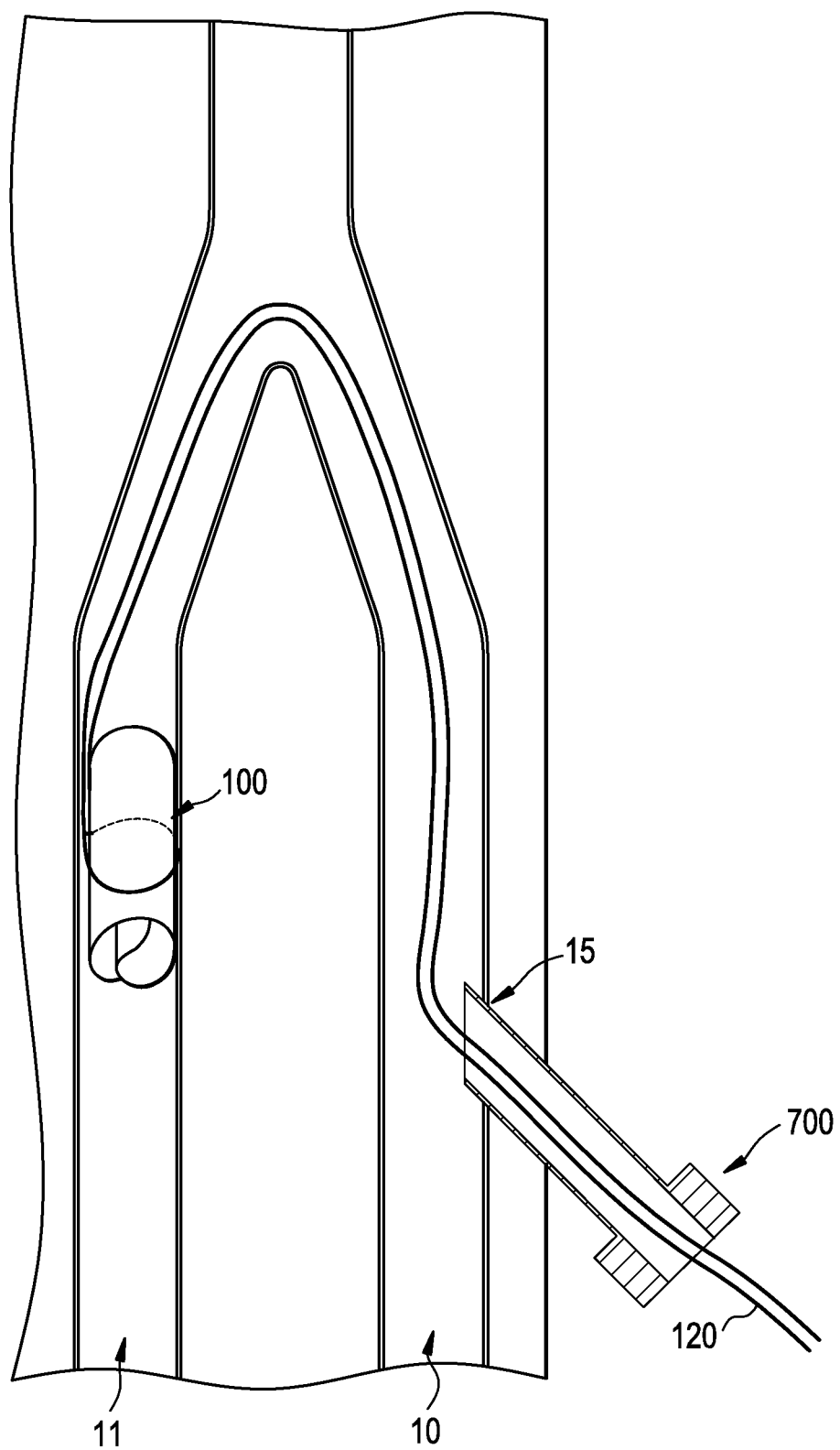
FIG. 8. is a cross-section view illustrating temporary positioning of a VCD within a vessel during delivery according to one embodiment.

FIG. 8 illustrates an embodiment in which a different technique is performed during the placement of a VCD 100. After inserting the sheath 700, and prior to performing the intended endovascular procedure, or during a preliminary stage of an endovascular procedure, a compressed VCD 100 is deployed into the vessel 10 and preliminarily positioned in an alternate vessel 11 located proximal or distal to the puncture site 15, such as in a vessel passing a segment exposed to injury during a procedure. For example, the compressed VCD 100 can be positioned in the contra-lateral iliac artery, because the vessel most susceptible to damage is the segment between the access point in the femoral or iliac artery and the aorta. However, in other embodiments, the VCD 100 may be preliminarily positioned in any other vessel location. In another example, the VCD 100 can be positioned directly in the contra-lateral iliac artery (or other vessel) through a separate, smaller-bore sheath inserted in the contra-lateral iliac artery (or other vessel), with an anchoring tab 120 and/or pull string extending proximally from the VCD 100 through the sheath 700, using known capturing methods. The preliminary position of the compressed VCD 100 can be selected to avoid interference with the endovascular procedure being performed.

After preliminarily positioning in a proximal or distal vessel, the VCD 100 is ready for rapid deployment, such as by methods similar to those described with reference to FIG. 6. Rapid deployment may be desirable in case a complication during the endovascular procedure arises, such as a dissection or perforation of the vessel, which may become fatal if not sealed. The VCD 100 can be moved from its preliminary position in the vasculature tree and positioned at or near the puncture site 15 for immediate sealing.

According to another similar embodiment, the VCD 100 may preliminarily be delivered within the same vessel (e.g., the vessel 10, as shown in FIG. 8) and distanced either in the distal or proximal direction from the puncture site 15. When delivered to a preliminary location, the VCD 100 may expand to its expanded configuration, such as is described herein. When needed to seal the puncture site 15, an anchoring tab 120 and/or pull string may be pulled proximally (e.g., through a delivery sheath 700) to cause the VCD to pass partially across the puncture site 15 and position thereover to seal the site 15. Preliminary placement of the VCD 100 may be achieved with or without the use of a containment mechanism.

FIGS. 9A-9I illustrate one embodiment of an example delivery system for delivering and positioning a VCD within a patient's vessel or other body lumen. For example, the delivery system may be used to perform some or all of the operations of the method 600 described with reference to FIG. 6. In addition, the delivery system may be used to deliver any of the example VCD embodiments described herein, and is not intended to be limited to the specific VCD embodiment described by example. Moreover, the relative dimensions and shape of the components illustrated in FIGS. 9A-9I (as well as any other figure herein) are provided to most completely illustrate the individual features and their spatial relationship and orientation with respect to other features. The relative dimensions and shapes are not limiting and other dimensions and shapes may be provided. As an example, the sheath 905 illustrated in FIG. 9A may, in some embodiments, be longer and/or more narrow relative to the overall size of the sheath than what is illustrated.

Figures 1, 9A:
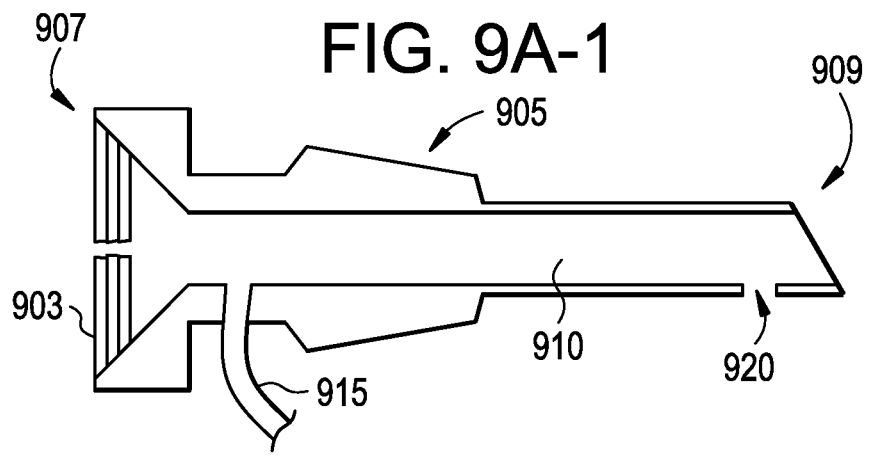
Figures 2, 9A:
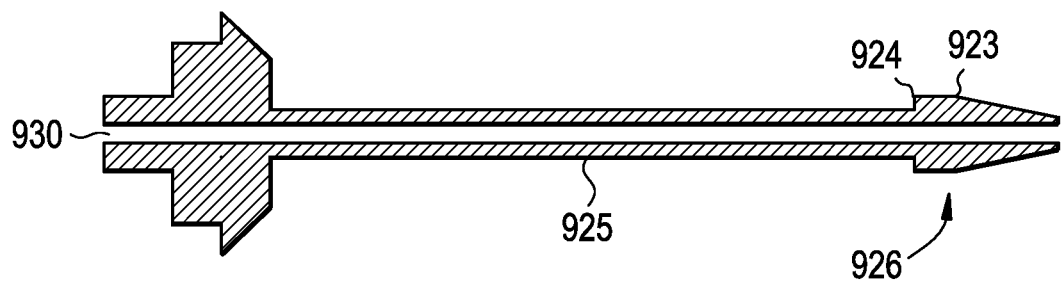

In the embodiment illustrated in FIG. 9A, a delivery system includes an introducer sheath 905 for providing access to a vessel interior. The sheath 905 forms an internal channel 910 between the proximal end 907 and the distal end 909 of the sheath 905. At or near the proximal end 907 is a port 915 in fluid or gaseous communication with internal channel 910. A side hole 920 is formed at or near the distal end 909 of the sheath 905 and in fluid (gas or liquid) communication with the internal channel 910, and thus with the port 915. In one embodiment, one or more hemostasis valves 903 are provided at or near the proximal end 907 of the sheath 905, which may be utilized to selectively access to the internal channel 910 of the sheath 905. In one embodiment, the distal end 909 of the sheath 905 is formed at an angle relative to the length of the sheath 905. This may facilitates achieving the desired position of the VCD within a vessel. It also may help prevent the VCD from backing out by maintaining it at an angle during its delivery. In various embodiments, the angle may range between approximately 30° and approximately 90° relative to the length of the sheath 905. In other embodiments, however, the distal end 909 is not angled as previously described, but formed in another suitable geometry. For example, it may be conical, curved, an opposite angle, or straight.

Figure 9B:
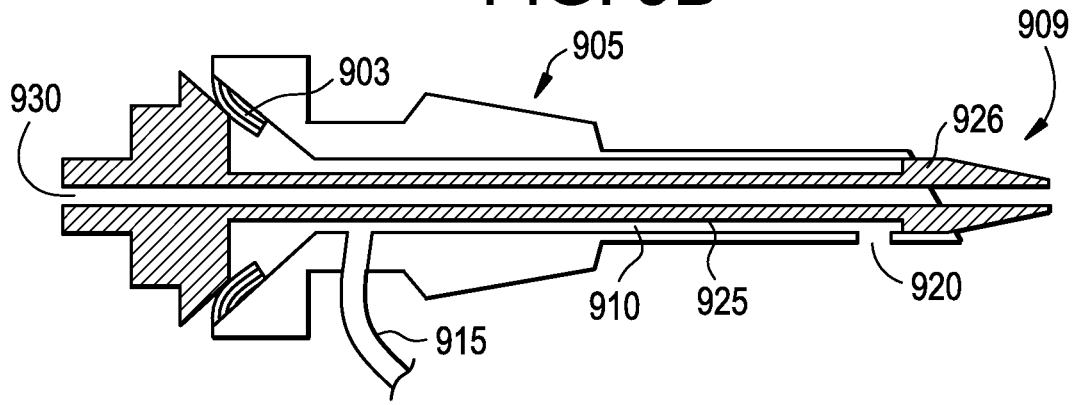

In one embodiment, a dilator 925 is also included with the delivery system to facilitate insertion of the sheath 905 into the vessel. FIGS. 9A-1 and 9A-2 illustrate the dilator 925 separate from the sheath 905, while FIG. 9B illustrates the dilator 925 inserted through the channel 910 of the sheath 905 and exiting its distal end 909. When inserted into the sheath 905, the dilator 925 substantially seals against the proximal end 907 of the sheath 905, which may optionally be facilitated by a hemostasis valve 903 integrated therewith.

In one embodiment, the distal end 926 of the dilator 925 is formed in a substantially conical shape, which reaches its maximum outer diameter at or near location 923 along the dilator 925. The dilator diameter at this location 923 is close to the same, slightly smaller than, or slightly larger than, the internal diameter of the introducer sheath channel 910, providing tight fitment of the dilator 925 within the channel 910 of the sheath 905. A tight fit accomplishes sealing the distal end 909 of the sheath 905 when the dilator 925 is extended therethrough, such as is illustrated in and described with reference to FIG. 9B.

In one embodiment, the dilator 925 has a stepped-down, reduced outer diameter proximally and beginning at location 924, which is proximal to the location 923 along the dilator 925. For example, in one embodiment, the reduced diameter of the dilator decreases by at least approximately 0.05 mm from the maximum outer diameter at area 923, such as decreasing between approximately 0.05 mm and approximately 2.5 mm, or between approximately 0.1 mm and approximately 1 mm. The position of location 924, where the stepped-down outer diameter of the dilator 925 occurs, is determined such that upon inserting the dilator 925 into the sheath 905 a predetermined amount, the area 924 is oriented between the side hole 920 and the distal end of the sheath 905. Therefore, as described below, blood may flow through the side hole 920 and into the channel 910 proximally toward the outlet port 915, while still achieving a seal at the distal end 909 of the sheath 905. In some embodiments, the distance between the areas 923 and 924 may need to accommodate greater areas on one side of the sheath 905 than another, such as when the sheath's 905 distal end 909 is angled. The distal end 926 of the dilator 925 may be formed in any other suitable shape as desired.

In one embodiment, after insertion of the dilator 925 through the sheath 905, there still exists fluid communication between the side hole 920 and the port 915. Such fluid communication permits detecting when the side hole 920 is inserted into or removed from a vessel, because blood (or other fluid) will flow into the side hole 920, through the channel 910, and exit the port 915 when exposed to blood flow, as described with reference to FIG. 6. Thus, the side hole 920 and port 915 facilitate detection of the depth in which the delivery system is inserted. In one embodiment, the fluid communication between the side hole 920 and the port 915 is provided by the difference in outer diameters of the dilator 925 and the inner diameter of the sheath channel 910. In other embodiments, however, a groove or channel formed along a dilator 925 is provided with an outer diameter that does not significantly differ from the inner diameter of the sheath channel 910, such that when positioned properly, the groove or channel aligns with both the side hole 920 and the port 915. In another embodiment, a groove or other channel is formed in the interior surface of the inner channel 910 of the sheath 905 instead of in the dilator 925. In yet another embodiment, the sheath 905 and/or the dilator 925 includes an integrated passageway formed and providing fluid communication between the side hole 920 and the port 915.

In one embodiment, the dilator 925 further includes at least one lumen 930 extending along its length through which a guide wire or other instrument can be passed. For example, the lumen 930 may have an inner diameter that accommodates guide wires or other instruments with an outer diameter or profile ranging between approximately 0.1 mm and approximately 1 mm, such as 0.9 mm in one embodiment. One or more lumens 930 formed through the dilator may be sized to accommodate larger or smaller instruments than provided by example, which may depend upon the procedure being performed and/or the patient's anatomy. The aforementioned dimensions are illustrative and are not intended to be limiting.

Accordingly, FIG. 9B illustrates the dilator 925 inserted within the inner channel 910 of the sheath 905, representing one embodiment of an arrangement utilized to deliver the sheath 905 to a patient's vessel. In one embodiment, the sheath 905 illustrated in FIGS. 9A-9I is a different sheath than is utilized to perform an endovascular procedure, thereby allowing the sheath 905 delivering a VCD to include features specific for VCD delivery. However, in other embodiments, the sheath utilized to deliver the VCD is the same sheath as is utilized to perform the subsequent endovascular procedure.

After insertion of the sheath 905 and the dilator 925 into the vessel and achieving the desired positioning based on the blood flow through the side hole 920 and the port 915, the dilator 925 is removed. In other embodiments, one or more markers may be included on the sheath 905 instead of, or in addition to, the side hole 920 and the port 915 for determining the depth of insertion of the delivery system. Upon removal of the dilator 925, the sheath 905 is ready to be loaded with the VCD for delivery.

Figure 9E:
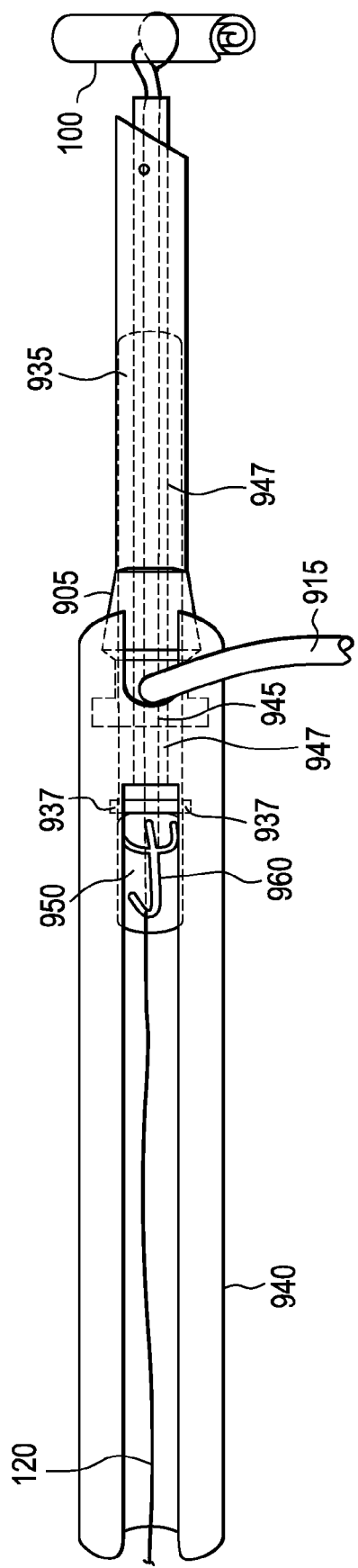
Figure 9F:
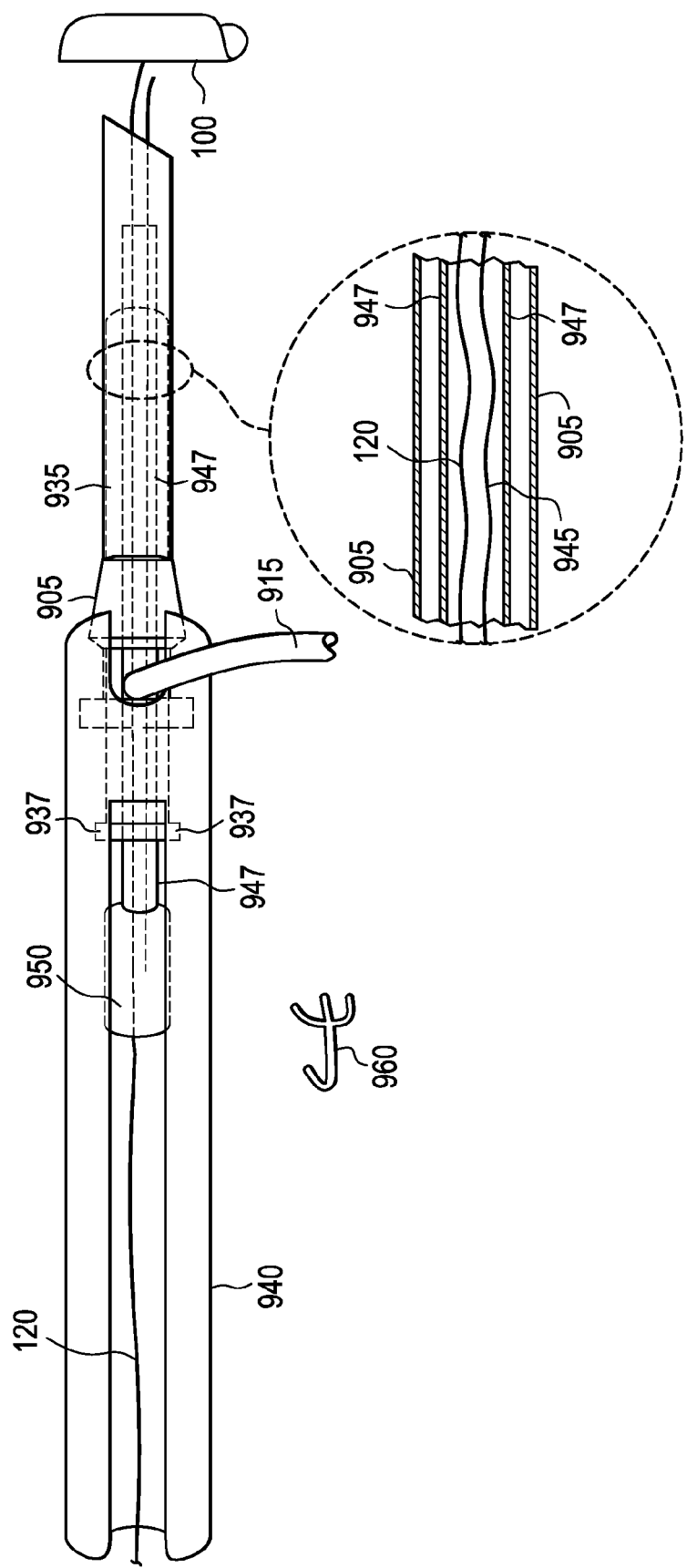
Figure 9H:
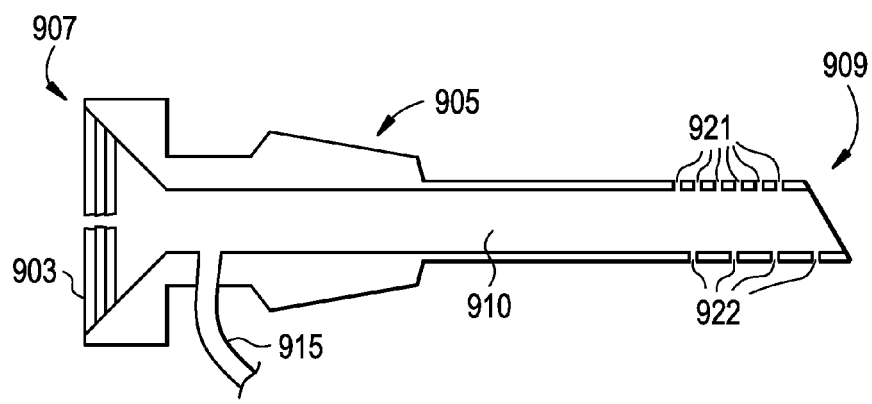
Figure 9I:
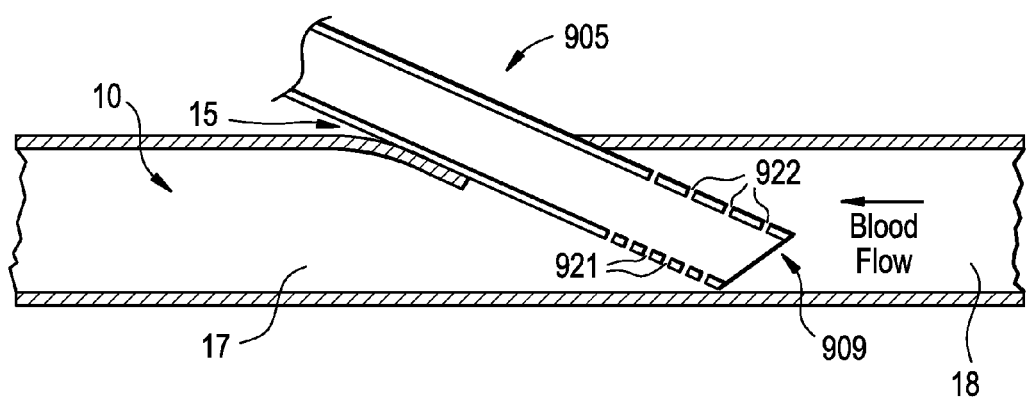

In one embodiment, one or more additional outer sleeves 927 are included with the delivery system, as illustrated in FIG. 9I. The outer sleeves 927 are sized to have an inner diameter that is the same or only slightly larger than the outer diameter of the sheath 905 to provide a tight fit of the outer sleeves 927 over the sheath 905. Each outer sleeve 927 may have a different wall thickness, resulting in a different outer diameter for each outer sleeve 927. In one embodiment, each outer sleeve 927 also includes a sleeve side hole 929 and means for achieving proper alignment of the sleeve side hole 929 with the sheath 905 side hole 920, allowing continued use of the side hole 920 and the port 915 of the sheath 905 through the sleeve side hole 929. In one embodiment, the distal edge of the each outer sleeve 927 is formed with a tapered end 928, tapering toward the distal end 909 of the sheath 905. The tapered end 928 minimizes trauma to the vessel during use.

Accordingly, the differently sized outer sleeves 927 permit one to use the same sheath 905 with different puncture sizes through a vessel. Each outer sleeve 927 is sized to a different puncture size, effectively interchangeably altering the outer diameter of the delivery system. In one embodiment, a VCD is sized to be compatible with punctures ranging from approximately 12 Fr to approximately 21 Fr. However, a sheath 905 that is 12 Fr compatible may result in undesirable blood leakage if attempted for use after a procedure utilizing a 21 Fr sheath and similarly sized puncture site. Thus, with the inclusion of additional outer sleeves 927, the VCD delivery sheath 905 can be sized to have the smallest desired outer diameter (e.g., 12 Fr, in one embodiment, though even smaller in other embodiments), while the outer sleeves 927 allow adjusting the overall outer diameter of the delivery system for use in procedures creating larger punctures. For example, with reference to the above scenario, an outer sleeve 927 can be added that will increase the overall diameter of a 12 Fr sized sheath 905 to a 21 Fr sized puncture site, preventing undesirable leakage after insertion of the delivery system including an outer sleeve 927.

In certain embodiments, an outer sleeve 927 is formed from a pliable material and/or is relatively soft in comparison to the sheath 905 material. In yet other embodiments, different outer sleeves 927 may be formed from materials that differ in stiffness, which may vary according to sleeve size. For example, in an illustrative embodiment, an adapter operably working with a 21 Fr sleeve 927 may be significantly stiffer than one working with a 14 Fr sleeve 927. Thus, an assembly that includes an outer sleeve 927 to fit the 21 Fr adapter may be stiffer, which may also be required when inserting a larger sheath into a blood vessel. In other embodiments, the stiffness or rigidity of an outer sleeve 927 varies along its length.

In various embodiments, outer sleeves 927 are supplied with a VCD, with a delivery system, with a VCD and delivery system kit, as a separate set of outer sleeves 927, or in individual sterile packages. In one embodiment, each different outer sleeve 927 and/or its packaging contains markings or other identifiers (e.g., colors, shapes, labels, etc.) to permit easy identification between the different sleeve sizes.

According to yet another embodiment, as illustrated in FIGS. 9H-9I, the sheath 905 further includes one or more holes or passages, which allow blood to flow through the distal end of the sheath 905. In some situations, the distal end 909 of the sheath 905 may be dimensioned such that it occupies a significant area within a vessel, such as if the inner diameter of the vessel is or becomes a similar or slightly smaller diameter than the sheath 905 upon insertion. These size constraints may result from the original vessel diameter being similar to the sheath outer diameter or the vessel may experience a reduced diameter due to mechanical pressure applied by the sheath on the vessel access point, vessel spasm, decreased blood flow, and/or a thrombus formed due to decreased blood flow. In these instances, insertion of the sheath 905 may result in a reduced, partially inhibited, or completely inhibited blood flow through the vessel at or near the sheath 905 and/or distal the sheath 905. For example, inhibiting blood flow from the proximal vessel side 18 of the sheath 905 (as shown in FIG. 9I) may cause a reduced vessel diameter on the distal vessel side 17 of the sheath. Decreased blood flow may cause any of several clinical side effects, including, but not limited to, ischemia of distal organs or tissue, thrombus formation, or a vessel collapse distal to the sheath 905. In addition, decreased diameters may increase the difficulty by which a VCD is positioned within the vessel.

To minimize or avoid these and other possible complications, one or more holes or other passages are formed through the sheath 905 at or near its distal 909. According to the embodiment shown in FIG. 9H, the distal end 909 of the sheath 905 includes a first series of holes 921 extending through one side of the sheath 905 wall and a second series of holes 922 extending through the approximate opposite side of the sheath 905 wall. In one embodiment, the first series of holes 921 correspond with the second series of holes 922; however, in other embodiments, the number of holes and/or the alignment of holes between the first and second series of holes 921, 922 may vary. For example, the number and orientation of holes can be selected to provide the desired blood flow rate, whereby the greater number of holes within the vessel will allow greater rates of blood flow through the sheath. However, in other embodiments, there may only be one hole selected from the either the first series of holes 921 or the second series of holes 922. For example, a single hole 921 may exist (e.g., one on the distal vessel side 17 of the sheath 905 when within the vessel), allowing blood to flow through the sheath distal end 909 and out the single hole 921 of the sheath 905. Moreover, in another embodiment, the side hole 920, illustrated in FIG. 9A-1, for example, may also serve as one or more of the holes for allowing blood flow through the sheath 905. With reference to FIG. 9I, a sheath 905 including a first series of holes 921 and a second series of holes 922 is shown inserted through an access site 15 into a vessel 10. In this example, blood flows within the vessel 10 from the proximal vessel side 18 of the sheath 905 to the distal vessel side 17 of the sheath 905. To prevent blockage or reduced blood flow, blood flows through the second series of holes 922 into the interior of the sheath 905 and exits through the first series of holes 921.

In one embodiment, an internal member, such as a tube, rod, or dilator, is used to selectively seal one or more of the first series of holes 921 and/or the second series of holes 922, allowing for selectively maintaining some holes 921, 922 in an open state, while maintaining other holes 921, 922 in a closed state. Selectively sealing the holes 921, 922 may be desirable when positioning the sheath 905 within the vessel 10 results in some of the holes 921, 922 within the vessel and some outside, allowing those outside the vessel to be sealed to prevent blood loss.

In one embodiment, the method of delivering a VCD may include a stage during which a sheath 905 is positioned within a vessel 10 to test for acceptable blood flow levels and/or whether the vessel 10 inner diameter is an acceptable size prior to delivering a VCD. For example, a test may be performed by introducing a contrast medium through the sheath 905 and visualizing (by any known means for visualizing flow and/or substance within a vessel) the contrast medium's passage to the distal vessel side 17. Moreover, to further reduce vessel restriction and/or blockage, vasodilatation drugs for treating spasm or vasodilatation of the vessel 10, such as, but not limited to, Nitroglycerin, Papaverine, etc., may be delivered at any stage of the delivery procedure.

FIG. 9C-1 illustrates an embodiment including a VCD loading tube 935 containing a VCD 100 and FIG. 9C-2 illustrates an embodiment including an actuator handle 940 containing the loading tube 935 to facilitate delivery and release of the VCD 100. The loading tube 935 forms a channel into which a VCD 100 is loaded. In one embodiment, the loading tube 935 further includes a proximal rim 937 (or other member) extending radially at or near its proximal end, which serves to restrain the loading tube 935 during insertion into a sheath 905, as described with reference to FIG. 9D. However, a rim may not be necessary, for example, where the loading tube 935 forms a tight enough fit within the sheath 905 (e.g., at the hemostasis valve 903) such that the loading tube 935 remains in place during delivery.

The VCD 100 may be any VCD described herein. In this embodiment, VCD 100 includes at least an anchoring tab 120 and/or pull string and a containment mechanism having a release wire 945, both of which pass through and are operably integrated with the actuator handle 940. As shown, the VCD 100 is loaded into the loading tube 935, such as in a rolled or otherwise collapsed configuration. The VCD 100 may be pre-loaded, such as during manufacturing and/or packaging prior to delivery, or may be loaded into the loading tube 935 by an operator as part of the delivery procedure. When loaded, the anchoring tab 120 and/or pull string extend proximally from the loading tube 935. The containment mechanism may be any suitable containment mechanism described herein. The release wire 945 may be one or more wires or other members operable for selectively releasing the containment mechanism and allowing expansion of the VCD 100, which may depend upon the design and operation of the containment mechanism.

As shown in FIG. 9C-2, the loading tube 935 is inserted into the actuator handle 940, such that the loading tube 935 extends at least partially from the distal end 955 of the actuator handle 940. The loading tube 935 may be preloaded into the actuator handle 940, (e.g., it may be inserted during manufacture, assembly, or packaging of the VCD system) prior to the operator beginning the delivery procedure. Alternatively, the loading tube may be inserted into the actuator handle by an operator as part of the delivery procedure.

FIG. 9D illustrates the actuator handle 940 and loading tube 935 being used with the sheath 905 that is described with reference to FIGS. 9A-9B, which is performed after insertion and placement of the sheath 905 into a vessel and after removal of a dilator 925 if used. The distal end 955 of the actuator handle 940 may optionally include a first elongated slot 943 defined along a portion of its length from the proximal end of the actuator handle 940 to at least some intermediate point. The first elongated slot allows the actuating mechanism 950, which is described in more detail with reference to FIGS. 9E-9F, to slide distally toward the vessel during the delivery procedure to advance the push rod 947. The elongated slot 943 serves to control the push rod 947 movement to be substantially straight, and to prevents rotation of the collapsed VCD 100 during delivery. In addition, the actuator handle 940 may optionally include a second slot 949 extending from its distal end 955. The second slot 949 is shaped to receive an outlet port 915 of the delivery sheath 905 if included. Moreover, as shown in FIG. 9D, the aligned orientation of the second slot 949 and outlet port 915 allow the operator to correctly orient the transfer of VCD 100 from the loading tube 935 into the sheath 905. In other embodiments, however, other means may be used for assuring the correct orientation between the introducer sheath 905 and the loading tube 935 including, but not limited to, orientation pins, slots, and/or marking.

If a hemostasis valve 903 is provided on the sheath 905, the insertion of the loading tube 935 in the distal direction into the sheath 905 will force open the hemostasis valve, providing selective access into the channel 910 of the sheath 905. With reference to FIG. 9D, the loading tube 935 is advanced into the proximal end 907 of the sheath 905. In one embodiment, the loading tube 935 seats within the proximal end 907 and remains in position due to its shape and/or tight fit therein.

The actuator handle 940 includes a push rod 947 slideably contained within the body of the actuator handle 940 and operably attached to the actuating mechanism 950. The push rod 947 is used to advance the VCD 100 distally out of the loading tube 935 and into the inner channel 910 of the sheath 905. An operator advances the push rod 947 by grasping and sliding the safety catch 960 distally through the first elongated slot 943.

Next, as illustrated in FIG. 9E, the push rod 947 continues to be advanced distally through the actuator handle 940 and the sheath 905, pushing the VCD 100 through the sheath 905 until it exits its distal end 909. Until the containment mechanism and the release wire 945 are released, the VCD 100 remains in a collapsed configuration. At this stage, the operator may confirm the position of the implant using any suitable imaging techniques, such as, but not limited to, fluoroscopy or ultrasound. The anchoring tab 120 and/or pull string extending proximally through the delivery mechanism and attached to the VCD 100 may also be utilized to position the VCD 100.

FIG. 9F illustrates an embodiment of the operation of the delivery mechanism during release of the VCD 100. First, the safety catch 960 of the actuating mechanism 950 is removed, which, when in place, prevents unintentional actuation of the containment release mechanism (e.g., the loop retainer pin described with reference to FIG. 3D, for example). The operator then proceeds to remove the sheath 905 and actuator handle 940 proximally away from the vessel, which in turn pulls the anchoring tab 120 and/or pull string causing the VCD 100 to be positioned proximate the puncture site. As the sheath 905 is pulled in the proximal direction and the VCD 100 is positioned against the vessel wall, resistance against a spring within the actuating mechanism is increased because the release wire 945 is attached to the actuating mechanism 950. Increased compression of the spring by pulling the sheath 905 and the actuator handle 940 proximally indicates that the VCD 100 is sufficiently positioned against the vessel wall and ready for expansion. In one embodiment, a great enough tension is caused by pulling the sheath 905 and the actuator handle 940 proximally combined with the resistance of the VCD 100 pulled against the vessel wall, which results in a change in position of the actuating mechanism and, in turn, releases the containment mechanism (e.g., a loop retaining pin, etc.). For example, with reference to the containment mechanism described with reference to FIG. 3D, increased tension will cause proximal movement of the loop retaining pin 340 until the looped end 339 is released from the retainer pin 340, releasing the loop 335 from around the VCD 100. A spring may be operably included with the actuating mechanism 950 to increase the force required for the actuating the mechanism provided, preventing pre-release of the implant. In another embodiment, the release wire 945 (or other containment mechanism release) is manually or selectively released by the operator or by any other suitable means, such as the various example containment mechanism embodiments described herein.

Accordingly, release of the containment mechanism causes the VCD 100 to expand and position against the vessel wall at or near the puncture site in part due to the pre-shaped configuration of its support frame expanding to its natural stable state. After expansion, the operator may complete the procedure by securing the anchoring tab 120 and/or pull string to the patient's tissue.

The delivery system described with reference to FIGS. 9A-9I can be suitably adapted for delivery of any VCD embodiment described herein. The combination of features are described for illustrative purposes only and are not intended to be limiting.

Figure 10A:
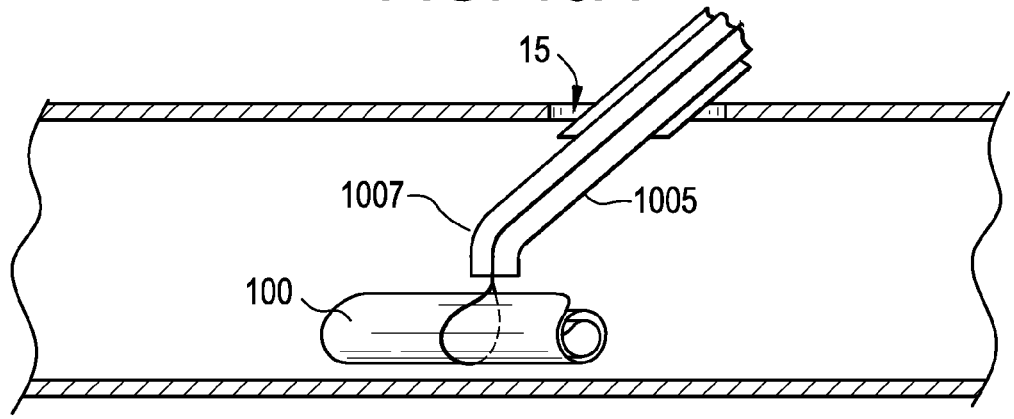
FIGS. 10A-10P are cross-sectional views illustrating additional delivery systems and corresponding containment mechanisms according to other representative embodiments.
Figure 10B:
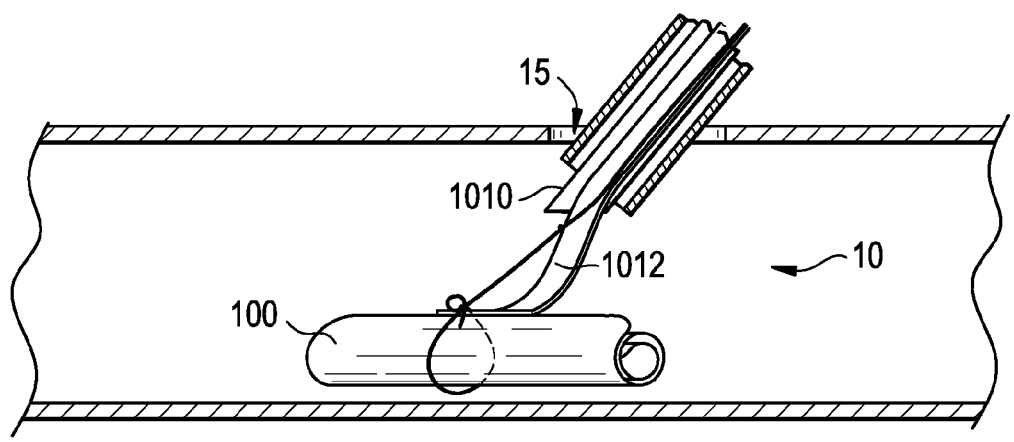
Figure 10C:
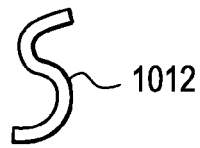
Figure 10D:
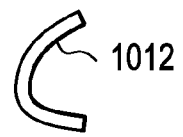
Figure 10E:
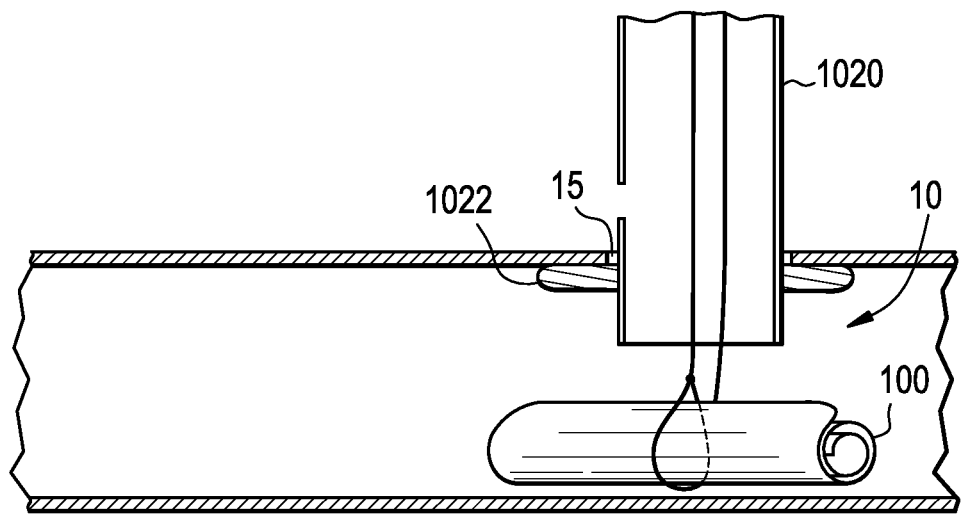
Figure 10F:
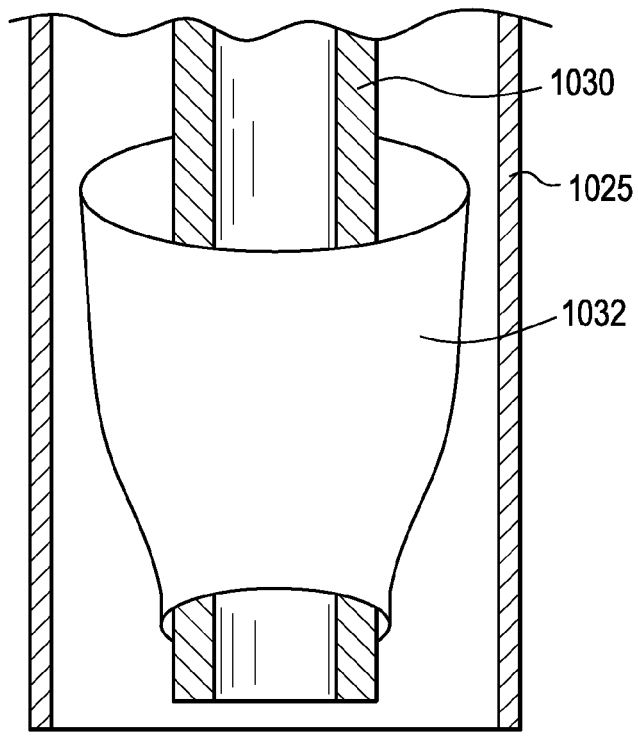
Figure 10G:
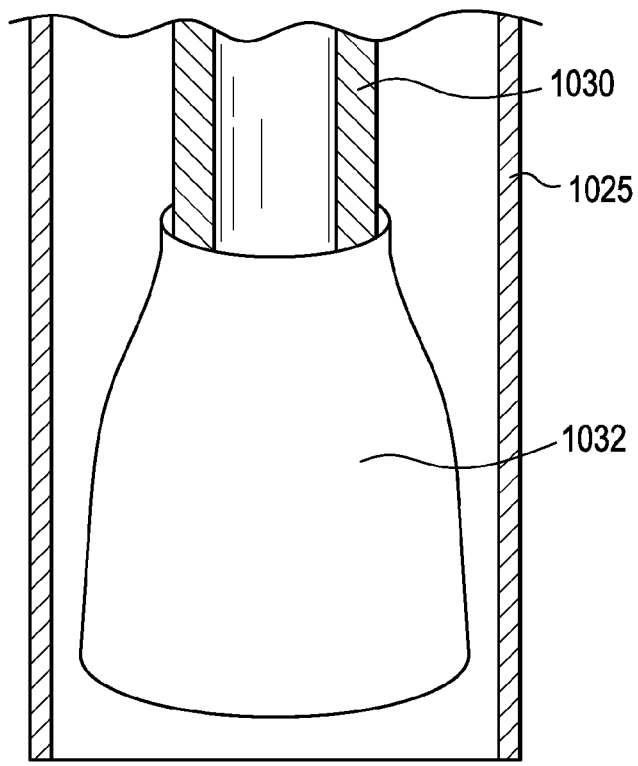
Figure 10H:
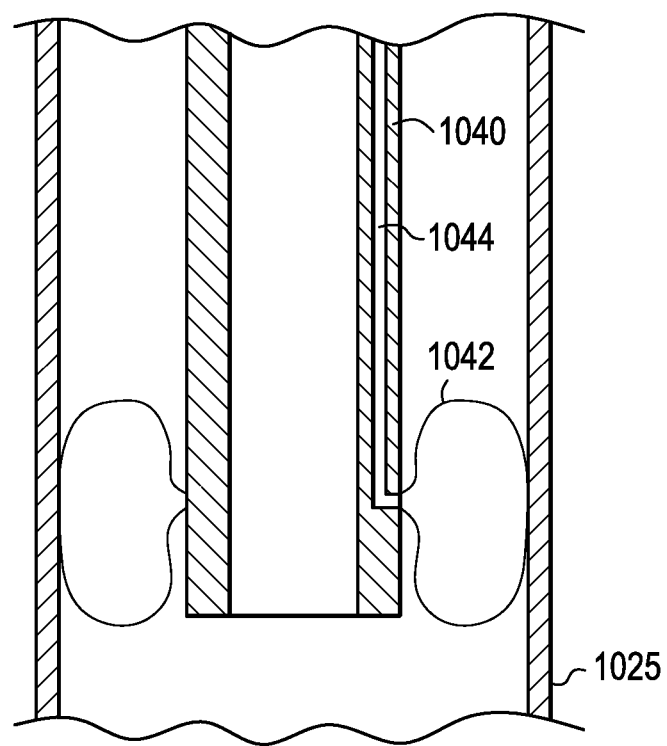
Figure 10I:
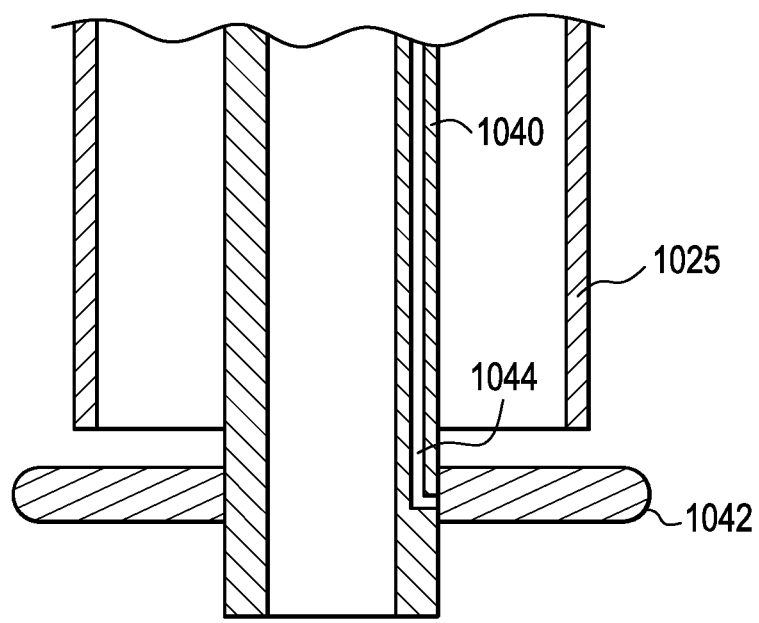
Figure 10J:
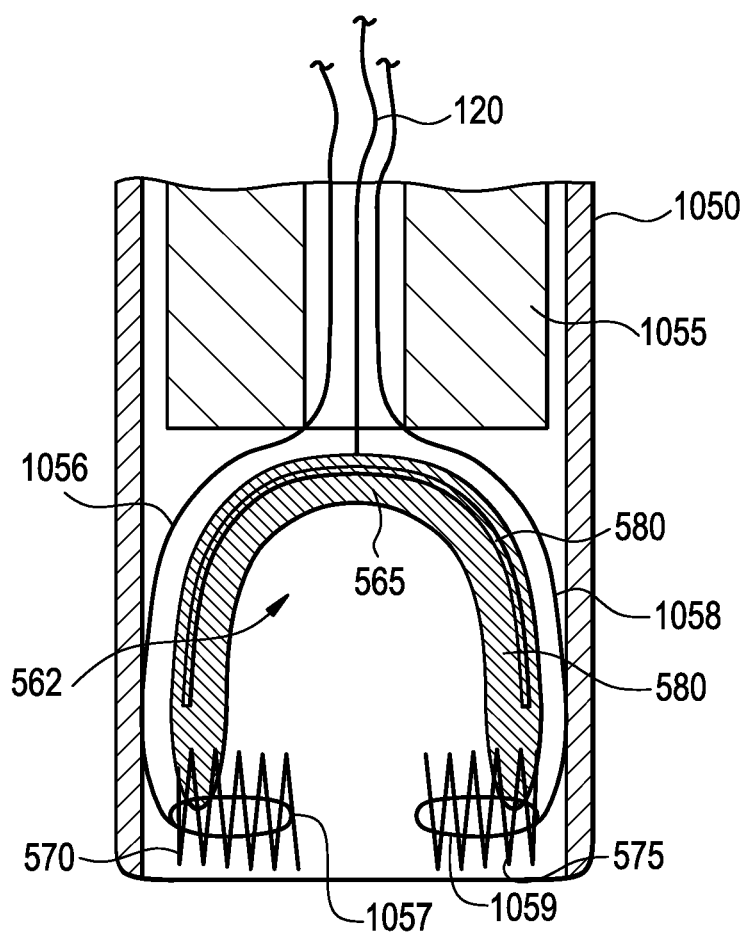
Figure 10K:
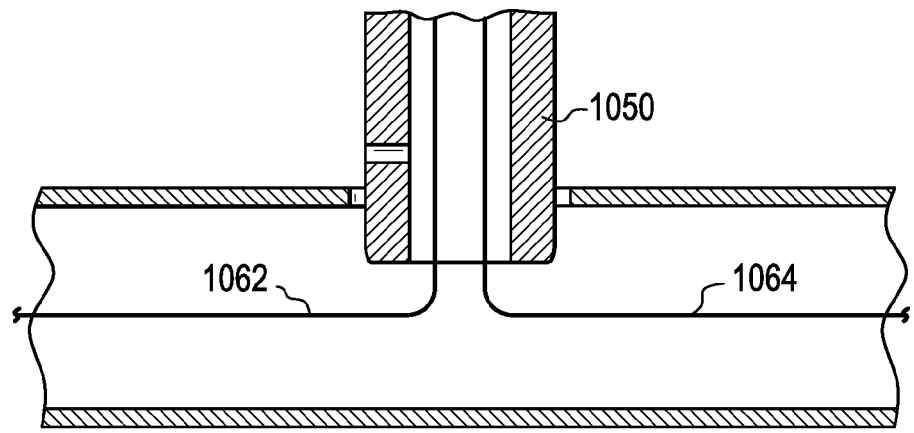
Figure 10L:
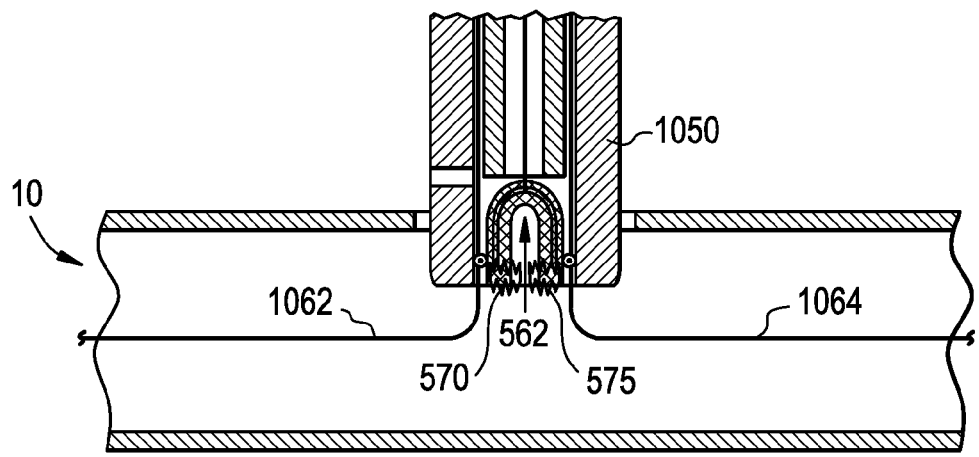
Figure 10M:
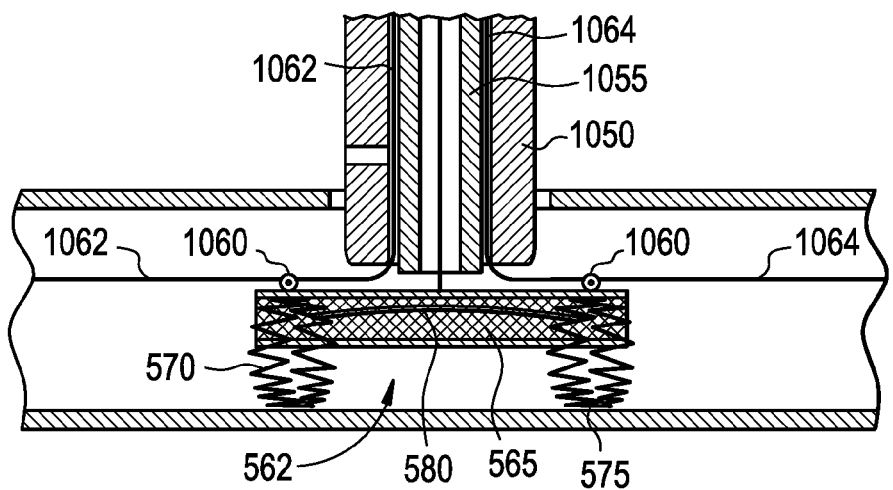
Figure 10N:
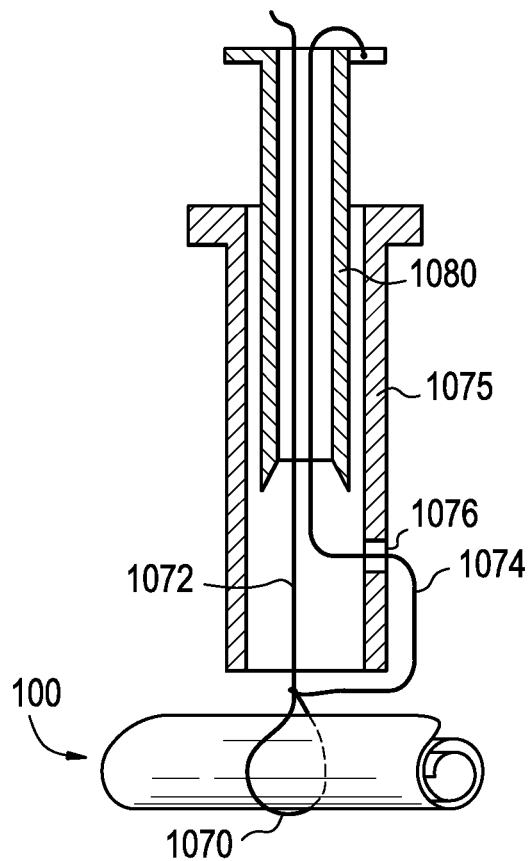
Figure 10O:
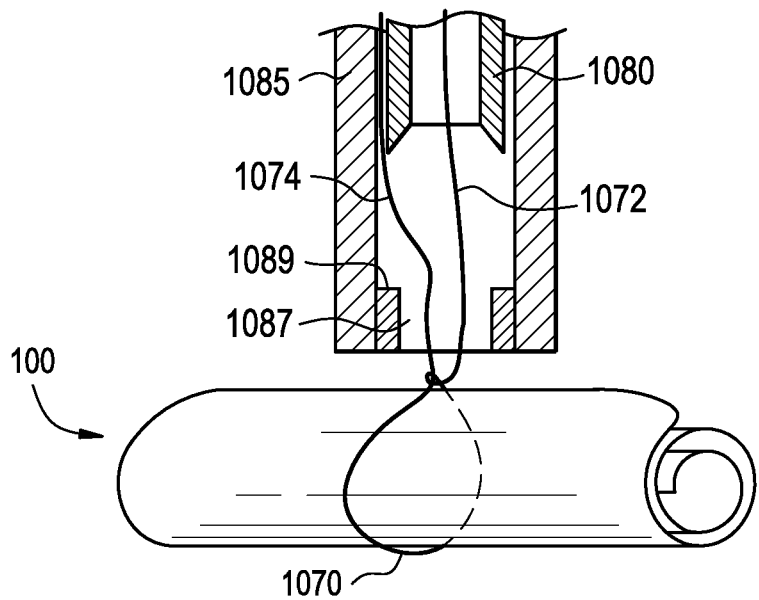
Figure 10P:
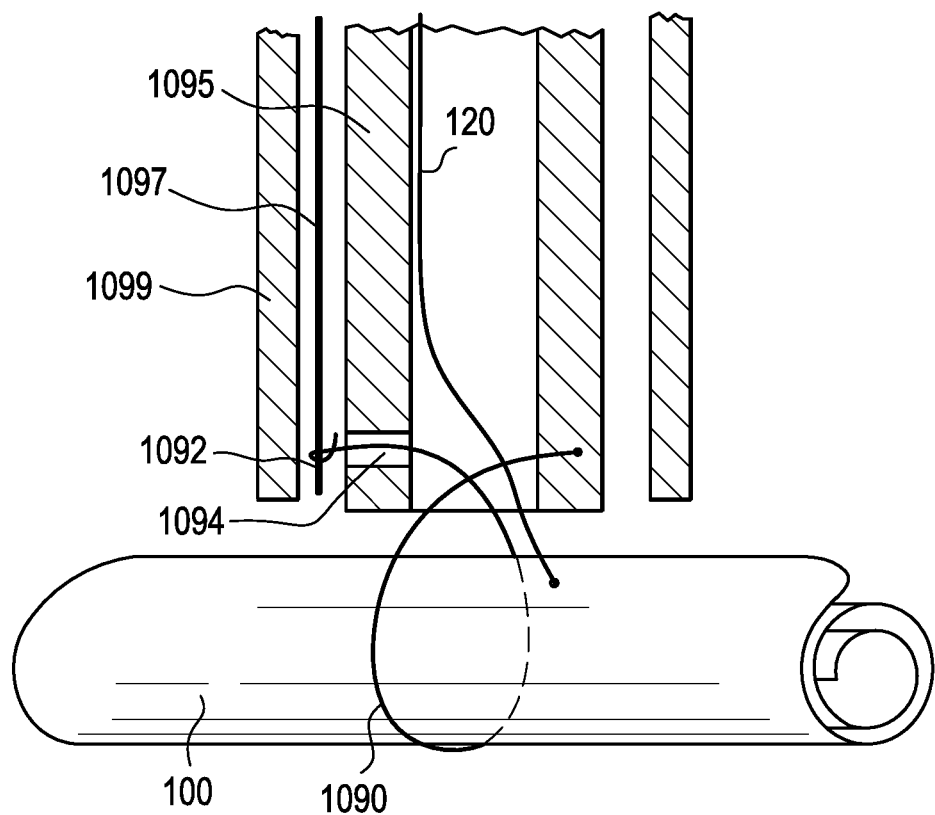

FIGS. 10A-10P illustrate additional delivery system features which may be adapted to the delivery systems described herein. FIG. 10A illustrates one embodiment of a push rod 1005, such as is described with reference to FIGS. 6 and 7A-7C, that includes a curved tip 1007 at its distal end. The curved tip 1007, according to one embodiment, is curved or angled in the direction opposite the vessel puncture site 15, which serves to bias a collapsed VCD 100 against the opposite side of the vessel 10 and away from the vessel puncture site 15 and to avoid back-out by the VCD 100. In other embodiments, however, the curved tip 1007 can have different configurations, such as a tip angled in the direction opposite that shown in FIG. 10A, or a substantially straight tip. In still other embodiments, a sheath and/or an actuator handle, such as those described with reference to FIGS. 9A-9I, includes a similarly formed curved tip.

FIGS. 10B-10D illustrate another embodiment of a push rod. In this embodiment, the push rod 1010 includes at least one biasing member 1012 extending from its distal end. The biasing member 1012 biases one end of a VCD 100 away from the push rod 1010 and thus away from the puncture site 15. FIG. 10B illustrates an angle formed between the VCD 100 and the push rod 1010 caused by the biasing member 1012. The angle formed and distance created should be large enough to space at least one end of the VCD 100 away from the vessel puncture site 15 and away from the distal end of the push rod 1010 and the sheath while the VCD 100 is positioned within the vessel 10. Otherwise, it is possible that the VCD 100 will back out into the puncture site 15 and not be properly positioned within the vessel 10. The biasing member 1012 shown in FIG. 10B is formed as a bent strip secured at or near the distal end of the push rod 1010 and exerting force against, but not attached to, the VCD 100. FIGS. 10C-10D illustrate other possible biasing member 1012 shapes, including an "S" shaped biasing member 1012 and a "C" shaped biasing member 1012, respectively. Any other suitable biasing member operable to bias the VCD 100 in a direction away from the puncture site 15 may be provided. Representative examples of other bias members include a spring, an elastic arm, or the like.

FIGS. 10E-10G illustrate additional embodiments of delivery systems that include a push rod or a delivery sheath having a protecting member extending radially therefrom. The protecting members are operable for preventing a VCD from backing out into the vessel puncture during delivery. The protecting member may be in the form of an annular ring. For example, FIG. 10E illustrates an embodiment in which a sheath 1020 includes a protecting member 1022 configured as a flexible annular ring extending radially from near the distal end of the sheath 1020. In one embodiment, the protecting member 1022 can be selectively constrained, such as by a collar or retention tab, such that the protecting member 1022 remains folded or otherwise not extended until within the vessel 10. Since the protecting member 1022 can have a diameter that is similar to or larger than the diameter of the vessel puncture site 15, resistance will be felt by the operator when extracting the sheath 1020 and, therefore, can assist in correctly positioning the sheath 1020, such as to align a side hole or other sheath features, such as is described with reference to FIG. 7D. Positioned against the vessel 10 wall, the protecting member 1022 also serves to temporarily seal, at least partially, the vessel puncture site 15. With a protecting member 1022 against the vessel puncture site 15, the VCD 100 can be pulled into the desired position since, even if its distal or proximal end attempts to approach the puncture site 15, no part of the VCD 100 will extend into the puncture and prevent correct positioning. Moreover, the at least partial sealing provided by the protecting member 1022 mitigates or limits significant bleeding from the vessel 10 while positioning the VCD 100.

According to another embodiment, a protecting member may be integrated with, or otherwise adapted to, a push rod device at or near its distal end in the same or similar manner as described with reference to FIG. 10E, or as follows. FIGS. 10E-10G illustrate a sheath 1025 having a push rod 1030 contained therein that includes a protecting member 1032. The protecting member 1032 of this embodiment is constructed of an elastic material, such as an elastic polymer, which, upon its release from the sheath 1025, allows expansion of the protecting member 1032 into an expanded configuration (e.g., a ring as illustrated, in one embodiment) extending radially from the push rod 1030. FIG. 10F illustrates an embodiment in which the protecting member 1032 is collapsed within the sheath 1025 and folded around the push rod 1030 towards its proximal end. FIG. 10G illustrates another embodiment of a protecting member 1032 loaded within a sheath 1025, in which the protecting member 1032 is folded toward the distal end of the push rod 1030.

The protecting members described herein may be formed from one or a combination of flexible or elastic polymers, such as those described with reference to FIG. 2.

In one embodiment, a protecting member is formed from a thin membrane with one or more expanding or elastic members coupled thereto and operable to cause radial expansion when the protecting member is released into a vessel. For example, each elastic member may be configured as an elastic or super-elastic wire, ribbon, or mesh, which may be formed from materials, such as, but not limited to, nickel-titanium alloy, stainless steel, super-elastic polymers, or any other suitable elastic or expandable materials, such as those described with reference to FIG. 2, or any combinations thereof.

FIGS. 10H-10I illustrate another embodiment of a protecting member. In this embodiment, a delivery system includes a sheath 1025, a push rod 1040, and an inflatable protecting member 1042 integrated with the push rod 1040. The inflatable protecting member 1042 can be formed in a ring-shape, or in any other shape or shapes, extending radially from the push rod 1040. After exiting the sheath 1025, as illustrated in FIG. 10I, the inflatable protecting member 1042 is inflated by forcing saline or other suitable fluid through a fill channel 1044, which passes longitudinally through the push rod 1040 and which is in fluid communication with and exits into an interior space of the inflatable protecting member 1042. After positioning and securing a VCD within a vessel, the inflatable protecting member 1042 is deflated and removed together with the push rod 1040.

FIGS. 10H-10I illustrate an inflatable protecting member 1042 having a ring or annular shape. In other embodiments, the inflatable protecting member 1042 is formed to have another shape. Examples of such other shapes include squares, rectangles, triangles, or other polygons. In other cases, the protecting member may be in the form of multiple protruding arms, or the like. Moreover, in embodiments in which the sheath 1025 and/or the push rod 1040 are configured for insertion into a vessel at an angle, the inflatable protecting member 1042 may be affixed to the push rod 1040 at an angle to compensate for the angled insertion. Similar orientation adjustments may be made to any other protecting member embodiment described herein to accommodate differing angles of insertion or alternate uses.

FIG. 10J illustrates an embodiment of a delivery system for delivering an articulated VCD, such as the articulated VCD 562 described with reference to FIG. 5E. In this embodiment, the articulated VCD 562, which includes two radial support frames 570, 575 connected by at least one joint 580, is delivered through a delivery sheath 1050 by a push rod 1055 or actuator handle in a compressed form, bending at least partially along the joint 580. The VCD 562 of this embodiment further includes a containment mechanism having members 1057, 1059 releasably retaining each radial support frame 570, 575 in a collapsed configuration. In one embodiment, the members 1057, 1059 of the containment mechanism are selectively releasable containment loops, each extending from a respective member 1056, 1058 that are releasable. As the articulated VCD 562 exits the sheath 1050, the joint 580 straightens to extend the two radial support frames 570, 575 within a vessel. After positioning, such as by an anchoring tab 120 and/or pull wire, the articulated VCD 562 is released to an expanded configuration by releasing the members 1057, 1059 from around the radial support frames 570, 575 expanding the radial support frames 570, 575 as illustrated in FIG. 5E.

FIGS. 10K-10M illustrate another embodiment for deploying an articulated VCD 562 (or any other VCD embodiment described herein), which includes additional means for navigating the articulated VCD 562 into position. In this embodiment, the articulated VCD 562 includes one or more rings 1060 or other channel-defining members coupled to one or both of the radial support frames 570, 575 and/or to the sealing membrane 565 extending therebetween. In one embodiment, each ring 1060 is positioned approximately along the longitudinal axis of the articulated VCD 562. The ring or rings 1060 allow the articulated VCD 101 to receive suitable guiding means. One embodiment of such guiding means is two guide wires 1062, 1064 capable of directing each of the two radial support frames 570, 575 into proper position within the vessel, as shown in FIGS. 10K-10M. In an embodiment using guide wires 1062, 1064, or any other guiding means passing through the ring or rings 1060, a joint 580 can optionally be eliminated since the two radial support frames 570, 575 can be spaced apart and positioned within the vessel using the guide wires 1062, 1064. Though, in another embodiment, a joint 580 is used in addition to guiding means to facilitate deployment as well as to support a sealing membrane 565.

In use, according to one embodiment, after concluding an endovascular procedure, the two guide wires 1062, 1064 are inserted through a sheath 1050, one extending from the access site in the distal direction of the vessel 10 and the other extending in the proximal direction, as illustrated in FIG. 10K. Next, a compressed articulated VCD 562 is loaded into the sheath 1050 with the guide wires 1062, 1064 threaded through the rings 1060, as illustrated in FIG. 10L. FIG. 10M depicts the articulated VCD 562 after being released from the sheath 1050 and extended longitudinally within the vessel on either side of the puncture site. Finally, the guide wires 1062, 1064 are removed and the containment mechanism (which may be any suitable containment mechanism described herein) is released from the two radial support frames 570, 575. This causes the articulated VCD 562 to fully expand within the vessel 10 and the sealing membrane 565 to be pressed against the puncture site to facilitate hemostasis.

FIGS. 10N-10P illustrate examples of other embodiments of delivery systems for releasing a containment mechanism and thereby allowing a VCD to radially expand within a vessel. These delivery systems may be utilized with any VCD embodiment described herein and any containment mechanism that includes one or more releasable members. With reference to FIG. 10N, a VCD, such as the VCD 100 described with reference to FIG. 2, is retained in a compressed configuration by a containment mechanism that includes a wire loop 1070 (or any other looped member), which, when severed, releases the loop 1070 and allows the VCD 100 to expand within a vessel. The wire loop 1070 has a first end 1072, which is threaded through the distal end of a delivery sheath 1075 and into the distal end of a needle-like cutting tube 1080. A second end 1074 of the wire loop 1070 is threaded via a side hole 1076 formed in the sheath 1075, which may be the same as, or different from, the side hole described with reference to FIG. 9A. After passing through the side hole 1076, the second end 1074 of the wire loop 1070 is passed into the distal end of the cutting tube 1080. The cutting tube 1080, which has an external diameter at least slightly smaller than the inner diameter of sheath 1075, has at least one edge at its distal end that is sharp and operable for cutting the second end 1074 of the wire loop 1070 when passed by the side hole 1076.

FIG. 10O illustrates another embodiment of a delivery system operable for cutting the second end 1074 of the wire loop 1070. In this embodiment, the sheath 1085 is closed at its distal end with the exception of a single hole 1087 sized to allow the collapsed VCD 100 and the ends 1072, 1074 of the wire loop 1070 to pass therethrough, but having a diameter smaller than the outer diameter of the cutting tube 1080, which provides a cutting surface 1089 for receiving the sharp edge of the cutting tube 1080. The sheath 1085 may be manufactured with only the single hole 1087, or it may be subsequently sealed by a separate flat plug having the hole 1087 formed therethrough and securable into the distal end of the sheath 1085.

In operation, the first end 1072 is threaded through the channel of the cutting tube 1080 while the second end 1074 is passed outside the cutting tube 1080, between its external surface and the inner surface of the sheath 1085. By pushing the sharp edge of the cutting tube 1080 against the cutting surface 1089 at the end of the sheath 1085, a shearing force severs the second end 1074. Severing the second end 1074 of the wire loop 1070 in any of these embodiments releases the containment mechanism and allows the VCD 100 to expand from its compressed state.

FIG. 10P illustrates yet another embodiment of a delivery system operable to release a containment mechanism of a VCD 100. In this embodiment, the VCD 100 is retained in its collapsed state by a wire loop 1090 (or other strip, string, or other member, etc.). One end of wire loop 1090 is secured to a push rod 1095 or actuator handle (e.g., tied, glued, formed therein, or otherwise affixed). The opposite end of the wire loop 1090 includes a ring, hole, or loop 1092 and is threaded through a channel 1094 formed in a side wall of the push rod 1095. The wire loop 1090 is stretched or otherwise retained in a taut configuration to maintain the VCD 100 in its collapsed configuration. A release rod 1097 secured in a fixed relation to the sheath 1099 (e.g., inserted into or otherwise affixed to an inner wall of the sheath 1099) is initially positioned through the ring, hole, or loop 1092 and retains the wire loop 1090 in the taut configuration.

In use, while retracting the sheath 1099 and leaving the push rod 1095 within the puncture, the release rod 1097 is pulled out of the ring, hole, or loop 1092 in the second end of the wire loop 1090, which releases the tension on the wire loop 1090. After the wire loop 1090 is released by extracting the release rod 1097, the push rod 1095 is also retracted from the vessel puncture. Because the wire loop 1090 is secured to the push rod 1095 and no longer held in position by the release rod 1097, the wire loop 1090 is released from the VCD 100, allowing the VCD 100 to expand. In one embodiment, an anchoring tab 120 and/or pull string remains connected to the VCD 100, which can be used to facilitate positioning the VCD 100 within the vessel and to be secured to the patient as described herein.

The VCDs and associated delivery systems described herein advantageously provide means for at least temporarily closing or otherwise sealing punctures in a patient's vasculature or other body lumen. Quicker and more effective sealing advantageously avoids the time and expense of applying manual pressure to the puncture, which would otherwise be required by conventional methods. The various support frames and sealing membranes disclosed effectively retain the closure device within the vessel while requiring little additional surgical manipulation by the operator during delivery. Moreover, the embodiments described herein also avoid unnecessary widening of the vessel puncture due to their ability to collapse the VCD in a significantly reduced profile during delivery. Similarly, the ability to deploy example VCDs via various sheath configurations provides some embodiments that are more beneficial for use with smaller sheath access than are presently available, such as with sheaths used during cardiac catheterization procedures.

It is appreciated that these and many other advantages will be appreciated, and modifications and variations of the devices, systems, and methods described herein, such as dimensional, size, and/or shape variations, will be apparent to those skilled in the art from the foregoing detailed description. Such modifications and variations are intended to come within the scope of the appended claims.

We claim:

1. A vasculature closure device, comprising:
   an expandable support frame deployable within a vessel;
   a sealing membrane at least partially supported by the expandable support frame;
   a cross-member support extending across at least a portion of the sealing membrane and attached to opposing sides of the support frame; and
   an anchoring tab or a pull string fixedly attached to at least one of the support frame, the sealing membrane, and the cross-member support;
   wherein, upon deploying the support frame within the vessel, the device is positioned entirely within the vessel except for the anchoring tab or the pull string; and
   wherein, upon expanding the support frame within the vessel, the device is configured to intraluminally push the sealing membrane against a puncture site existing in a vessel wall, such that the sealing membrane prevents fluid blood leakage through the puncture site.

2. The device of claim 1, wherein, upon expanding the support frame within the vessel, the device is configured to intraluminally position the support frame, the sealing membrane, and the cross-member support on an inner surface of the vessel wall such that the sealing membrane is pushed against the puncture site.

3. The device of claim 1, wherein the device comprises at least two cross-member supports extending across at least a portion of the sealing membrane and attached to opposing sides of the support frame, and wherein the cross-member supports are generally parallel to one another.

4. The device of claim 1, wherein the support frame is formed of a non-biodegradable material, and wherein the cross-member support comprises a wire formed of a biodegradable material.

5. The device of claim 4, wherein the support frame is formed of a non-biodegradable metal, and wherein the wire is formed of a biodegradable polymer.

6. The device of claim 1, further comprising two ear supports extending away from the sealing membrane in opposite directions and attached to opposing sides of the support frame.

7. The device of claim 1, wherein the device is adapted for rolling and unrolling along a longitudinal axis generally aligned with and extending along the length of the vessel.

8. The device of claim 7, wherein, when expanding, the support frame is adapted at least partially to unroll into an expanded configuration having a radius of curvature larger than a radius of curvature of the vessel.

9. The device of claim 7, wherein the device is adapted for rolling into a collapsed configuration such that opposing sides of the support frame overlap one another.

10. The device of claim 1, wherein the sealing membrane defines an outer edge around its periphery, and wherein the support frame comprises a peripheral support frame, at least a portion of which is positioned at or near at least a portion of the outer edge of the sealing membrane.

11. The device of claim 1, wherein, upon expanding, the support frame is adapted to exert a radial pressure against the vessel wall, the radial pressure ranging between approximately 2 mm Hg and approximately 400 mm Hg.

12. The device of claim 1, wherein the sealing membrane is formed of a biodegradable material.

13. The device of claim 1, wherein at least a portion of the support frame is formed of a biodegradable material.

14. The device of claim 1, wherein the support frame is formed of a pre-shaped material adapted for expanding the sealing membrane when in its stable state.

15. The device of claim 14, wherein the pre-shaped material comprises at least one of: (a) a shape memory metal or (b) a shape memory polymer.

16. A vasculature closure device, comprising:
an expandable support frame deployable within a vessel;
a sealing membrane at least partially supported by the expandable support frame; and
a cross-member support extending across at least a portion of the sealing membrane and attached to opposing sides of the support frame;
wherein the support frame is formed of a non-biodegradable material; and
wherein the cross-member support comprises a wire formed of a biodegradable material.

17. The device of claim 16, wherein, upon expanding the support frame within the vessel, the device is configured to intraluminally push the sealing membrane against a puncture site existing in a vessel wall.

18. The device of claim 16, wherein the support frame is formed of a non-biodegradable metal, and wherein the wire is formed of a biodegradable polymer.

19. The device of claim 16, wherein, upon expanding the support frame within the vessel, the device is configured to intraluminally position the support frame, the sealing membrane, and the cross-member support on an inner surface of the vessel such that the sealing membrane is pushed against a puncture site existing in a vessel wall.

20. The device of claim 16, further comprising an anchoring tab or a pull string fixedly attached to at least one of the support frame, the sealing membrane, and the cross-member support, wherein, upon deploying the support frame within the vessel, the device is positioned entirely within the vessel except for the anchoring tab or the pull string.

21. The device of claim 16, wherein the device comprises at least two cross-member supports extending across at least a portion of the sealing membrane and attached to opposing sides of the support frame, and wherein the cross-member supports are generally parallel to one another.

22. The device of claim 16, further comprising two ear supports extending away from the sealing membrane in opposite directions and attached to opposing sides of the support frame.

23. The device of claim 16, wherein the device is adapted for rolling and unrolling along a longitudinal axis generally aligned with and extending along the length of the vessel.

24. The device of claim 23, wherein, when expanding, the support frame is adapted at least partially to unroll into an expanded configuration having a radius of curvature larger than a radius of curvature of the vessel.

25. The device of claim 23, wherein the device is adapted for rolling into a collapsed configuration such that opposing sides of the support frame overlap one another.

26. A vasculature closure device, comprising:
an expandable support frame deployable within a vessel;
a sealing membrane at least partially supported by the expandable support frame;
a cross-member support extending across at least a portion of the sealing membrane and attached to opposing sides of the support frame; and
two ear supports extending away from the sealing membrane in opposite directions and attached to opposing sides of the support frame;
wherein, upon expanding the support frame within the vessel, the device is configured to intraluminally push the sealing membrane against a puncture site existing in a vessel wall, such that the sealing membrane prevents fluid blood leakage through the puncture site.

27. The device of claim 26, wherein, upon expanding the support frame within the vessel, the device is configured to intraluminally position the support frame, the sealing membrane, the cross-member support, and the ear supports on an inner surface of the vessel such that the sealing membrane is pushed against a puncture site existing in a vessel wall.

28. The device of claim 26, further comprising an anchoring tab or a pull string fixedly attached to at least one of the support frame, the sealing membrane, and the cross-member support, wherein, upon deploying the support frame within the vessel, the device is positioned entirely within the vessel except for the anchoring tab or the pull string.

29. The device of claim 26, wherein the support frame is formed of a non-biodegradable material, and wherein the cross-member support comprises a wire formed of a biodegradable material.

30. The device of claim 26, wherein the device is adapted for rolling and unrolling along a longitudinal axis generally aligned with and extending along the length of the vessel.

31. A vasculature closure device, comprising:
an expandable support frame deployable within a vessel;
a sealing membrane at least partially supported by the expandable support frame;
a cross-member support extending across at least a portion of the sealing membrane and attached to opposing sides of the support frame; and
an anchoring tab or a pull string fixedly attached to at least one of the support frame, the sealing membrane, and the cross-member support;
wherein the support frame is formed of a non-biodegradable material;
wherein the sealing membrane is formed of a biodegradable material; and
wherein, upon deploying the support frame within the vessel, the device is positioned entirely within the vessel except for the anchoring tab or the pull string.

32. A vasculature closure device, comprising:
an expandable support frame deployable within a vessel;
a sealing membrane at least partially supported by the expandable support frame;
a cross-member support extending across at least a portion of the sealing membrane and attached to opposing sides of the support frame; and
an anchoring tab or a pull string fixedly attached to at least one of the support frame, the sealing membrane, and the cross-member support;
wherein the device is adapted for rolling and unrolling along a longitudinal axis generally aligned with and extending along the length of the vessel;
wherein the device is adapted for rolling into a collapsed configuration such that opposing sides of the support frame overlap one another; and
wherein, upon deploying the support frame within the vessel, the device is positioned entirely within the vessel except for the anchoring tab or the pull string.

* * * * *